(12) United States Patent
Jatsch et al.

(10) Patent No.: US 11,098,019 B2
(45) Date of Patent: Aug. 24, 2021

(54) MATERIALS FOR ORGANIC ELECTROLUMINESCENT DEVICES

(71) Applicant: Merck Patent GmbH, Darmstadt (DE)

(72) Inventors: Anja Jatsch, Frankfurt am Main (DE); Amir Hossain Parham, Frankfurt am Main (DE); Thomas Eberle, Landau (DE); Tobias Grossmann, Darmstadt (DE); Jonas Valentin Kroeber, Frankfurt am Main (DE)

(73) Assignee: Merck Patent GmbH, Darmstadt (DE)

( * ) Notice: Subject to any disclaimer, the term of this patent is extended or adjusted under 35 U.S.C. 154(b) by 416 days.

(21) Appl. No.: 15/748,437

(22) PCT Filed: Jul. 1, 2016

(86) PCT No.: PCT/EP2016/001117
§ 371 (c)(1),
(2) Date: Jan. 29, 2018

(87) PCT Pub. No.: WO2017/016630
PCT Pub. Date: Feb. 2, 2017

(65) Prior Publication Data
US 2018/0222872 A1    Aug. 9, 2018

(30) Foreign Application Priority Data
Jul. 30, 2015  (EP) .................................... 15178986

(51) Int. Cl.
| | | |
|---|---|---|
| *H01L 51/50* | (2006.01) |
| *C07D 251/24* | (2006.01) |
| *C07D 401/10* | (2006.01) |
| *C07D 403/10* | (2006.01) |
| *C07D 405/10* | (2006.01) |
| *C07D 409/10* | (2006.01) |
| *H01L 51/00* | (2006.01) |
| *C09K 11/06* | (2006.01) |

(52) U.S. Cl.
CPC ......... *C07D 251/24* (2013.01); *C07D 401/10* (2013.01); *C07D 403/10* (2013.01); *C07D 405/10* (2013.01); *C07D 409/10* (2013.01); *C09K 11/06* (2013.01); *H01L 51/0052* (2013.01); *H01L 51/0067* (2013.01); *H01L 51/5016* (2013.01); *H01L 51/5076* (2013.01); *H01L 51/5096* (2013.01); *C09K 2211/1011* (2013.01); *C09K 2211/1062* (2013.01); *C09K 2211/1066* (2013.01); *H01L 51/0072* (2013.01); *Y02E 10/549* (2013.01)

(58) Field of Classification Search
None
See application file for complete search history.

(56) References Cited

U.S. PATENT DOCUMENTS

| | | | |
|---|---|---|---|
| 2007/0015007 A1* | 1/2007 | Shin ...................... H05B 33/14 | 428/690 |
| 2010/0045170 A1* | 2/2010 | Lee ......................... C07C 25/22 | 313/504 |
| 2011/0121274 A1 | 5/2011 | Parham et al. | |
| 2012/0214993 A1† | 8/2012 | Aihara | |
| 2015/0200373 A1 | 7/2015 | Cho et al. | |
| 2015/0318487 A1 | 11/2015 | Ito et al. | |
| 2016/0248020 A1* | 8/2016 | Ondari ................. C07D 401/04 | |
| 2016/0276596 A1* | 9/2016 | Jang ........................ H01B 1/04 | |
| 2016/0293852 A1 | 10/2016 | Huh et al. | |
| 2016/0308147 A1 | 10/2016 | Parham et al. | |
| 2018/0175302 A1 | 6/2018 | Jang et al. | |
| 2018/0269402 A1 | 9/2018 | Huh et al. | |

FOREIGN PATENT DOCUMENTS

| | | |
|---|---|---|
| EP | 2108689 A2 | 10/2009 |
| EP | 3127988 A1 | 2/2017 |
| EP | 3222695 A1 | 9/2017 |
| JP | 2009-249378 A | 10/2009 |
| JP | 2017-513224 A | 5/2017 |
| JP | 2017-531305 A | 10/2017 |
| JP | 2017-535071 A | 11/2017 |
| KR | 10-0537499 B1 | 12/2005 |
| KR | 2012-0046778 A | 5/2012 |
| KR | 10-1537499 B1 | 7/2015 |
| KR | 101537500 B1 | 7/2015 |
| KR | 20150074603 A | 7/2015 |

(Continued)

OTHER PUBLICATIONS

Database Caplus [Online] Chemical Abstracts Service, XP002760867, Database Accession No. 2015:1199479, Jul. 23, 2015.
International Preliminary Report on Patentability received for PCT Patent Application No. PCT/EP2016/001117, dated Feb. 8, 2018, 7 pages.
International Search Report and Written Opinion received for PCT Patent Application No. PCT/EP2016/001117, dated Sep. 27, 2016, 9 pages.

\* cited by examiner
† cited by third party

*Primary Examiner* — Gregory D Clark
(74) *Attorney, Agent, or Firm* — Faegre Drinker Biddle & Reath LLP

(57) ABSTRACT

Fluorene derivatives that are connected in one or more of the 1-, 1'-, 4-, or 4'-positions in any combination to a carbon atom of a diaryl substituted triazinyl or pyrimidinyl derivative. The fluorene derivatives are not spirobifluorene derivatives. The compounds are suitable for use in electronic devices, in particular organic electroluminescent devices, comprising these compounds. In some embodiments, the compounds are used as matrix materials for phosphorescent or fluorescent emitters as well as a hole-blocking or an electron-transport layer.

33 Claims, No Drawings

(56) References Cited

FOREIGN PATENT DOCUMENTS

| | | |
|---|---|---|
| KR | 10-1593368 B1 | 2/2016 |
| KR | 10-2016-0111780 A | 9/2016 |
| TW | 201302973 A | 1/2013 |
| TW | 201619350 A | 6/2016 |
| WO | 2011/021689 A1 | 2/2011 |
| WO | WO-2012150826 A1 | 11/2012 |
| WO | 2013/012298 A1 | 1/2013 |
| WO | 2014/023388 A1 | 2/2014 |
| WO | 2015073343 A1 | 5/2015 |
| WO | WO-2015090504 A2 | 6/2015 |
| WO | 2015/152633 A1 | 10/2015 |
| WO | 2016/003225 A2 | 1/2016 |
| WO | 2015153633 A2 | 10/2018 |

MATERIALS FOR ORGANIC ELECTROLUMINESCENT DEVICES

The present invention relates to materials for use in electronic devices, in particular in organic electroluminescent devices, and to electronic devices, in particular organic electroluminescent devices, comprising these materials.

The structure of organic electroluminescent devices (OLEDs) in which organic semiconductors are employed as functional materials is described, for example, in U.S. Pat. Nos. 4,539,507, 5,151,629, EP 0676461 and WO 98/27136. The emitting materials employed here are increasingly organometallic complexes which exhibit phosphorescence instead of fluorescence. For quantum-mechanical reasons, an up to four-fold increase in the energy and power efficiency is possible using organometallic compounds as phosphorescence emitters. In general, however, there is still a need for improvement in the case of OLEDs, in particular also in the case of OLEDs which exhibit triplet emission (phosphorescence), for example with respect to efficiency, operating voltage and lifetime.

The properties of phosphorescent OLEDs are not only determined by the triplet emitters employed. In particular, the other materials used, such as matrix materials, hole-blocking materials, electron-transport materials, hole-transport materials and electron- or exciton-blocking materials, are also of particular importance here. Improvements in these materials can thus also result in significant improvements in the OLED properties, particularly with respect to the efficiency, the lifetime and the thermal stability of the materials.

The object of the present invention is the provision of compounds which are suitable for use in an OLED, in particular as matrix material for phosphorescent emitters, but also as hole-blocking material, as electron-transport material or optionally as a material for a charge generation layer. A further object of the present invention is to provide further organic semiconductors for organic electroluminescent devices so as to provide the person skilled in the art with a greater possible choice of materials for the production of OLEDs.

It is known to use compounds with both non-spiro fluorenyl groups and triazinyl groups in OLEDs. For example, U.S. Pat. No. 7,651,790 discloses the use of OLEDs with a compound of the formula A-C-B where A is a hole-transporting group (including non-spiro fluorenyl groups among others), B is an electron-transporting group (including triazinyl groups among others) and C is a bond or linking group.

Commonly-assigned WO 2010/015306 and WO 2005/053055 discloses OLEDs with fluorenes, including 9,9-(dimethyl or diphenyl) as well as bis-9,9'-spiro-examples, substituted in any position with nitrogen containing heterocycles including triazines and pyrimidines.

U.S. Pat. Nos. 6,821,643, 6,229,012 and 6,225,467 discloses fluorenes substituted in the 2-position with triazinyl groups. US 2004/0147742 and Wu, Appl. Phys. Lett., 81(4), 577-592 discloses fluorenes substituted in the 2-position with pyrimidines.

WO 2015/073343 discloses OLEDs with triazine compounds substituted with at least two fluorenyl groups, one being a 9,9-diphenylfluorene. Examples of both 3- and 4-triazinyl substituted fluorenes are shown. KR 2013115161 discloses OLEDs with a 1-triazinyl-9,9-dimethylfluorene where the triazine is substituted in the 4-position with 1-benzofuran and in the 6-position with a N-indene derivative. KR 2013061371 discloses OLEDs with a 1-(4-phenyl)triazinyl-9,9-dimethylfluorene derivative.

US20100045170 describes OLEDs with a 1-(9-(10-(2-diazinyl)-anthracenyl)diazine)-9,9-dimethylfluorene.

Commonly assigned WO 2014/023388 discloses OLEDs with 9,9'-spirobifluorenes that are mono-substituted in the 1- or 4-positions with triazinyl or pyrimidinyl groups. Commonly assigned WO 2011/006574 discloses OLEDs with 9,9'-spirobifluorenes that are di-substituted in the 4,4'-positions with triazinyl or pyrimidinyl groups.

Surprisingly, it has been found that certain compounds described in greater detail below achieve this object, are highly suitable for use in OLEDs and result in improvements in the organic electroluminescent device. The improvements here relate, in particular, to the lifetime and/or the operating voltage. The present invention therefore relates to these compounds and to electronic devices, in particular organic electroluminescent devices, which comprise compounds of the type described below.

The compounds of the invention are generally fluorene derivatives that are connected in one or more of the 1-, 1'-, 4-, or 4'-positions in any combination to a carbon atom of a triazinyl or pyrimidinyl derivative. In the sense of the invention, the fluorene derivative of the invention uses the following numbering convention:

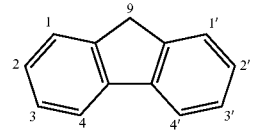

In particular, the present invention relates to a compound of the formula (I),

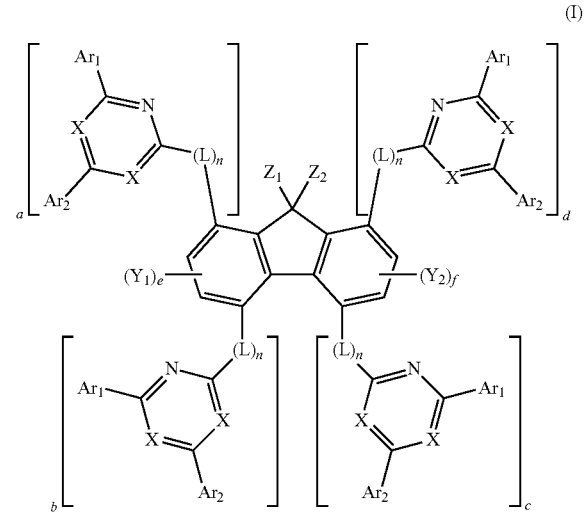

where the following applies to the symbols and indices used:

$Z_1$ and $Z_2$ are on each occurrence, identically or differently, H, D, F, Cl, Br, I, CHO, $N(Ar_1)_2$, $C(=O)Ar_1$, $P(=O)(Ar_1)_2$, $S(=O)Ar_1$, $S(=O)_2Ar_1$, $CR_2=CR_2Ar_1$, CN, $NO_2$, $Si(R_1)_3$, $B(OR_1)_2$, $B(R_1)_2$, $B(N(R_1)_2)_2$, $OSO_2R_1$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals $R_1$, where one or more, preferably non-adjacent $CH_2$ groups may be replaced by $(R_1)C=C(R_1)$, $C≡C$, $Si(R_1)_2$, $Ge(R_1)_2$, $Sn(R_1)_2$, $C=O$, $C=S$, $C=Se$, $C=N(R_1)_2$, $P(=O)(R_1)$, $SO$, $SO_2$, $N(R_1)_2$, $O$, $S$ or $CON(R_1)_2$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R_1$, or an aryloxy or heteroaryloxy group having 5 to 60 aromatic ring atoms, which may be substituted by one or more radicals $R_1$.

The fluorene derivatives of the invention are not bis-9,9'-spirobifluorenes; that is, the $Z_1$ and $Z_2$ groups at the 9-position do not represent another fluorene group. Thus, the heterocyclic substituted fluorene nucleus of the invention is not a derivative of:

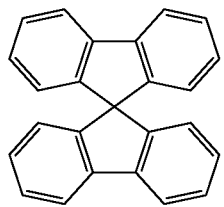 [SMILES: c1ccc2c(c1)-c1ccccc1C21c2ccccc2-c2ccccc21]

although a bis-9,9-spirobifluorene group may be a further substituent or linking group as described below. It should be understood that in some embodiments, $Z_1$ and $Z_2$ may form a spiro saturated ring system; for example, $Z_1$ and $Z_2$ may represent a cyclopentyl or cyclohexyl ring system. However, it is preferred that $Z_1$ and $Z_2$ are separate substituents from each other and are not connected to each other at any point other than the 9-position of the fluorene nucleus.

$Y_1$ and $Y_2$ are on each occurrence, identically or differently, D, F, Cl, Br, I, CHO, $N(Ar_1)_2$, $C(=O)Ar_1$, $P(=O)(Ar_1)_2$, $S(=O)Ar_1$, $S(=O)_2Ar_1$, $(R_1)C=C(R_1)Ar_1$, CN, $NO_2$, $Si(R_1)_3$, $B(OR_1)_2$, $B(R_1)_2$, $B(N(R_1)_2)_2$, $OSO_2R_1$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals $R_1$, where one or more, preferably non-adjacent $CH_2$ groups may be replaced by $(R_1)C≡C(R_1)$, $C≡C$, $Si(R_1)_2$, $Ge(R_1)_2$, $Sn(R_1)_2$, $C=O$, $C=S$, $C=Se$, $C=N(R_1)_2$, $P(=O(R_1)_2$, $SO$, $SO_2$, $N(R_1)_2$, $O$, $S$ or $CON(R_1)_2$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R_1$, or an aryloxy or heteroaryloxy group having 5 to 60 aromatic ring atoms, which may be substituted by one or more radicals $R_1$, or a combination of these systems; two or more adjacent substituents $Y_1$ or $Y_2$ may also form a annulated mono- or polycyclic, aliphatic or aromatic or heteroaromatic ring system with one another.

$Ar_1$ and $Ar_2$ are on each occurrence, identically or differently, an aromatic or heteroaromatic ring system having 5 to 23 aromatic ring atoms, which may be substituted by one or more radicals $R_1$, preferably non-aromatic radicals $R_1$, with the proviso that a heteroaromatic ring system is connected through a carbon-carbon bond;

$R_1$ is on each occurrence, identically or differently selected from the group consisting of H, D, F, Cl, Br, I, CN, $Si(R_2)_3$, a straight-chain alkyl, alkoxy or thioalkyl group having 1 to 40 C atoms or a branched or cyclic alkyl, alkoxy or thioalkyl with 3-40 C-atoms which may be substituted by one or more radicals $R_2$, wherein each one or more non-adjacent $CH_2$ groups by may be replaced by $C(R_2)=C(R_2)$, $Si(R_2)_2$, $C=NR_2$, $P(=O)(R_2)$, $SO$, $SO_2$, $NR_2$, $O$, $S$ or $CONR_2$ and where one or more H atoms may be replaced by D, F, Cl, Br or I, an aromatic or heteroaromatic ring system having 6 to 40 carbon atoms which may be substituted by one or more radicals $R_2$, an aryloxy group having 5 to 60 aromatic ring atoms which may be substituted by one or more radicals $R_2$, or an aralkyl group having 5 to 60 aromatic ring atoms which may be substituted by one or more radicals $R_2$, where optionally two or more adjacent substituents $R_1$ can form a mono- or polycyclic, aliphatic, aromatic or heteroaromatic ring system with one another, which may be substituted with one or more radicals $R_2$; where $R_2$ is selected from the group consisting of H, D, F, an aliphatic hydrocarbon radical having 1 to 20 carbon atoms or an aromatic or heteroaromatic ring system having 5 to 30 C atoms, wherein two or more adjacent substituents $R_2$ can form a mono- or polycyclic, aliphatic, aromatic or heteroaromatic ring system with one another;

X is on each occurrence, identically or differently, $CR_1$ or N, with the proviso that at least one X stands for N.

L is on each occurrence, identically or differently, an aromatic or heteroaromatic ring system having 5-30 aromatic ring atoms, which may be substituted by one or more non-aromatic radicals $R_1$.

a, b, c and d are each, identically or differently, 0 or 1 with the proviso that at least one of a, b, c or d is 1.

e and f are each, identically or differently, 0, 1, 2 or 3.

n is on each occurrence, identically or differently, 0 or 1.

In a preferred embodiment of the present invention, the compound of formula (I) is not the following compound:

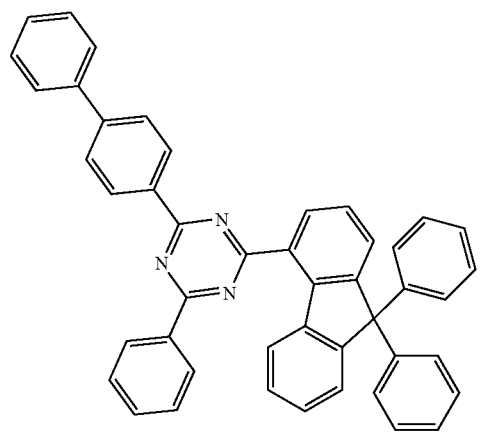

Unless indicated otherwise, an aryl group in the context of this invention contains from 6 to 24 carbon atoms; a heteroaryl group within the meaning of this invention containing from 2 to 24 carbon atoms and at least one heteroatom, with the proviso that the sum of carbon atoms and hetero atoms is at least 5. The heteroatoms are preferably selected from N, O and S. Among an aryl or heteroaryl group is either a simple aromatic ring, for example benzene, or a simple heteroaromatic ring, for example pyridine, pyrimidine, thiophene, etc., or a fused aryl or heteroaryl, such as naphthalene, anthracene, phenanthrene, quinoline, isoquinoline, etc.

Unless indicated otherwise, an aromatic ring system in the sense of this invention contains from 6 to 40 carbon atoms in the ring system. Unless indicated otherwise, a heteroaromatic ring system in the sense of this invention contains 1 to 40 carbon atoms and at least one heteroatom in the ring system, with the proviso that the sum of carbon atoms and hetero atoms is at least 5. The heteroatoms are preferably selected from N, O and S. Unless indicated otherwise, an aromatic or heteroaromatic ring system in the context of this invention is to be understood as a system that does not necessarily contain only aryl or heteroaryl groups, but in which a plurality of aryl or heteroaryl groups are connected by a non-aromatic moiety, such as, for example, a C, N or O atom or a carbonyl group. For example, unless indicated otherwise, systems such as 9,9'-spirobifluorene, 9,9-diarylfluorene, triarylamine, stilbene, etc., are aromatic ring systems for the purposes of this invention. Also included are systems in which two or more aryl groups are connected, for example, by a linear or cyclic alkyl group or by a silyl group. Furthermore, to systems in which two or more aryl or heteroaryl groups are directly bonded to each other, such, for example, biphenyl, terphenyl or quaterphenyl be understood unless indicated otherwise, also as an aromatic or heteroaromatic ring system.

For the purposes of this invention, a cyclic alkyl, alkoxy or thioalkoxy means a monocyclic, bicyclic or an a polycyclic group.

In the present invention, a C1 to C 40 alkyl group, in which individual H atoms or $CH_2$ groups may be substituted by the above-mentioned groups, include methyl, ethyl, n-propyl, i-propyl, cyclopropyl, n-butyl, i-butyl, s-butyl, t-butyl, cyclobutyl, 2-methylbutyl, n-pentyl, s-pentyl, t-pentyl, 2-pentyl, neo-pentyl, cyclopentyl, n hexyl, s-hexyl, t-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo [2,2,2] octyl, 2-bicyclo [2.2.2] octyl, 2-(2,6-dimethyl) octyl, 3-(3,7-dimethyl) octyl, adamantyl, trifluoromethyl, pentafluoroethyl, 2,2,2-trifluoroethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyl-n-n-hexadec-1-yl, 1,1-diethyl-n-octadec-1-yl, 1-(n-propyl) cyclohex-1-yl, 1-(n-butyl)cyclohex-1-yl, 1-(N-hexyl)-cyclohex-1-yl, 1-(n-octyl)-cyclohex-1-yl and 1-(n-decyl)cyclohex-1-yl. Examples of an alkenyl group include ethenyl, propenyl, butenyl, pentenyl, cyclopentenyl, hexenyl, cyclohexenyl, heptenyl, cycloheptenyl, octenyl, cyclooctenyl or cyclooctadienyl. Examples of an alkynyl group include, for example, ethynyl, propynyl, butynyl, pentynyl, hexynyl, heptynyl or octynyl. An alkoxy group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group having 1 to 40 C atoms is taken to mean, in particular, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkoxy or thioalkyl groups in accordance with the present invention may be straight-chain, branched or cyclic, where one or more non-adjacent $CH_2$ groups may be replaced by the above-mentioned groups; furthermore, one or more H atoms may also be replaced by D, F, Cl, Br, I, CN or $NO_2$, preferably F, Cl or CN, further preferably F or CN, particularly preferably CN.

Unless indicated otherwise, an aromatic or heteroaromatic ring system having 5-60 aromatic ring atoms which may be substituted with residues above yet and which can be linked via any position on the aromatic or heteroaromatic compounds, for example, groups are understood to be derived from benzene, naphthalene, anthracene, benzanthracene, phenanthrene, benzophenanthrene, pyrene, chrysene, perylene, fluoranthene, benzfluoranthen, naphthacene, pentacene, benzopyrene, biphenyl, biphenyl, terphenyl, fluorene, spirobifluorene, dihydrophenanthrene, dihydropyrene, tetrahydropyrene, cis- or trans-indenofluorene, cis- or trans-monobenzoindenofluorene, cis- or trans-dibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazol, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, chinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzpyrimidine, quinoxaline, 1,5-diaza-anthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2, 4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

In the above, $R_1$ refers to a first substituent and $R_2$ is a further optional substituent on $R_1$ as well on L, $Z_1$, $Z_2$, $Y_1$ and $Y_2$. Both $R_1$ and $R_2$ can be chosen independently from the same groups as described. Adjacent radicals or adjacent substituents in the sense of the present application are taken to mean substituents which are bonded to C atoms which are in turn bonded directly to one another or substituents which are bonded to the same C atom.

In compounds which are processed by vacuum evaporation, the alkyl groups preferably have not more than five C atoms, particularly preferably not more than 4 C atoms, very particularly preferably not more than 1 C atom. For compounds which are processed from solution, suitable compounds are also those which are substituted by alkyl groups, in particular branched alkyl groups, having up to 10 C atoms or which are substituted by oligoarylene groups, for example ortho-, meta-, para- or branched terphenyl groups. It should be understood that for compounds that are processed by vacuum deposition, more than one compound can be co-evaporated at the same time to form a mixed layer. For example, a mixture of two or more different host compounds (one being a compound according to the invention) can be mixed together at a predetermined ratio and then the solid mixture co-evaporated to form a mixed matrix layer (with a light-emitting material). Alternatively, two (or more) compounds can be separately evaporated and the resulting vapors mixed at the appropriate ratios to form a mixed layer.

If the compounds of the formula (I) or the preferred embodiments are used as matrix material for a phosphorescent emitter or in a layer which is directly adjacent to a phosphorescent layer, it is furthermore preferred for $R_1$, $R_2$, $Z_1$, $Z_2$, $Y_1$, $Y_2$, $Ar_1$ and $Ar_2$ and L of the compound to contain no condensed aryl or heteroaryl groups in which more than two six-membered rings are condensed directly onto one another. However, one exception is a triphenylene group, which has more than two condensed six-membered rings, but is still suitable and preferred as a triplet matrix material. It is generally advantageous for the triplet energy of the compound used as a matrix material or in an adjacent layer to be the same or greater than the triplet energy of the phosphorescent material in the emitting layer.

The compounds according to the invention described above, in particular compounds which are substituted by reactive leaving groups, such as bromine, iodine, chlorine, boronic acid or boronic acid ester, or by reactive, polymerisable groups, such as olefins, styrenes, acrylates or oxetanes, can be used as monomers for the generation of corresponding oligomers, dendrimers or polymers. The oligomerisation or polymerisation here preferably takes place via the halogen functionality or the boronic acid functionality or via the polymerisable group. It is furthermore possible to crosslink the polymers via groups of this type. The compounds and polymers according to the invention can be employed as crosslinked or uncrosslinked layer.

The invention therefore furthermore relates to oligomers, polymers or dendrimers containing one or more of the compounds according to the invention indicated above, where one or more bonds from the compound according to the invention to the polymer, oligomer or dendrimer are present at one or more positions instead of substituents. Depending on the linking of the compound according to the invention, this forms a side chain of the oligomer or polymer or is linked in the main chain or forms the core of a dendrimer. The polymers, oligomers or dendrimers may be conjugated, partially conjugated or non-conjugated. The oligomers or polymers may be linear, branched or dendritic. The same preferences as described above apply to the recurring units of the compounds according to the invention in oligomers, dendrimers and polymers.

For the preparation of the oligomers or polymers, the monomers according to the invention are homopolymerised or copolymerised with further monomers. Preference is given to homopolymers or copolymers in which the units of the formula (I) or the preferred embodiments indicated above are present to the extent of 0.01 to 99.9 mol %, preferably 5 to 90 mol %, particularly preferably 20 to 80 mol %. Suitable and preferred comonomers which form the polymer backbone are selected from fluorenes (for example in accordance with EP 842208 or WO 2000/22026), spirobifluorenes (for example in accordance with EP 707020, EP 894107 or WO 2006/061181), para-phenylenes (for example in accordance with WO 92/18552), carbazoles (for example in accordance with WO 2004/070772 or WO 2004/113468), thiophenes (for example in accordance with EP 1028136), dihydrophenanthrenes (for example in accordance with WO 2005/014689), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers may also contain further units, for example electron-transport units. In addition, the polymers may contain triplet emitters, either copolymerised or mixed in as a blend. In particular, the combination of the oligomers, polymers or dendrimers according to the invention with triplet emitters leads to particularly good results.

In the following formulae detailing the features of the compound of Formula (I), Q represents the triazine pyrimidine subunit of Formula (I):

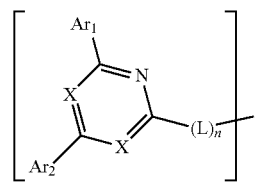

It is preferred that $Z_1$ and $Z_2$ groups in the 9-positions of the fluorene nucleus are, identically or differently, a straight-chain or branched alkyl group having 1 to 12 atoms, or an aromatic or heteroaromatic ring system having 5 to 40 aromatic ring atoms. More preferred are where $Z_1$ and $Z_2$ are, identically or differently, a straight-chain alkyl group having 1 to 6 atoms, or an aromatic ring system having 6 to 24 aromatic ring atoms. Particularly preferred examples of alkyl groups include methyl and ethyl. Particularly preferred examples of aromatic ring systems are phenyl, p-t-butylphenyl, p-(heteroaromatic)phenyl, m- or p-biphenyl or naphthyl. Of these, the most preferred are methyl or phenyl. While the $Z_1$ and $Z_2$ groups may be the same or different, it is more preferred that they are identical. Some specific examples of suitable $Z_1$ and $Z_2$ substituents on the fluorene nucleus of the compound of the invention include, but are not limited to:

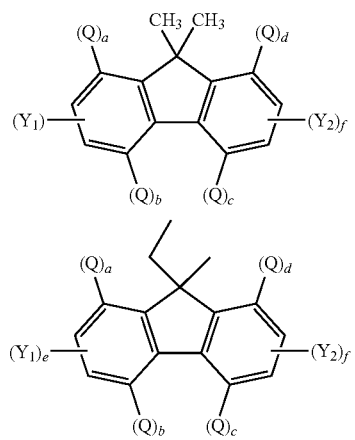

-continued

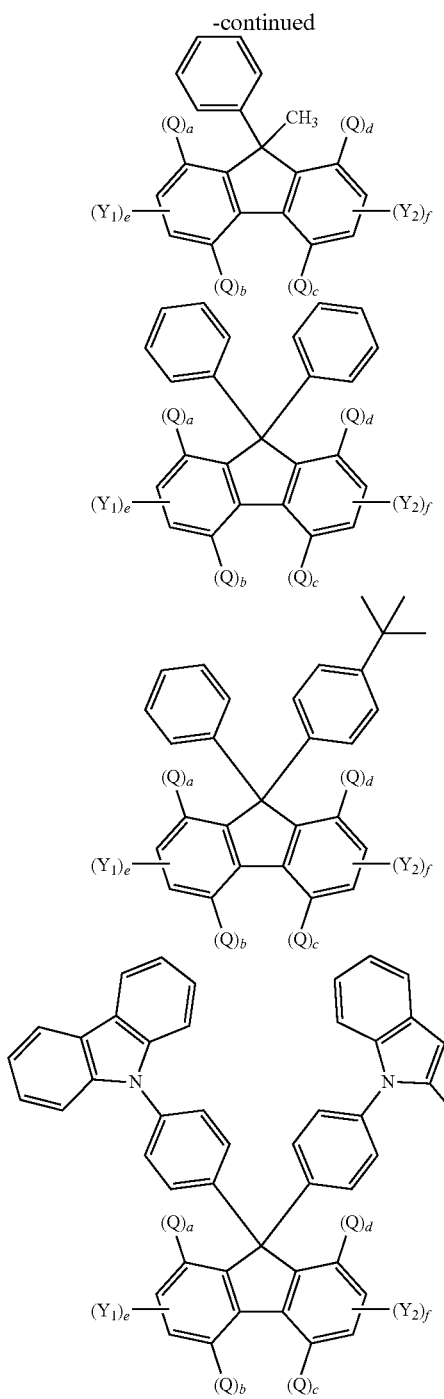

Y$_1$ and Y$_2$ represents substituents on the two different rings of the fluorene nucleus of the compound of the invention. It should be understood that whenever a, b, c or d is 0 (no Q group), those positions may or may not be occupied by a Y$_1$ or Y$_2$ group. Whenever e or f is 0, there are no Y$_1$ or Y$_2$ substituents on that ring and the open positions are H. This is most preferred. Whenever e or f is not zero, Y$_1$ and Y$_2$ are, identically or differently, preferred an aromatic or heteroaromatic ring system having 5 to 60 aromatic ring atoms. Some examples of preferred aromatic groups include substituted or unsubstituted phenyl, naphthyl, or anthracenyl each of which may be further substituted by one or more R$_1$ groups. Some examples of preferred heteroaromatic groups include N-arylcarbazoyls, benzimidazoles, dibenzofurans, dibenzothiophenes or fluorenes, including 9,9'-spirobifluorenes. Whenever e or f is 2, it is furthermore preferred that two adjacent Y$_1$ or Y$_2$ substituents form an annulated mono- or polycyclic, aliphatic or aromatic or heteroaromatic ring system with one another.

Some examples of suitable Y$_1$ and Y$_2$ substituents on the fluorene nucleus of the compound of the invention include, but are not limited to:

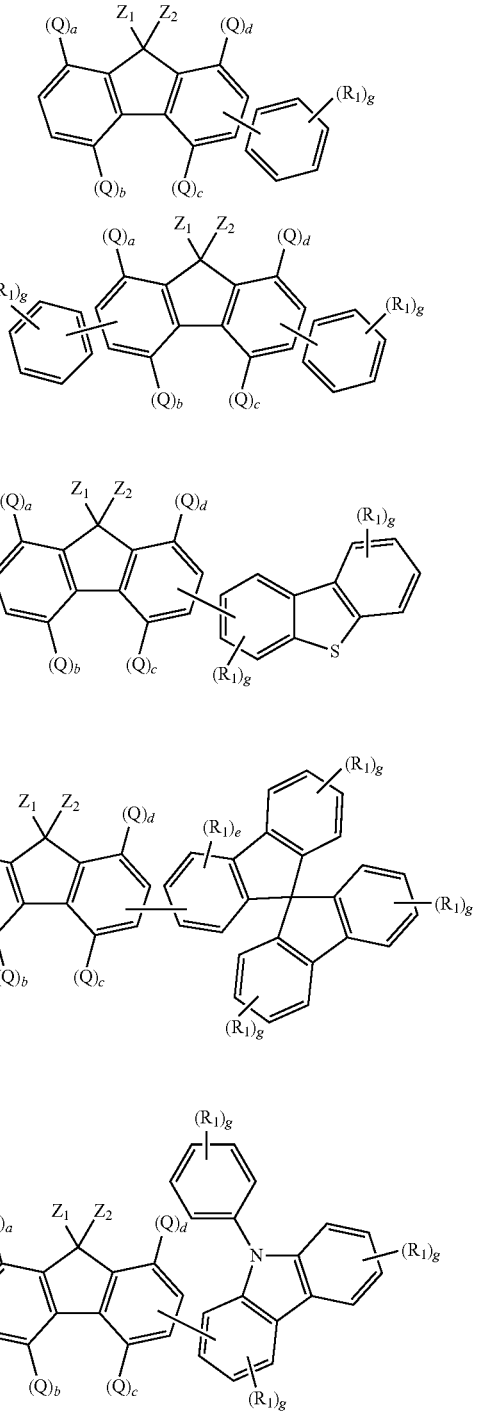

-continued

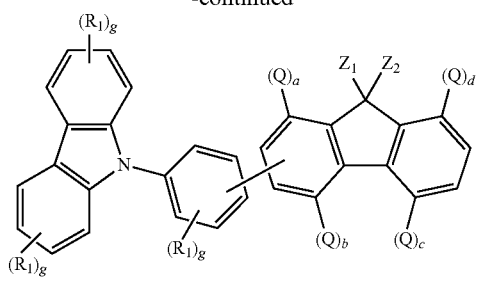
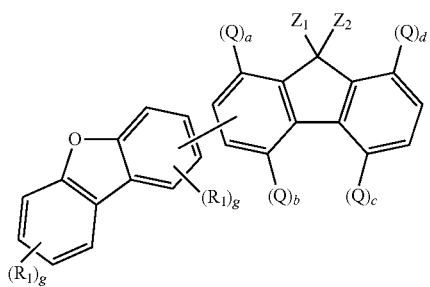
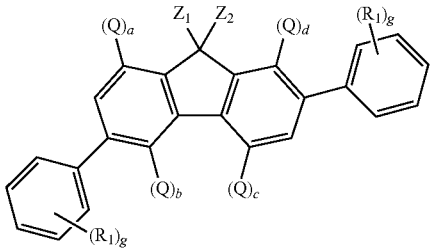
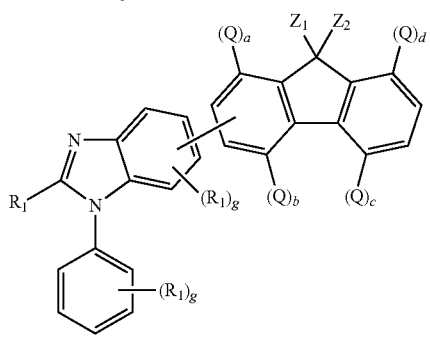
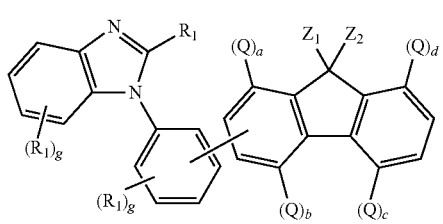

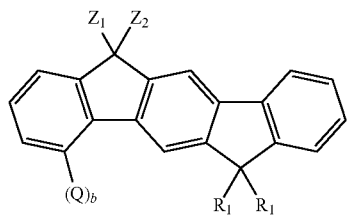
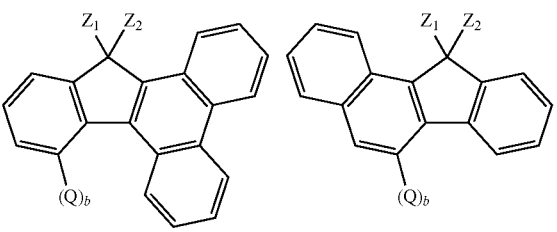
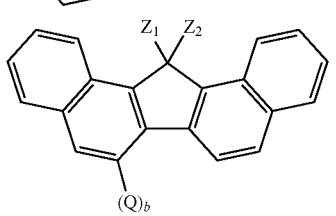
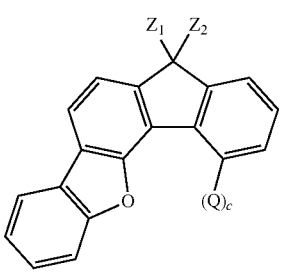
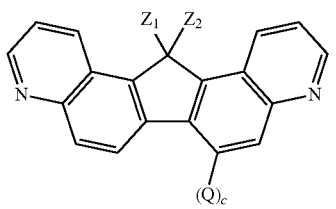
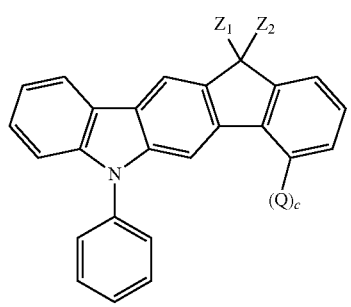

In the above structures, $R_1$ is as defined above and g may be independently 0, 1, 2, 3 or 4.

The following examples of suitable $Y_1$ and $Y_2$ which are adjacent and together form an annulated ring system are for where only one of a, b, c and d is 1 and the others are 0 in a compound of Formula (I). It is understood that these illustrative examples are not limiting and analogous examples are also possible where a, b, c or d is 0 or 1 in any combination.

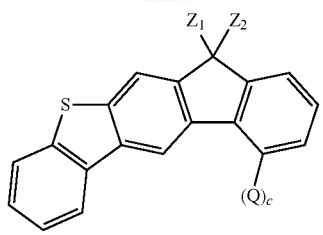

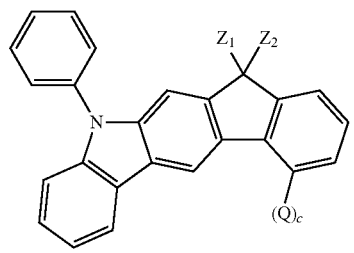

In the compound of the invention, the fluorene nucleus is substituted by one to four Q groups in the 1-, 1'-, 4-, 4'-positions in any combination. It is preferred that only one of a or b is 1 while only one of c or d is 1. It is even more preferred if b is 1 (a is 0) while either c or d is 1. It is still even more preferred that only one of a or b is 1 while c and d are both 0. It is most preferred that only b is 1 while a, c and d are 0.

L is a linking group that connects (directly or indirectly) a carbon atom in a triazine or pyrimidine group to the fluorene nucleus. When n is 0, there is no linking group and the carbon atom of the triazine or pyrimidine group is directly attached to the fluorene nucleus by a single bond in the 1-, 1'-, 4- or 4'-position. For example, if a, b, c and d each is 1 and the corresponding n is 0 for each, then the compound of Formula (I) would be:

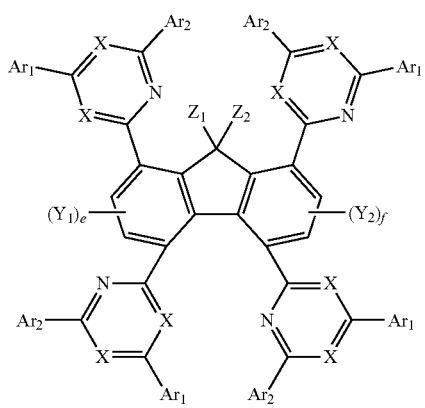

It is understood that n can be the same or different for each Q group. For example, in the case where both b and d are 1 (a and c are 0), the corresponding n can be 0 and 1 as shown below:

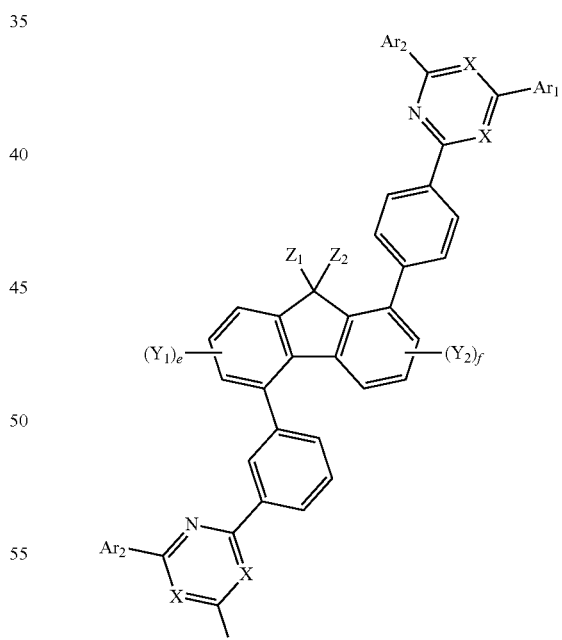

When n is 1, L is a linking group that indirectly connects a carbon atom in a triazine or pyrimidine group to any of the 1-, 1'-, 4- or 4'-positions of the fluorene nucleus through at least one other atom that isn't part of either the triazine/pyrimidine group or the fluorene nucleus. The connections of triazine/pyrimidine to L as well as L to the fluorene nucleus are both via single bonds. Preferably, L is on each occurrence, identically or differently, an aromatic ring system having 6-30 aromatic ring atoms which may be further substituted. Some examples of preferred L groups are phenyl, biphenyl or anthracenyl. Of these, phenyl is most preferred, desirably via the 1,4- or 1,3-position of the phenyl. It is understood that L can be the same or different for each Q group; for example, in the following compound where b and d are 1 (a and c are 0), the corresponding L groups are different:

It is most preferred that n is 0.

In Formula (I), at least one X stands for N on each occurrence, identically or differently. In the sense of the invention, that means that for each Q group, at least one X is N in each heteroaromatic ring. When both X in a single ring are N, which is preferred, the Q group is a 2,4-disubstituted 1,3,5-triazine (triazinyl group):

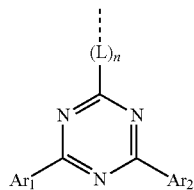

When only one X is N and the other X is CR$_1$, the Q group is a 2,4-disubstituted 1,5- or 1,3-pyrimidine (pyrimidinyl) group:

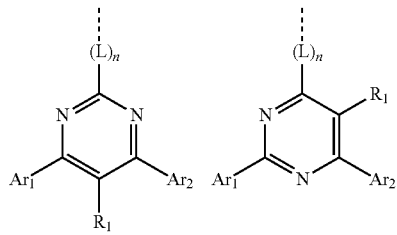

In either of these pyrimidine groups, it is preferred that the radicals R$_1$ which are present on X do not form a ring with any adjacent substituents (Ar$_1$, Ar$_2$, L or if n is 0, the fluorene nucleus or any Y substituents). In particular, it is preferred that the triazinyl or pyrimidinyl group is a single ring system and has no annulated rings. It is most preferred that R$_1$ is H.

It is understood that the choice of X is independent within each Q group. That is, a compound of Formula (I) may have 1 to 4 triazinyl groups, 1 to 4 pyrimidinyl groups or 1 to 4 groups in any combination of the two. For example, the following compounds of Formula (I) where b and d are both 1 and a and c are both 0 and n is 0 for both Q groups illustrate that the Q may be the same or mixed:

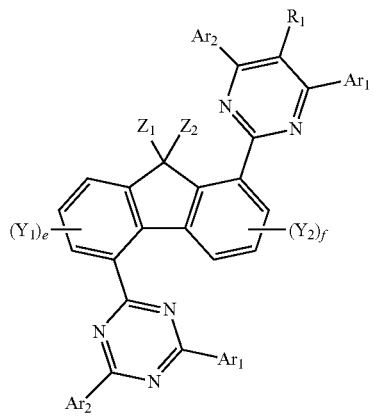

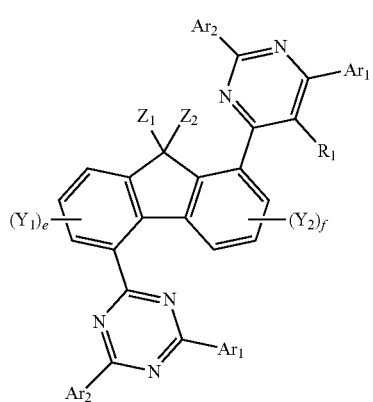

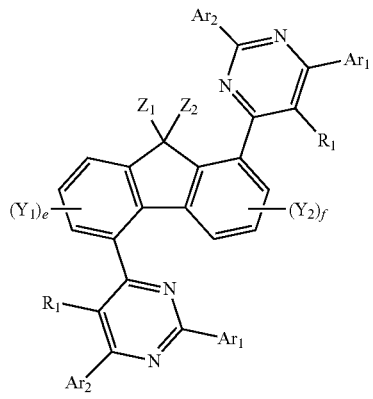

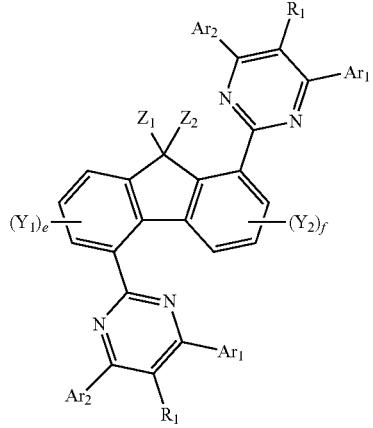

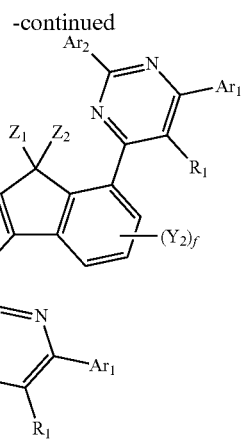

The above illustrative examples are not limiting and analogous examples are also possible where the groups at the 4- and 1'-positions are interchanged, or are located in the 1- and 4'-, 1- and 4-, 1'- and 4'-positions. Similar examples with 3 or 4 Q groups consisting of the same or a mixture of triazinyl or pyrimidinyl groups in any combination are also envisioned.

In the context of the triazinyl or pyrimidinyl groups Q, preferred groups $Ar_1$ and $Ar_2$ are identical or independently aromatic or heteroaromatic ring systems having 5 to 23 aromatic ring atoms, which may in each case be substituted by one or more radicals $R_1$. The total of aromatic ring atoms (carbon or heteroatom) is the sum of all individual aromatic ring atoms (which includes for this purpose all $sp^2$ hybridized carbon atoms and divalent and trivalent heteroatoms when the heteroatoms are attached to at least two different $sp^2$ carbon atoms but excludes non-aromatic tetrahedral carbon and nitrogen atoms) within all aromatic groups in the substituent including $R_1$ if present. For example, suitable groups for $Ar_1$ and $Ar_2$ (with their aromatic ring atoms total) include benzene (6), ortho-, meta- or para-biphenyl (12), ortho-, meta-, para- or branched terphenyl (18), 1-, 2-, 3- or 4-9,9-dialkylfluorenyl (12), 1- or 2-naphthyl (10), pyrrole (5), furan (5), thiophene (5), indole (9), benzofuran (9), benzothiophene (9), 1-, 2- or 3-N-alkylcarbazole (13), 1-, 2- or 3-N-phenylcarbazole (19) which also be attached through the N-phenyl group, 1-, 2- or 3-dibenzofuran (13), 1-, 2- or 3-dibenzothiophene (13), indenocarbazole (19), indolocarbazole (20), 2-, 3- or 4-pyridine (6), 2-, 4- or 5-pyrimidine (6), pyrazine (6), pyridazine (6), triazine (6), anthracene (14), phenanthrene (14), triphenylene (18), pyrene (16), benzanthracene (18), N-phenylphenanthridinone (20) or combinations of two or three of these groups, each of which may be substituted by one or more radicals $R_1$, so long as there is no more than 23 aromatic ring atoms in total. Some examples of non-inventive substituents with more than 23 aromatic ring atoms are quaterphenyl (24), 9,9-diphenylfluorene (24) and 9,9'-spirobifluorene (24). $Ar_1$ and $Ar_2$ particularly is selected from the group consisting of benzene, ortho-, meta- or para-biphenyl, ortho-, meta-, para- or branched terphenyl, naphthyl, triphenylene, 9,9-dialkylfluorenyl or derivatives, N-phenylcarbazole, dibenzofuran and dibenzothiophene. It should be understood that this preferred group includes not only the basic unsubstituted structures but also includes derivatives thereof, such as those substituted with further $R_1$ substituents. In particular, 9,9-dialkylfluorenyl, N-phenylcarbazole, dibenzofuran and dibenzothiophene derivatives can have annulated rings or be connected through a linking phenyl group to Q so long as there are 23 or less aromatic ring atoms in the entire substituent including any aromatic ring atoms in $R_1$. It is preferred that any $R_1$ substituents on $Ar_1$ and $Ar_2$ are non-aromatic. $Ar_1$ and $Ar_2$ are connected to the triazinyl or pyrimidinyl groups via one single bond and do not form a ring system or have any other connection to the triazinyl or pyrimidinyl groups. Moreover, $Ar_1$ and $Ar_2$ are different from the linking group L; that is, the triazinyl or pyrimidinyl group is not connected to the fluorene through $Ar_1$ or $Ar_2$. In a preferred embodiment of the invention, $Ar_1$ and $Ar_2$ are identical.

In a further preferred embodiment of the invention, the aromatic groups in the groups $Ar_1$ and $Ar_2$, if either contains more than one aryl group, are not para-linked, i.e. they are preferably not para-biphenyl or para-terphenyl, but instead, for example, the respective ortho- or meta-linked structures.

However, if $Ar_1$ or $Ar_2$ (or both) is or contains a nitrogen containing heteroaromatic group such as a carbazole, pyrrole, imidazole or benzimidazole group, the heteroaromatic group is not to be linked via a nitrogen atom directly to the triazine or pyrimidine nucleus, but instead via a carbon atom of the heteroaromatic group to a carbon atom in the triazine or pyrimidine. For example, if $Ar_1$ or $Ar_2$ is a N-phenylcarbazole group, it can be connected to the triazine or pyrimidine nucleus via a carbon atom of the carbazole or a carbon atom of the N-phenyl group (as shown in the examples below) but if $Ar_1$ or $Ar_2$ is a carbazole group, it should not be connected to the triazine or pyrimidine nucleus directly by the nitrogen atom of the carbazole group.

Some non-limiting examples of $Ar_1$ and $Ar_2$ include:

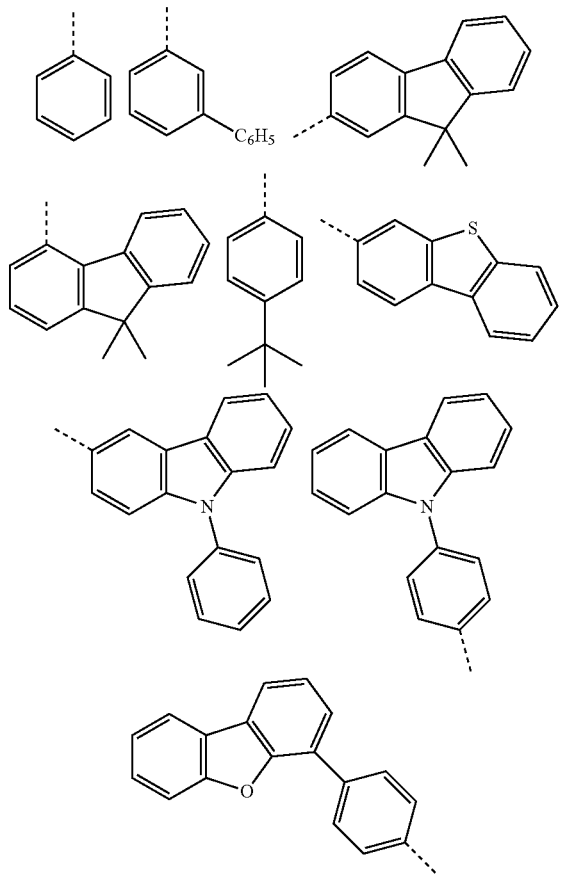

As noted above, it is preferred that in the compound of Formula (I), that $Z_1$ and $Z_2$ are identical. This corresponds to Formula II:

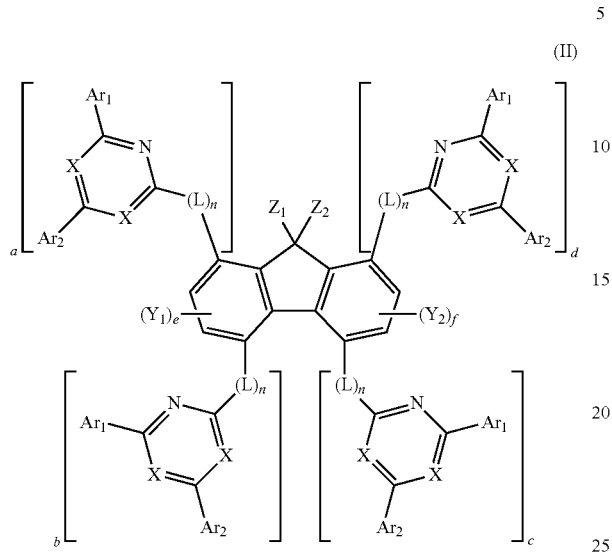

(II)

As noted above, it is preferred that in the compound of Formula (I), e or f are both 0 so that there are no $Y_1$ or $Y_2$ substituents and the open positions are H. This corresponds to Formula (III):

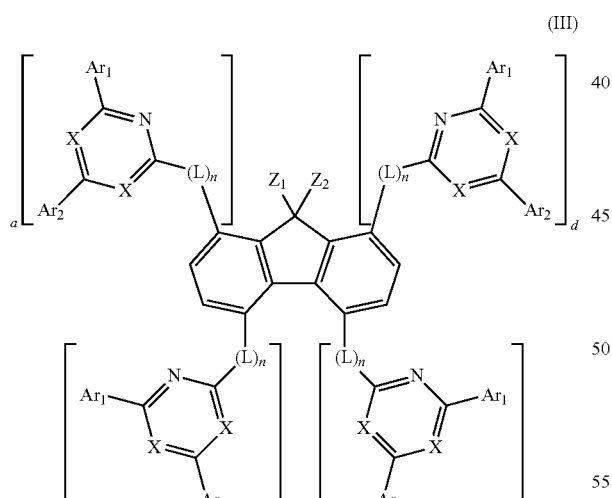

(III)

As noted above, in the compound of Formula (I), it is preferred that only one of a or b is 1 while only one of c or d is 1. These correspond to Formulae (IV) and (V):

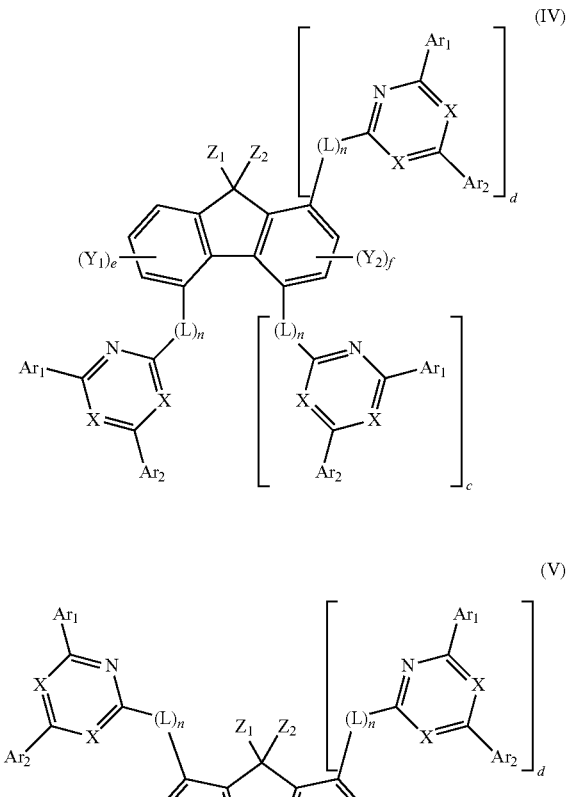

(IV)

(V)

As noted above, it is preferred that in the compound of Formula (I) that b is 1, a is 0 while either c or d is 1 and the other is 0. This corresponds to Formulae (VI) and (VII):

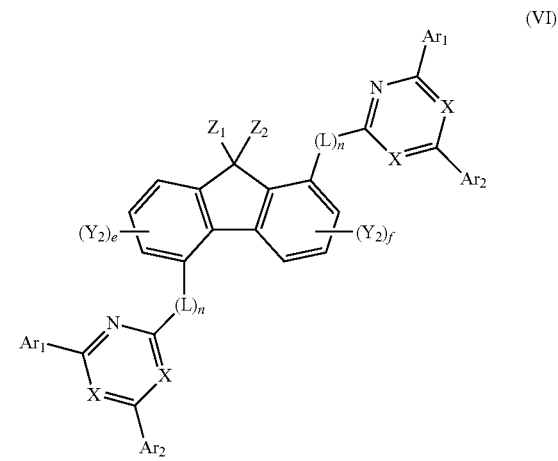

(VI)

(VII)

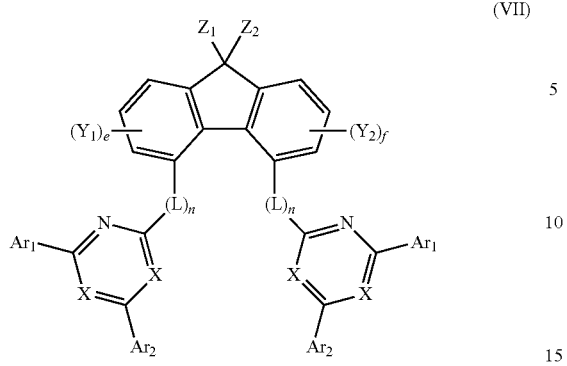

(IX)

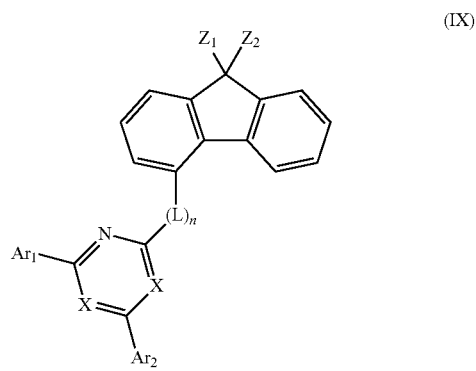

As noted above, it is preferred that in the compound of Formula (I) that b is 1 while a, c and d are 0. This corresponds to Formula (VIIIa):

(VIIIa)

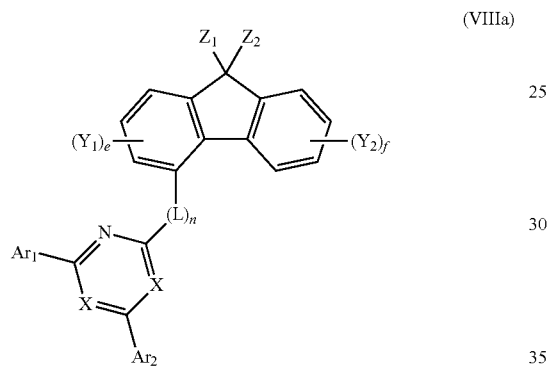

(X)

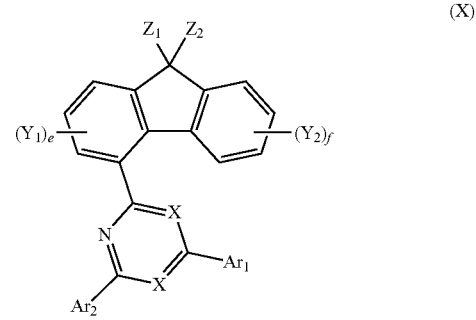

(XI)

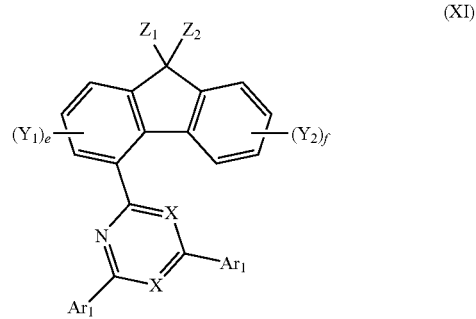

Alternatively, it is also preferred in the compound of Formula (I) that a is 1 while b, c and d are 0. This corresponds to Formula (VIIIb):

(VIIIb)

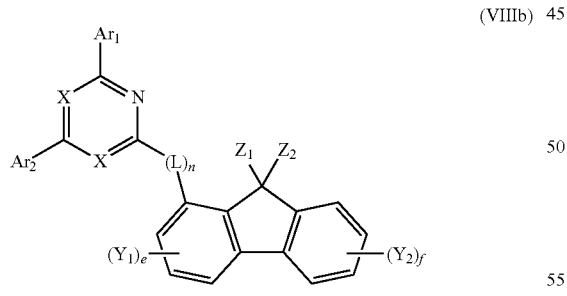

The preferred embodiments mentioned above can be combined with one another as desired. In a particularly preferred embodiment of the invention, the preferences mentioned above occur simultaneously. For example, the following formulae (IX) to (XVII) include some preferred combinations of features where Q is located in the 4-position:

(XII)

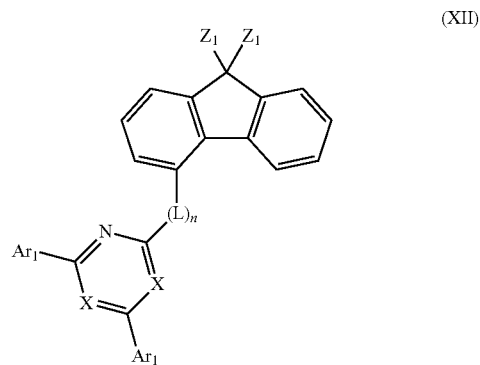

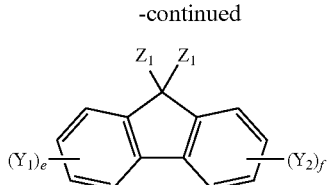
(XIII)

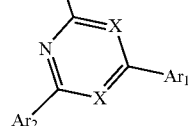
(XIV)

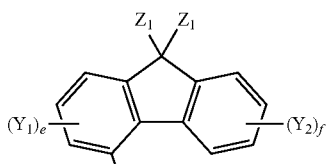
(XV)

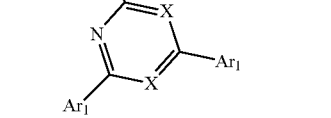
(XVI)

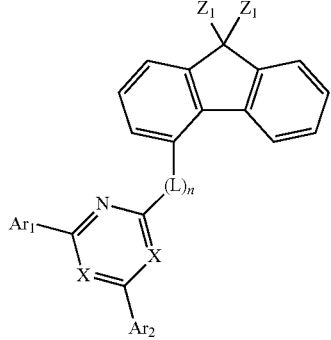
(XVII)

Also envisioned are the analogous compounds of Formulas (IX) to (XVII) where 0 is located in the 1-position instead of the 4-position. Of these, the most preferred are Formulae XII, XV, XVI and XVII where both X are nitrogen to form a triazine group (or the corresponding compounds where the triazine group is in the 1-position).

The following examples represent some compounds according to Formula

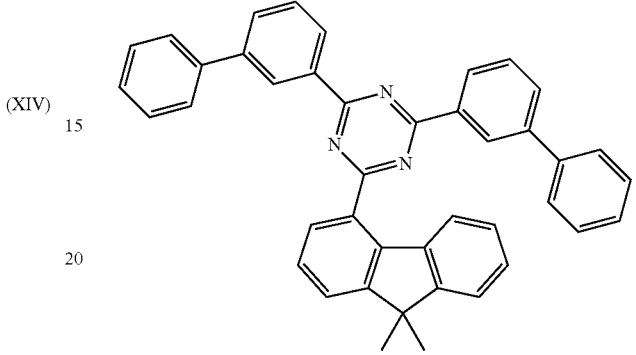
(1)

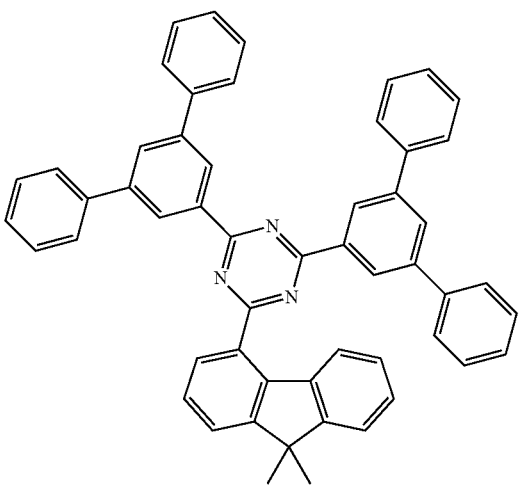
(2)

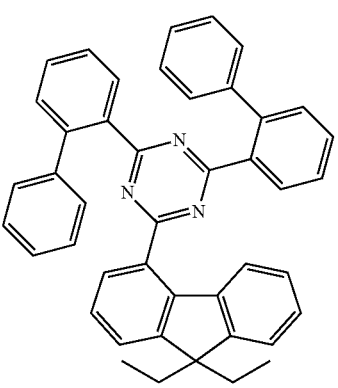
(3)

(4)
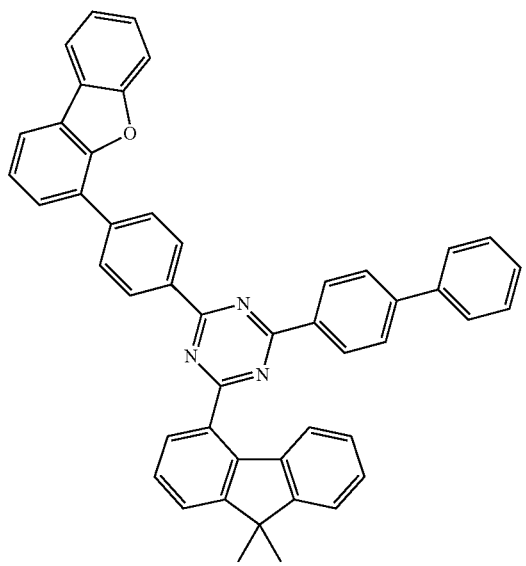
(5)
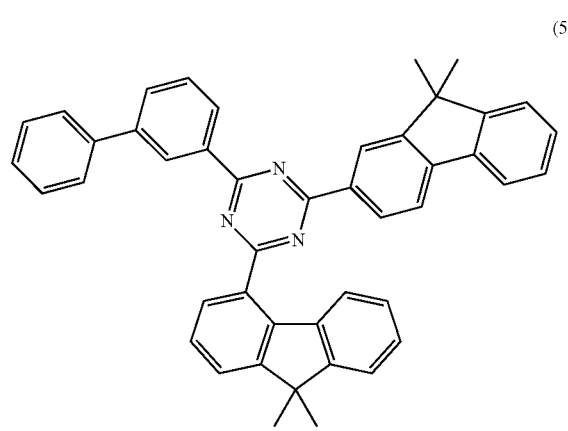
(6)
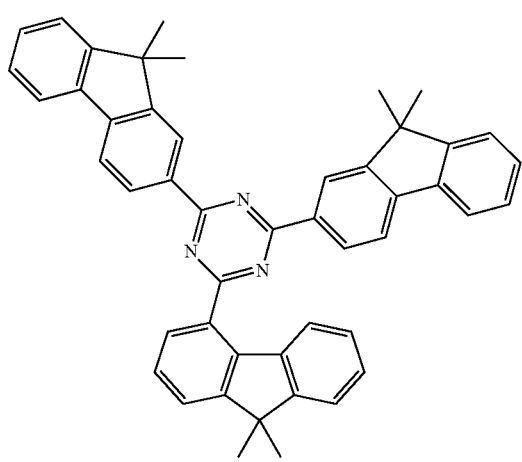
(7)
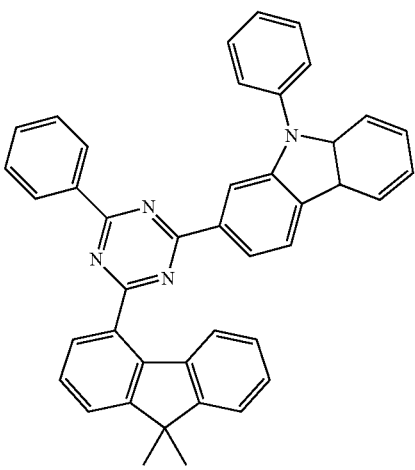
(8)
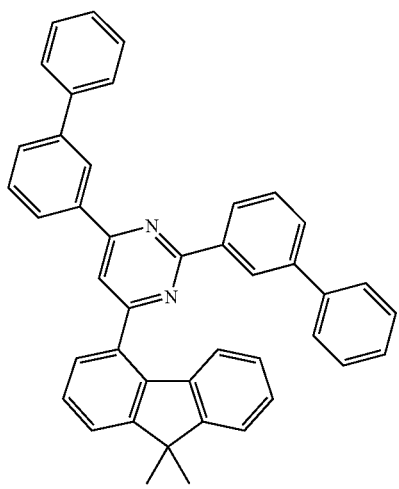
(9)
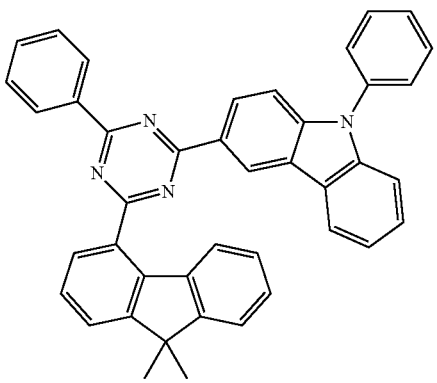

(10)
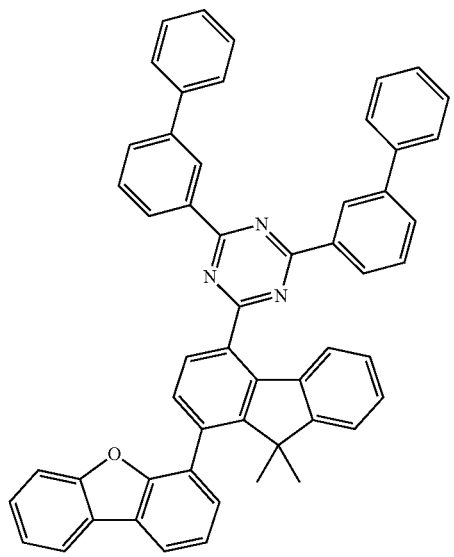
(11)
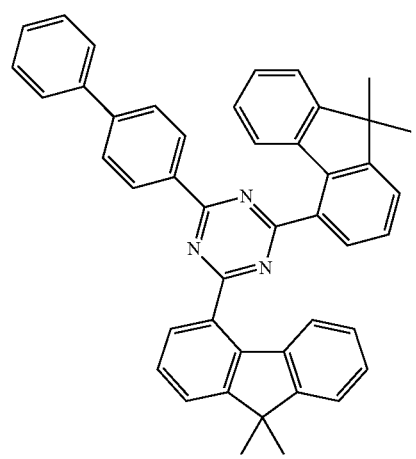
(12)
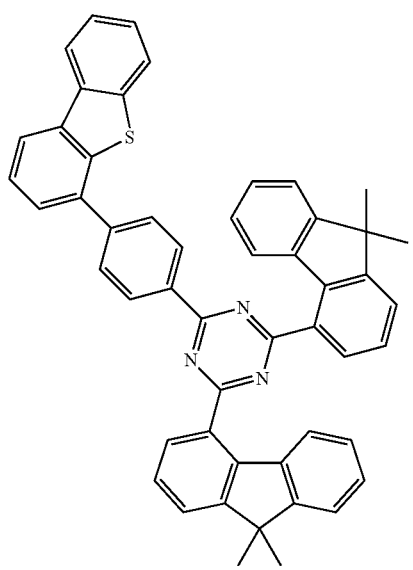
(13)
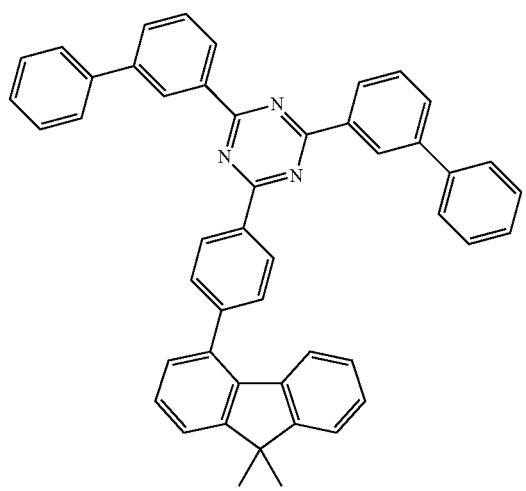
(14)
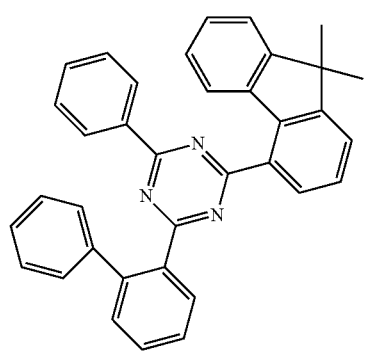
(15)
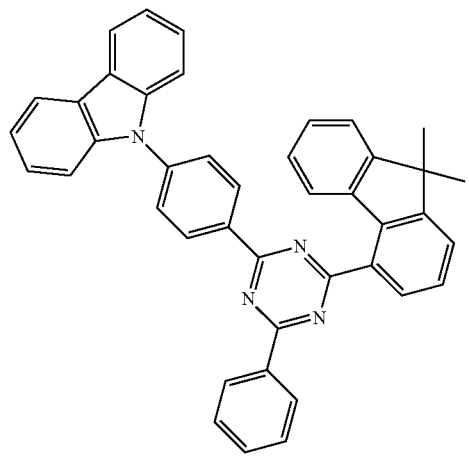

(16)
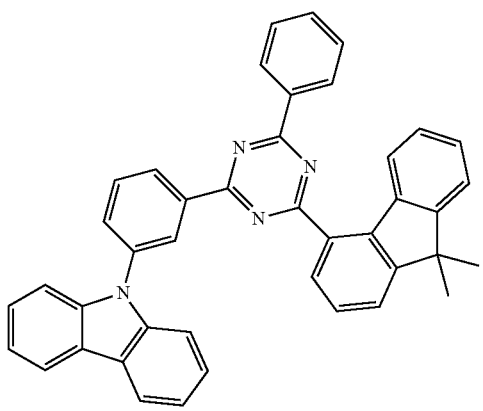
(17)
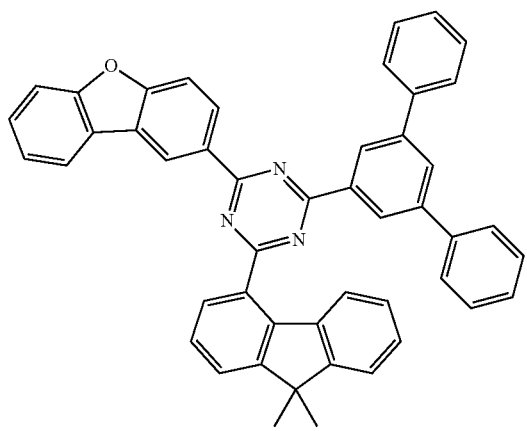
(18)
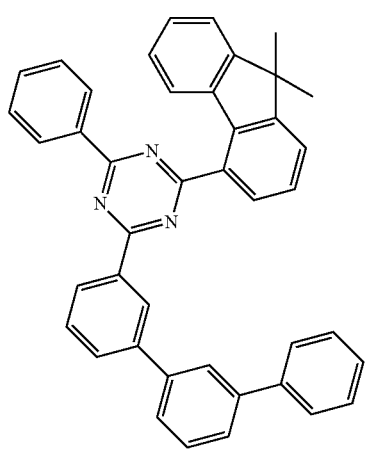
(19)
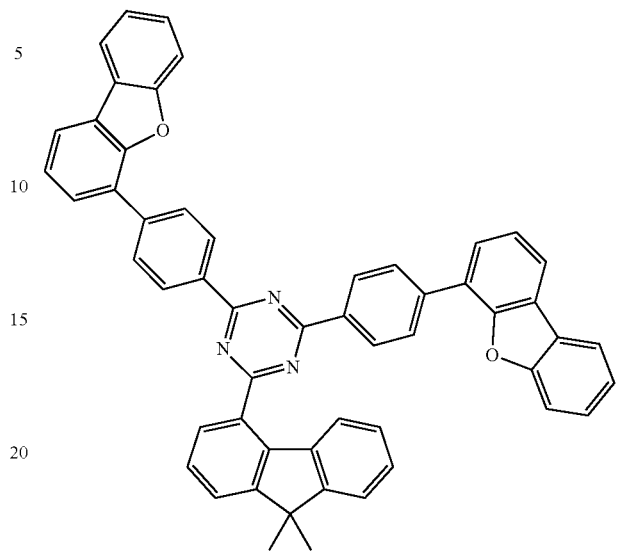
(20)
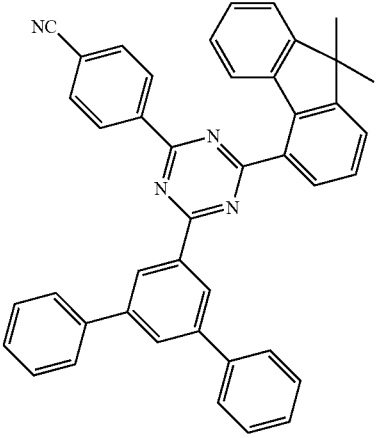
(21)
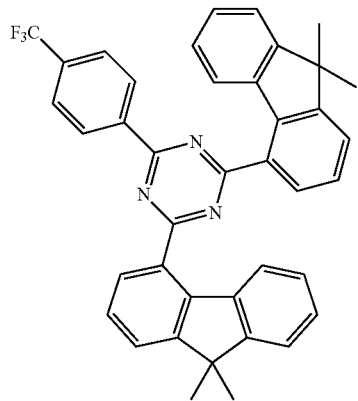

-continued
(22)
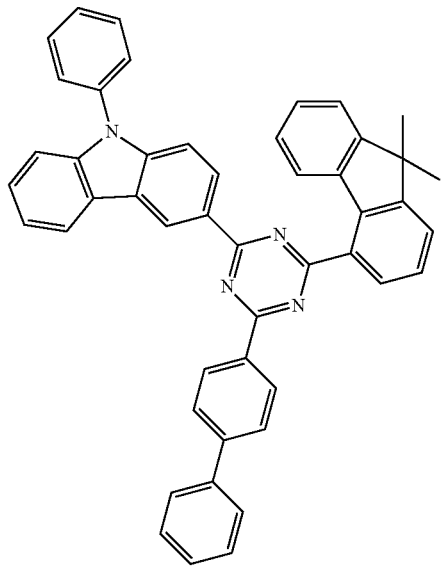
(23)
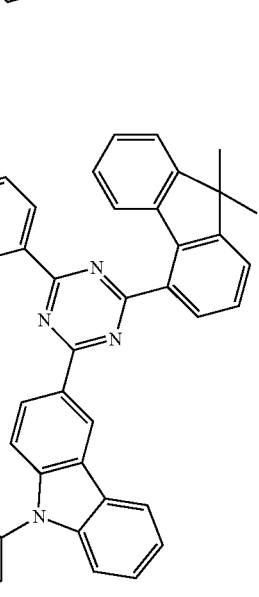
(24)
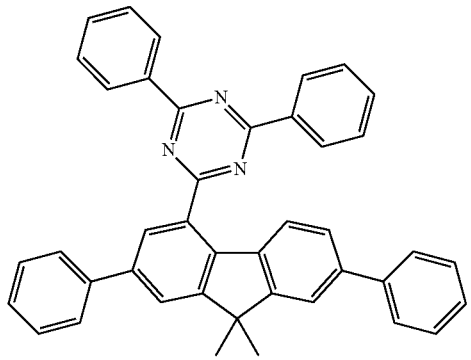
-continued
(25)
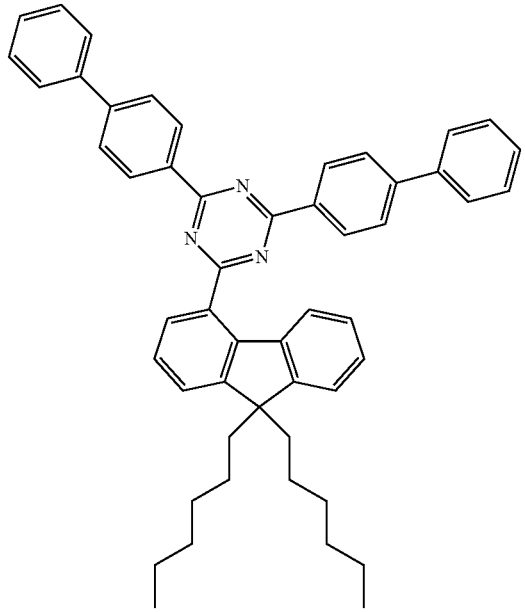
(26)
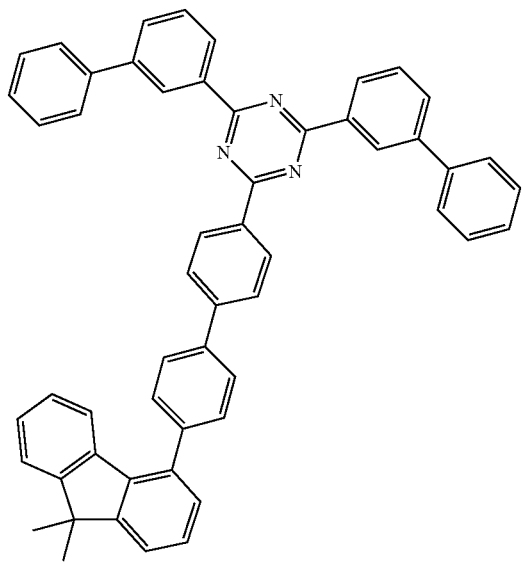
(27)

(28)
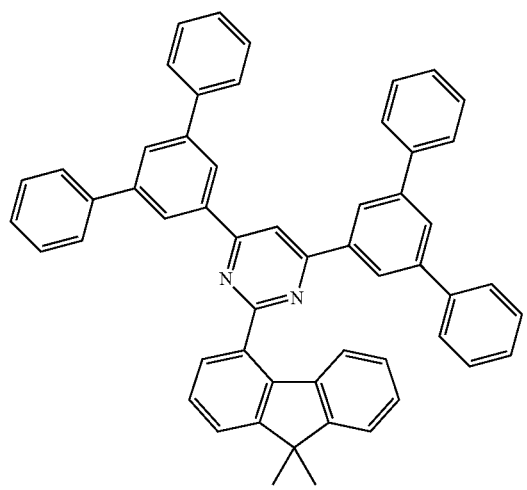
(29)
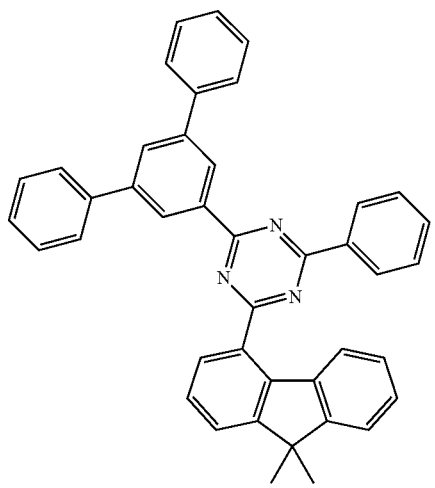
(30)
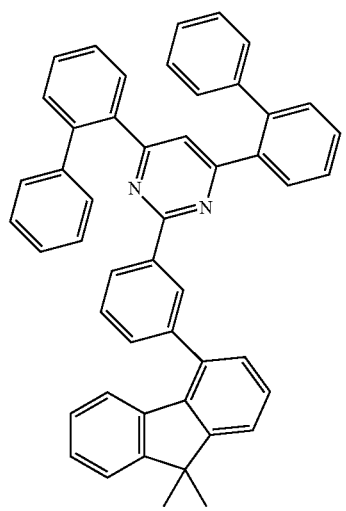
(31)
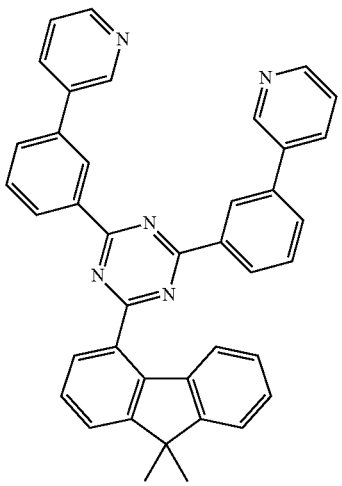
(32)
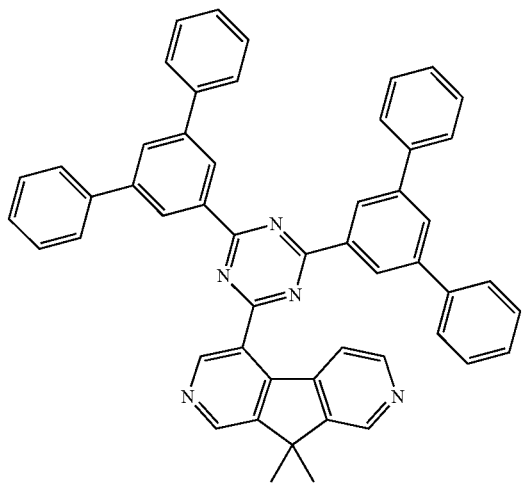
(33)
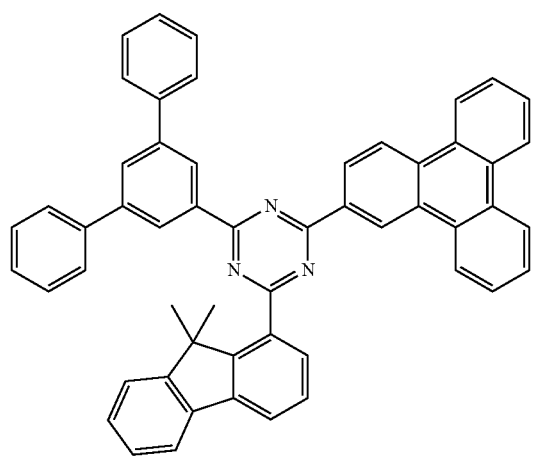

(34)
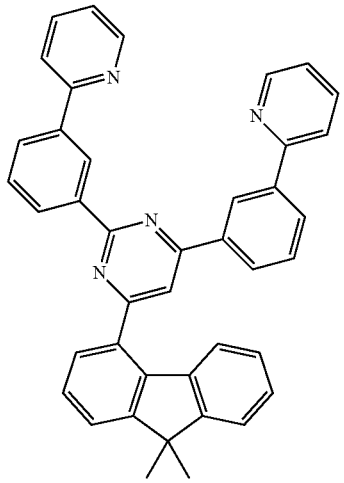
(35)
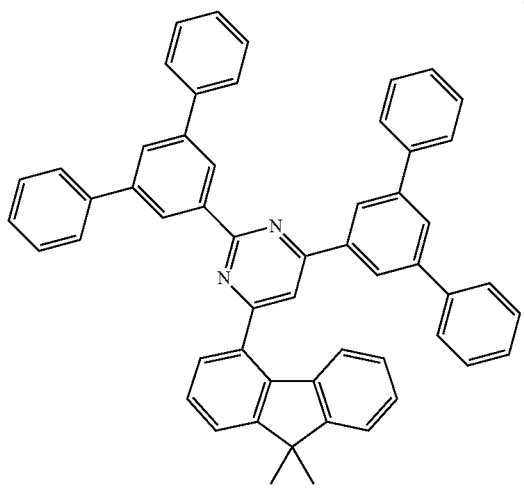
(36)
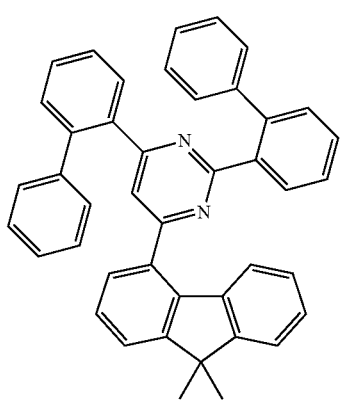
(37)
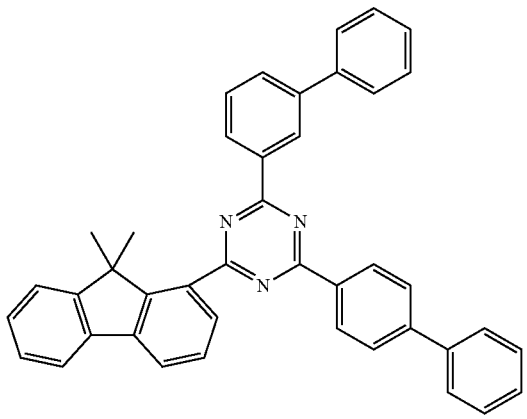
(38)
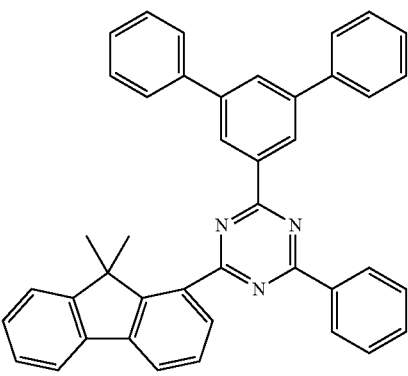
(39)
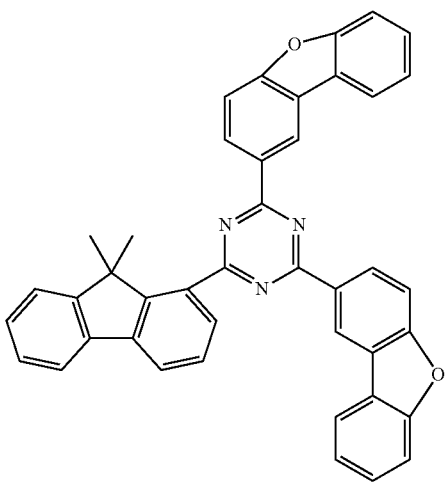

(40)
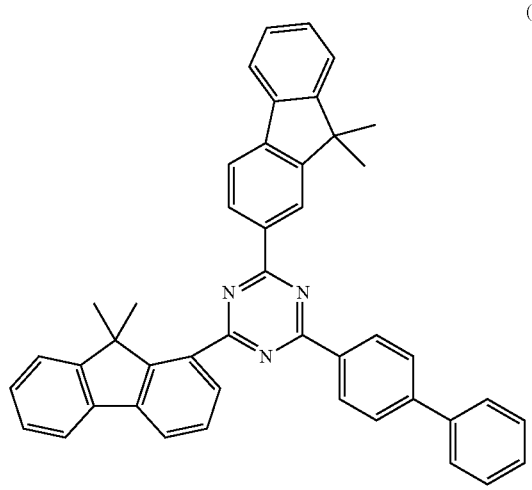
(41)
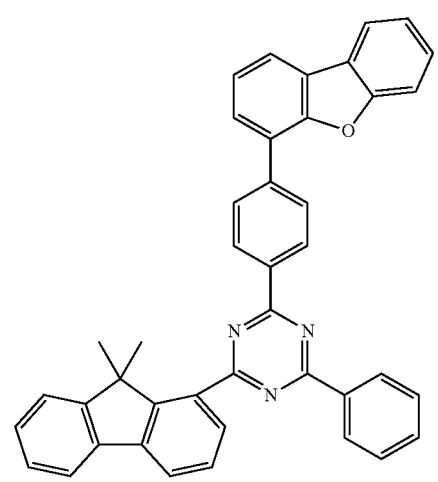
(42)
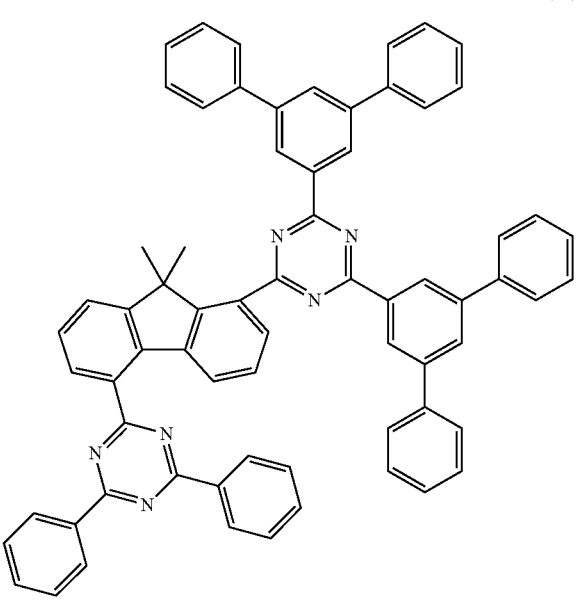
(43)
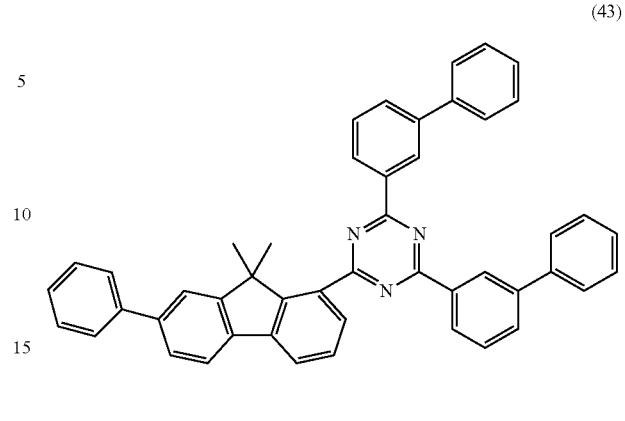
(44)
(45)
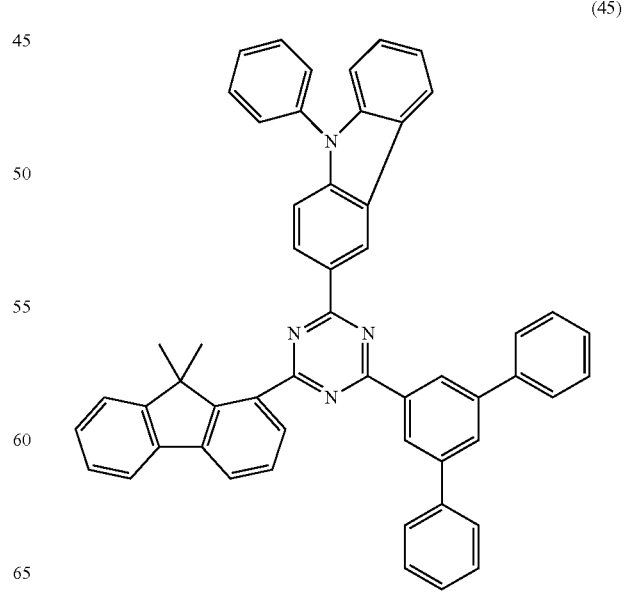

-continued
(46)
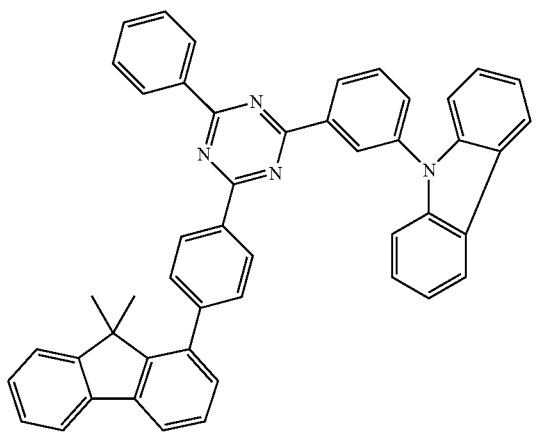
(47)
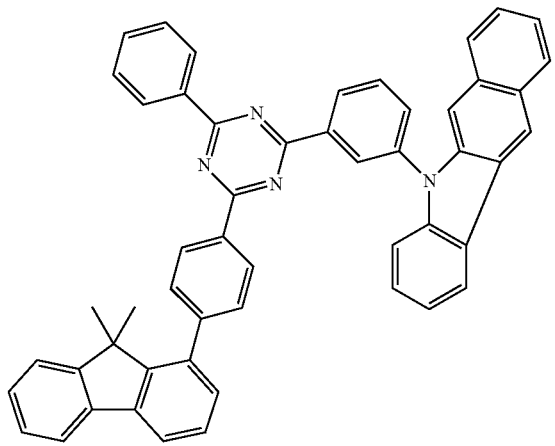
(48)
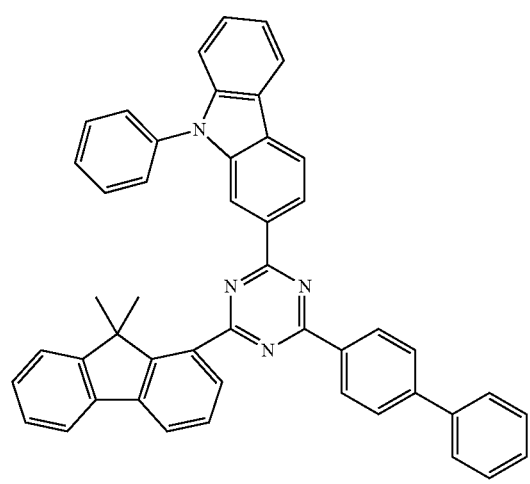
-continued
(49)
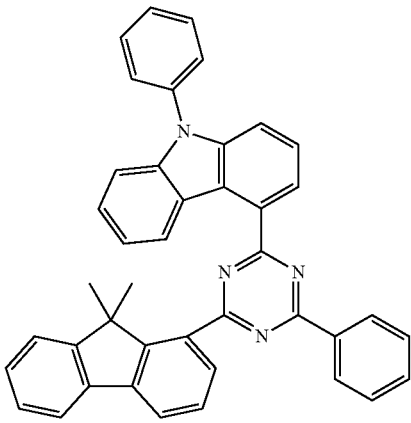
(50)
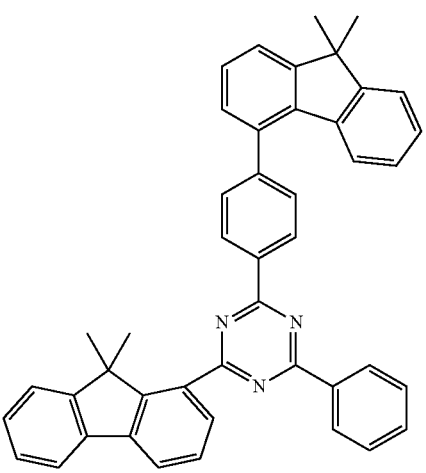
(51)
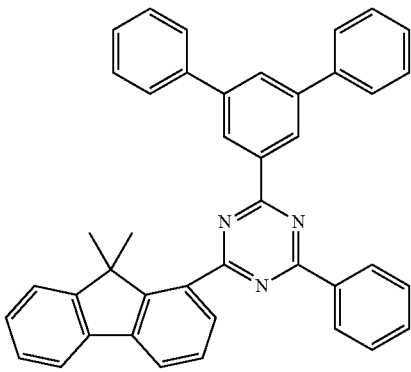

(52)
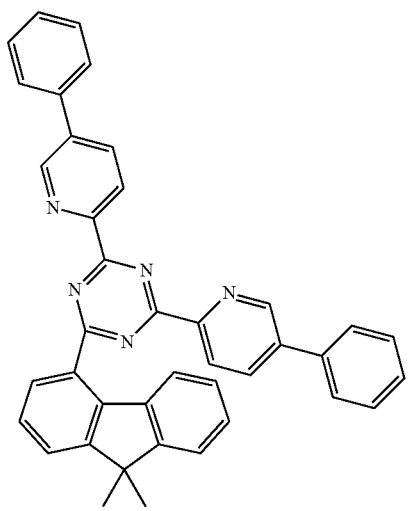
(53)
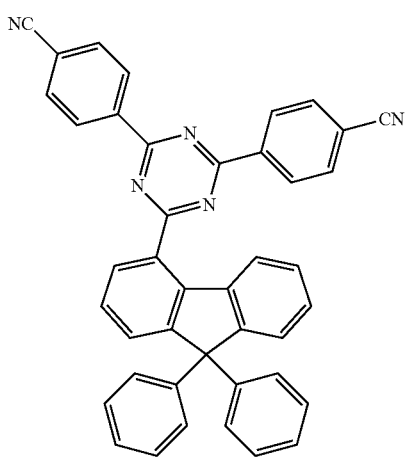
(54)
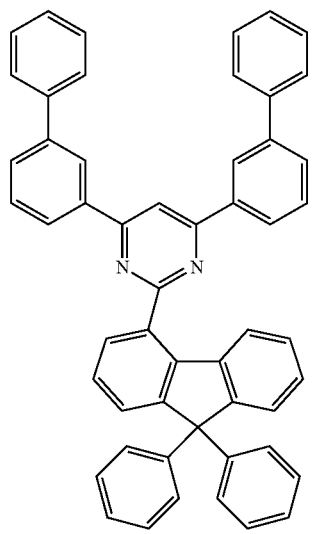
(55)
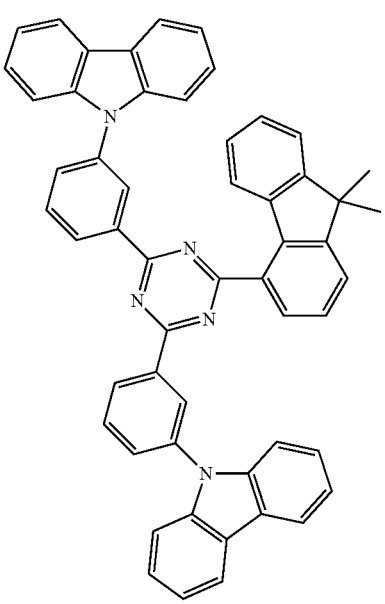
(57)
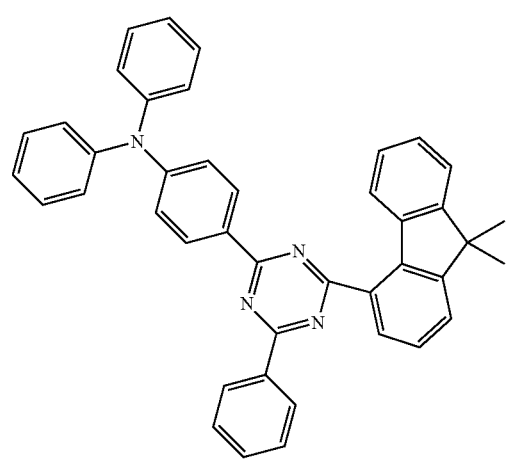
(58)
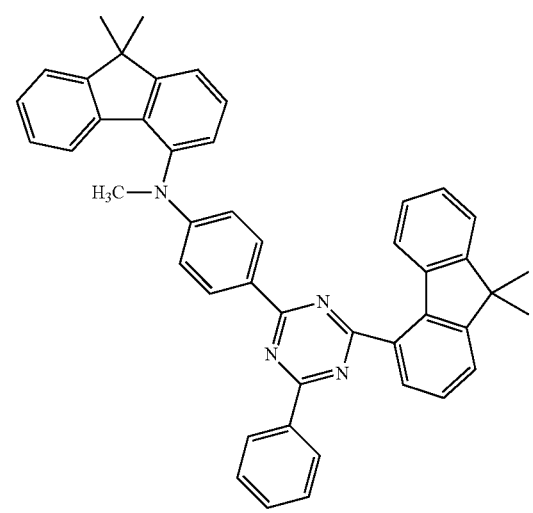

(59)
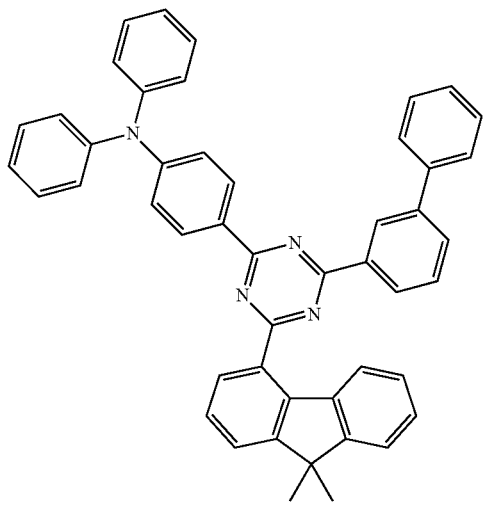
(62)
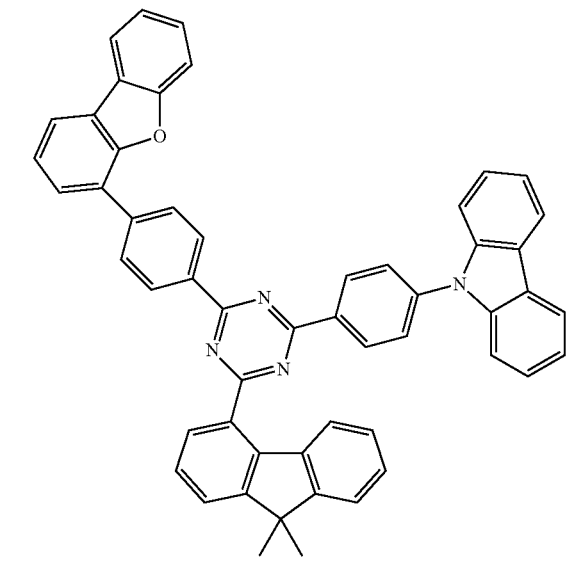
(60)
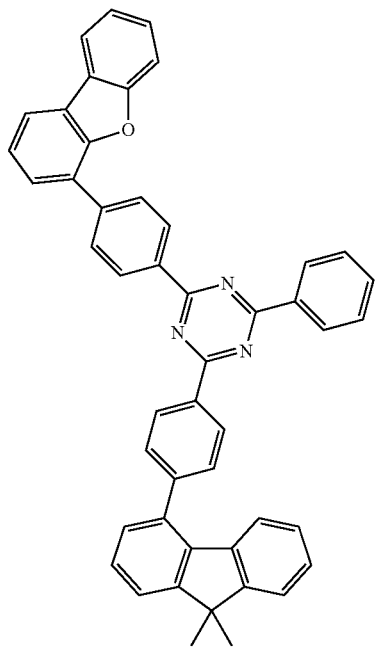
(63)
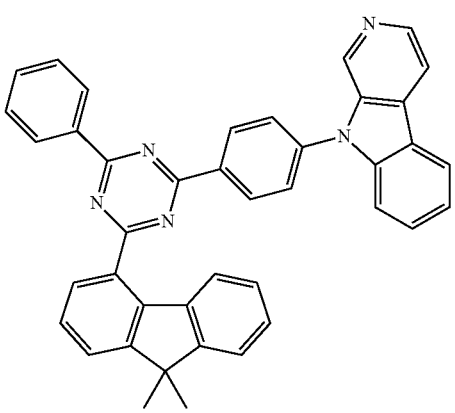
(61)
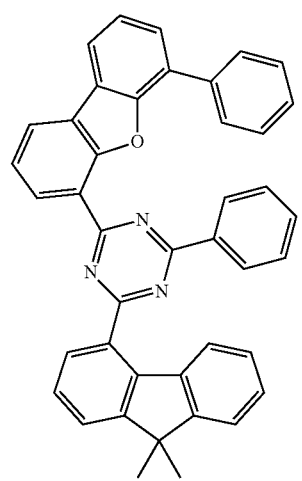
(64)
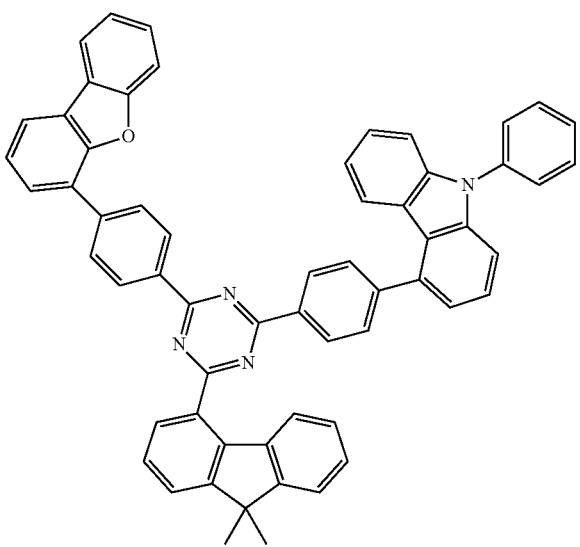

(65)
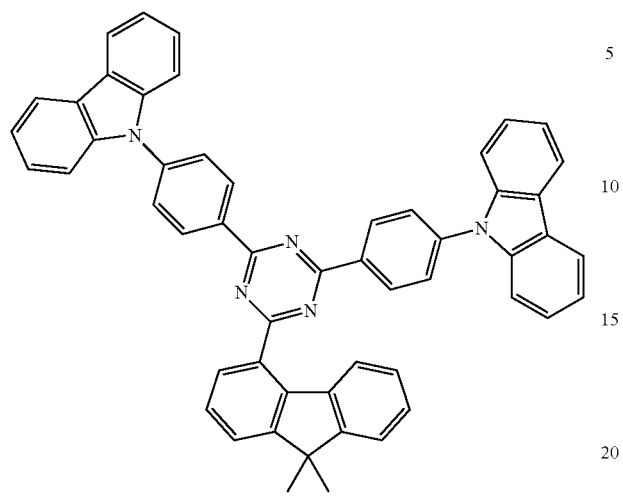
(66)
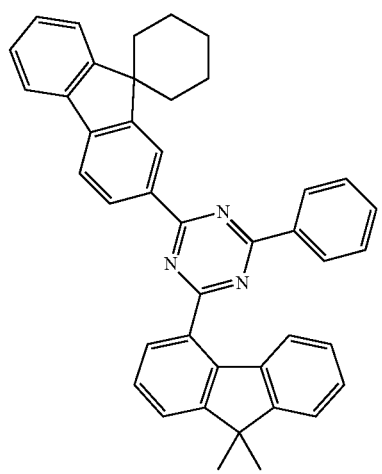
(67)
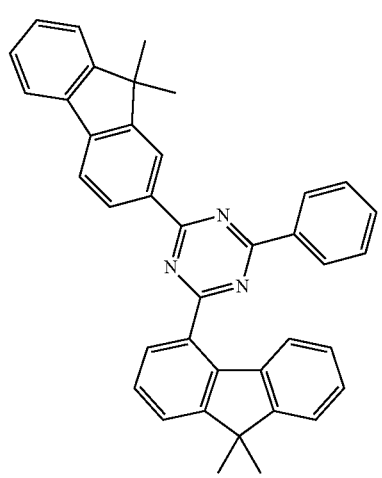
(68)
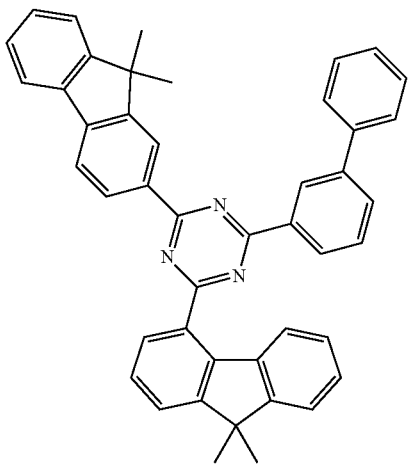
(69)
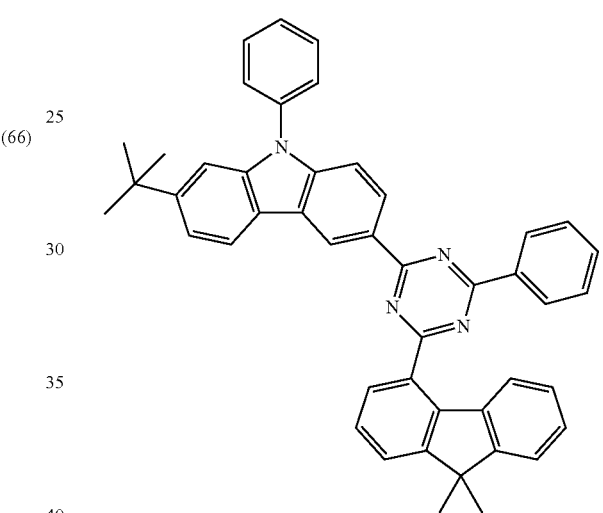
(70)
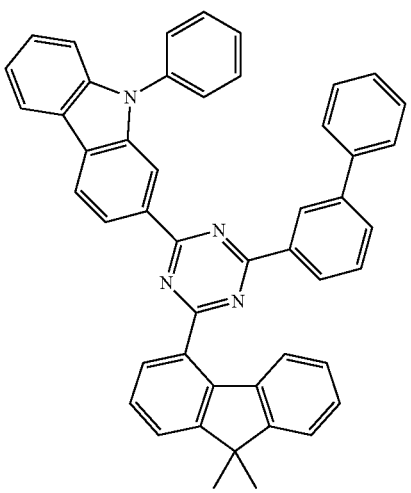

(71)
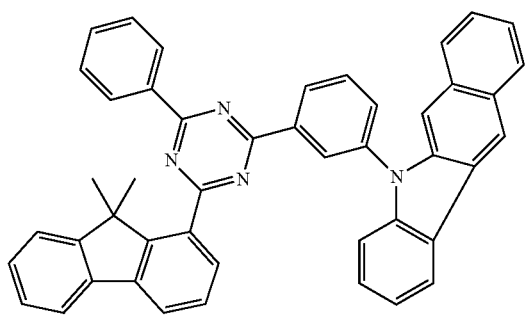
(72)
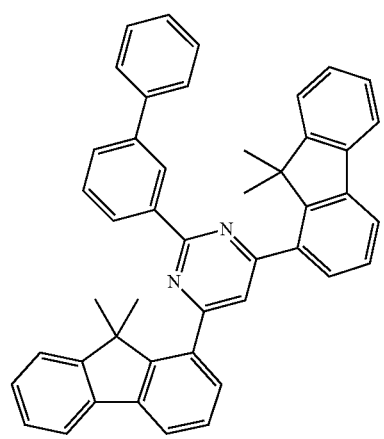
(73)
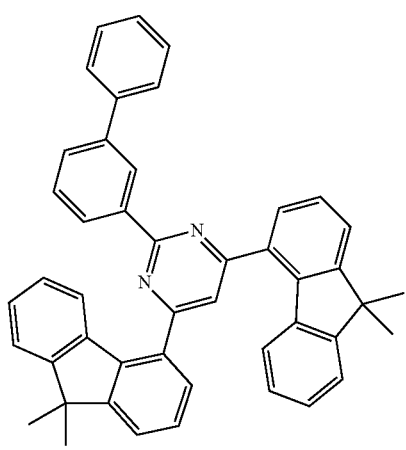
(74)
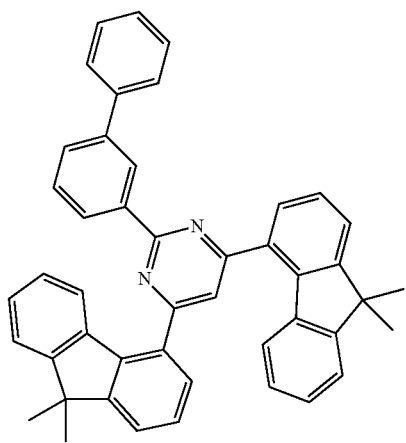
(75)
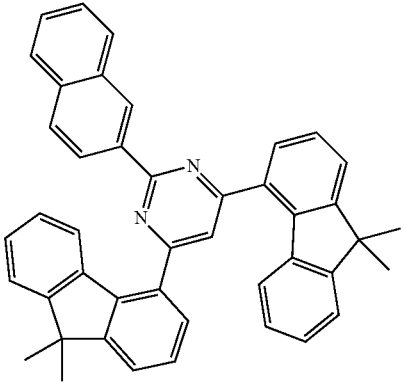
(76)
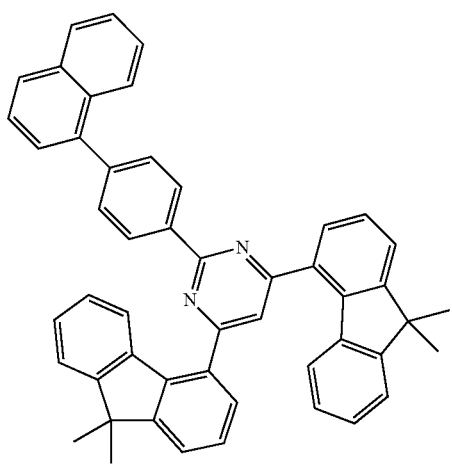
(77)
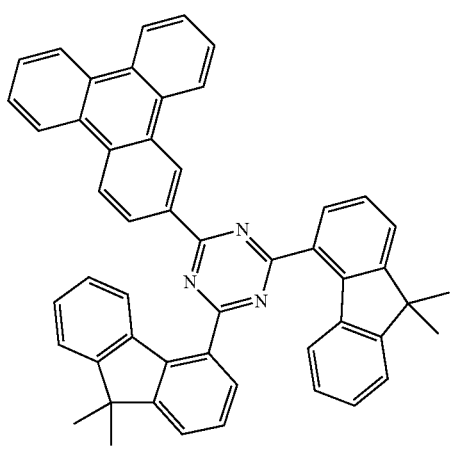

-continued
(78)
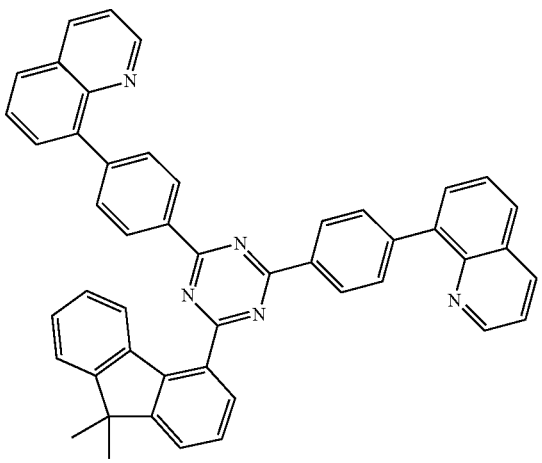
(79)
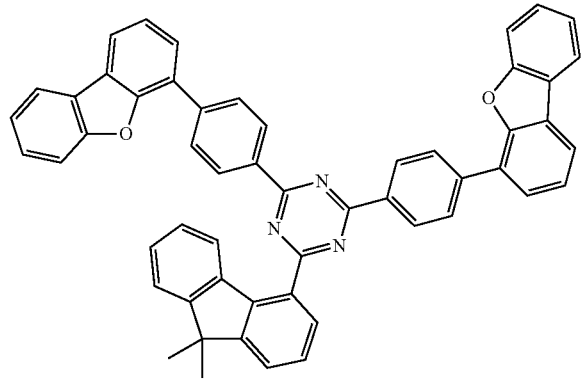
(80)
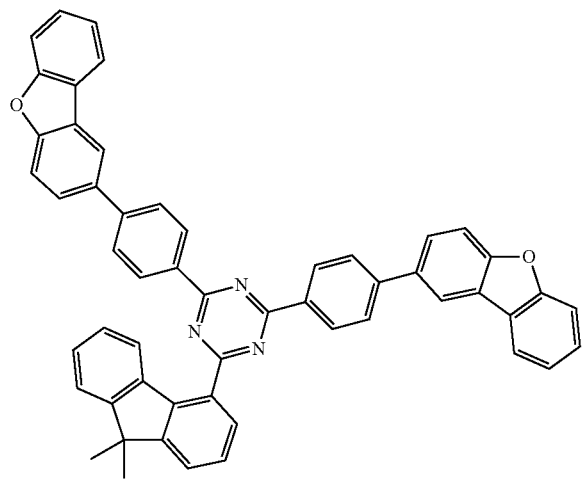
-continued
(81)
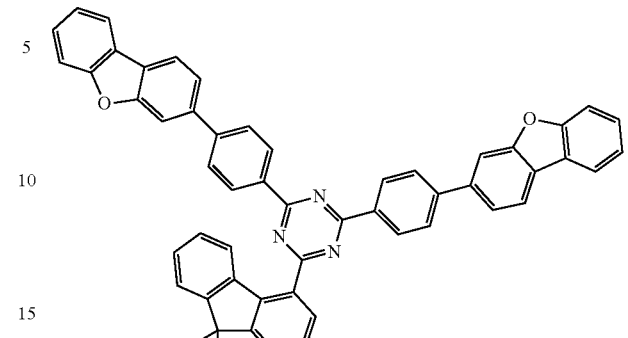
(82)
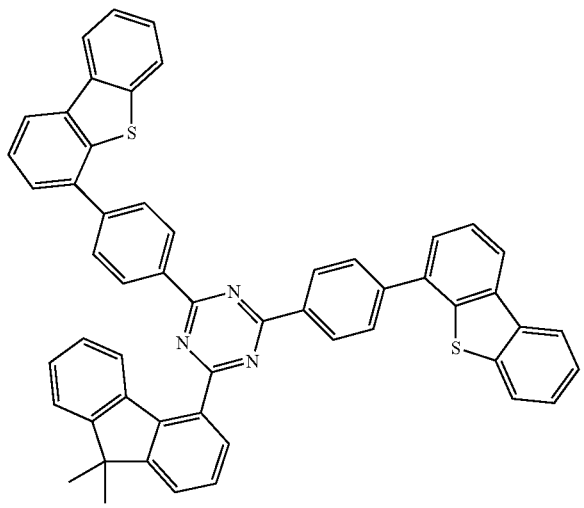
(83)
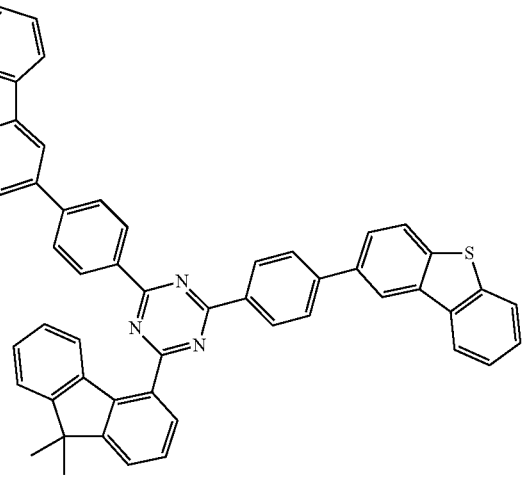

(84)
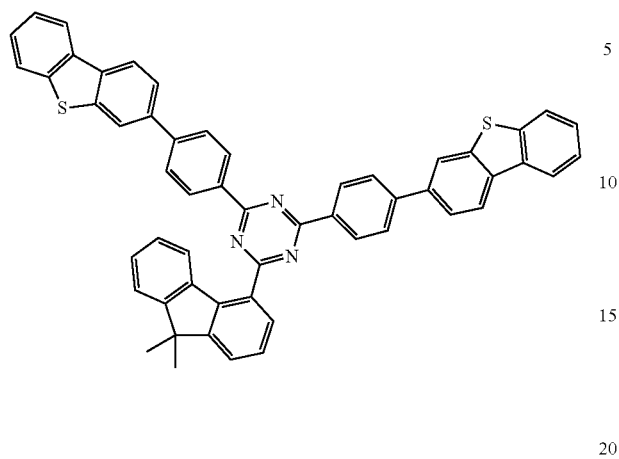
(85)
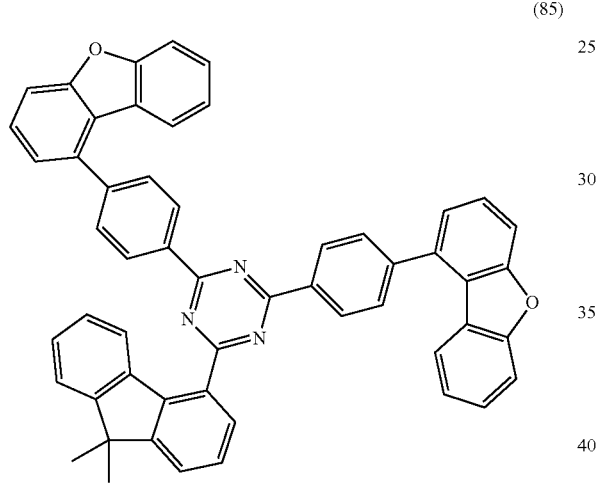
(86)
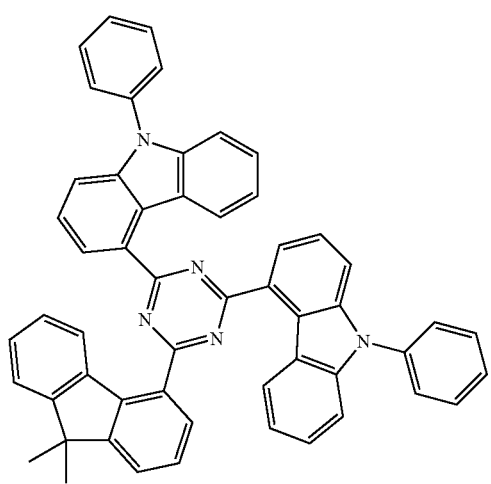
(87)
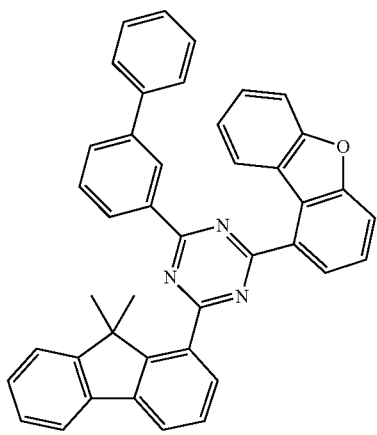
(88)
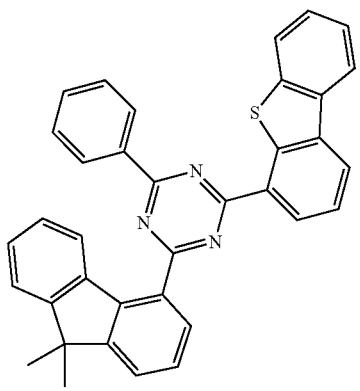
(89)
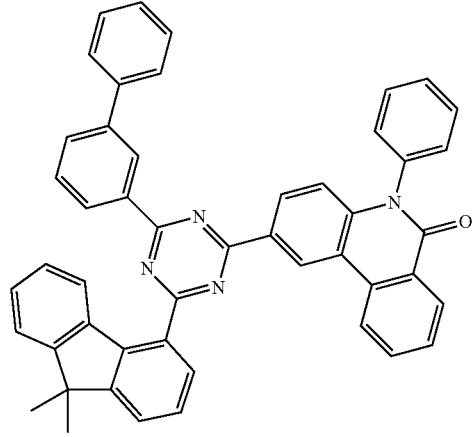

(90)
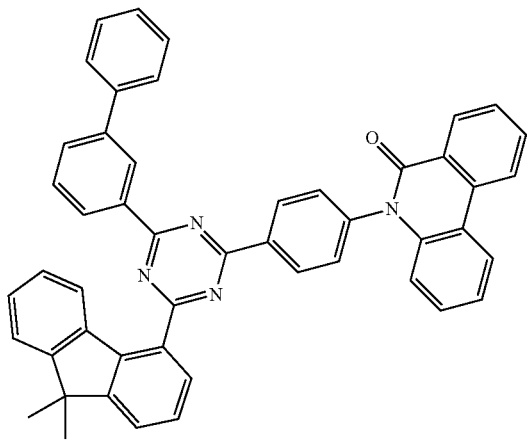
(91)
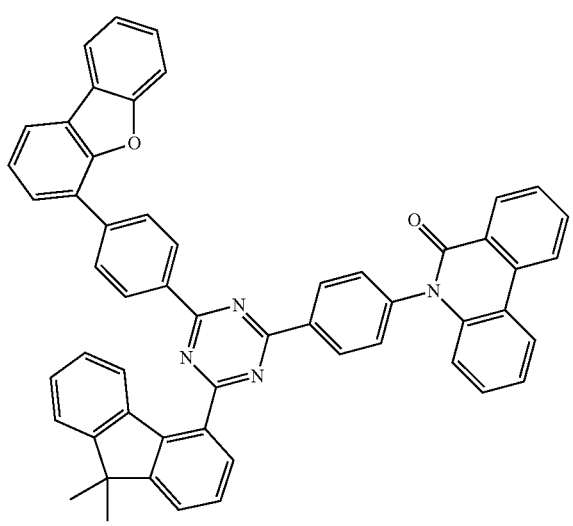
(92)
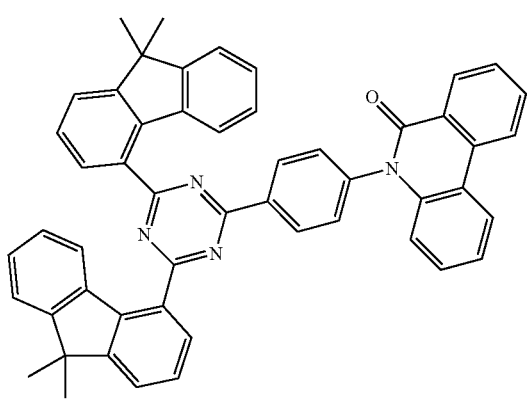
(93)
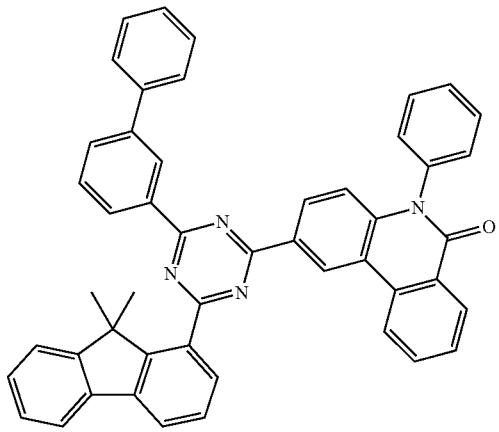
(94)
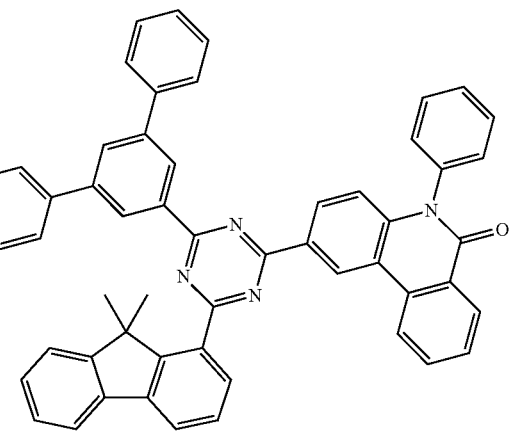
(95)
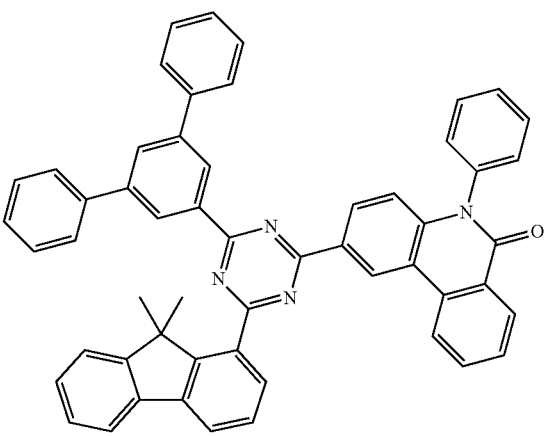

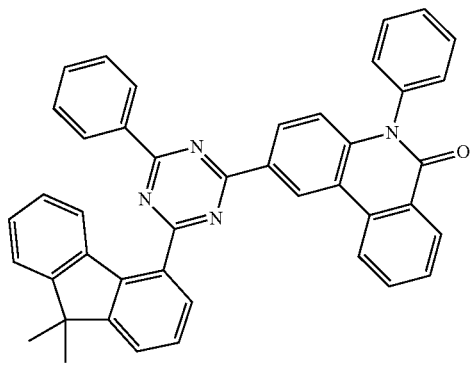
(96)
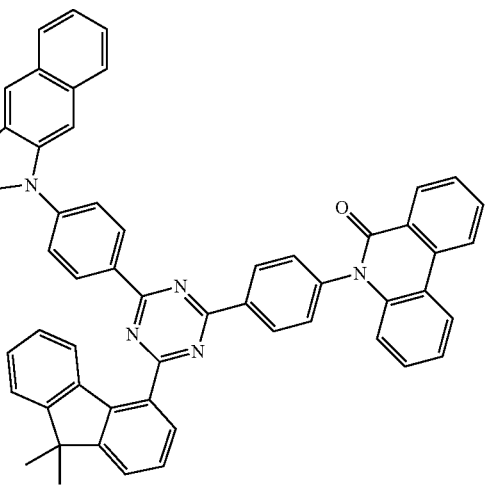
(99)
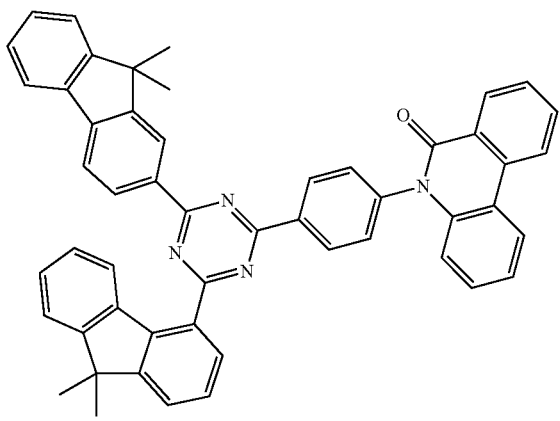
(97)
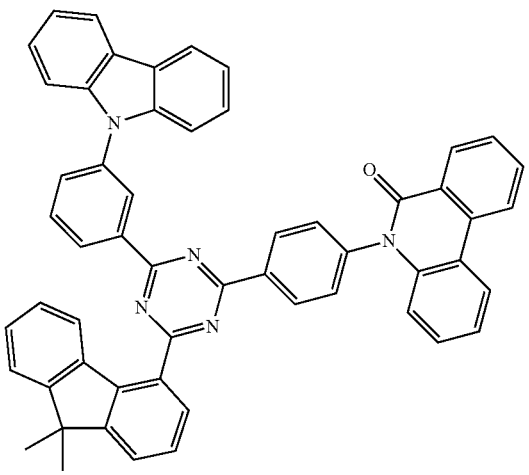
(100)
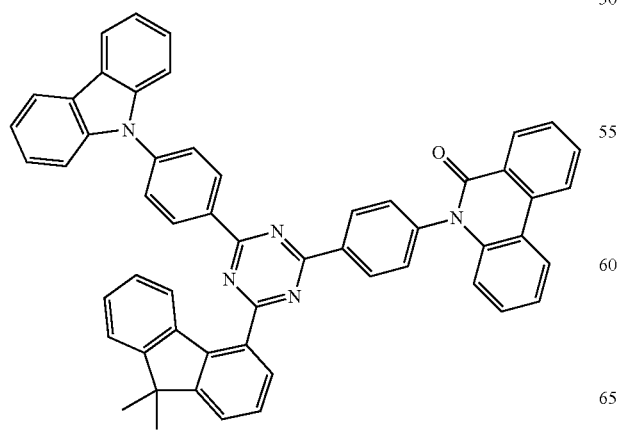
(98)
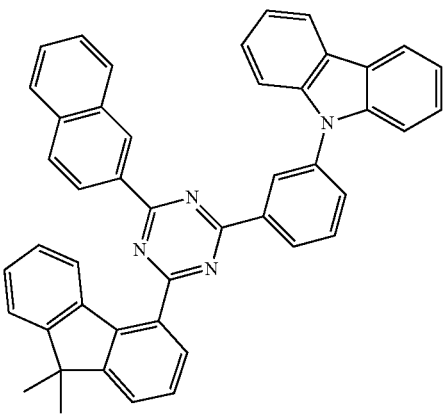
(101)

(102)
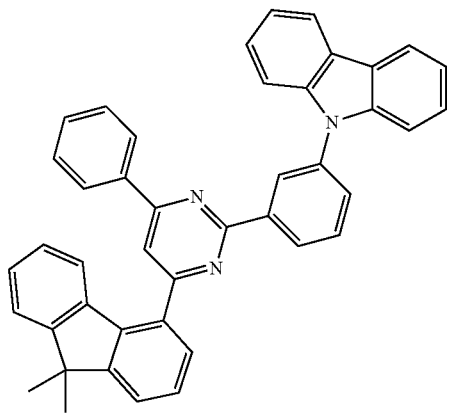
(103)
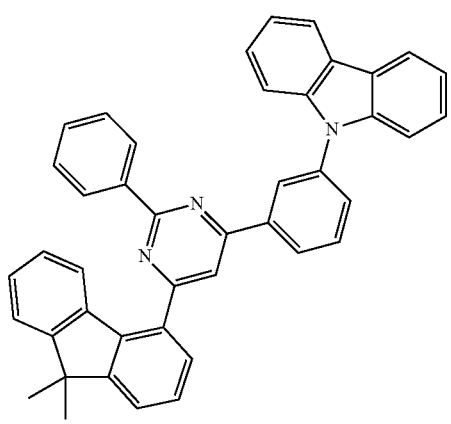
(104)
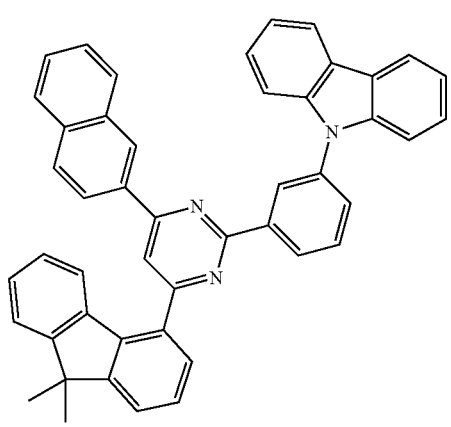
(105)
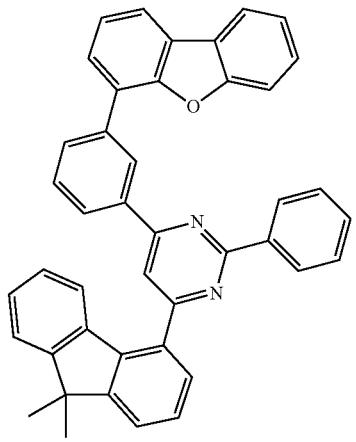
(106)
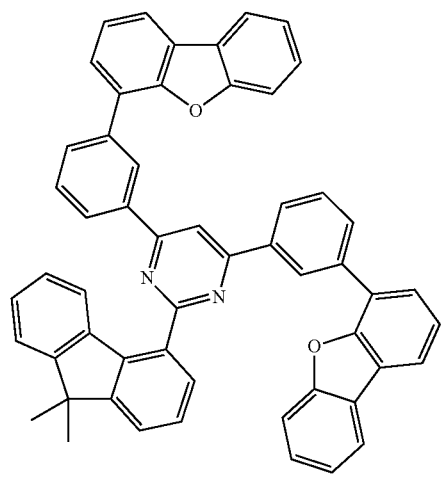
(107)
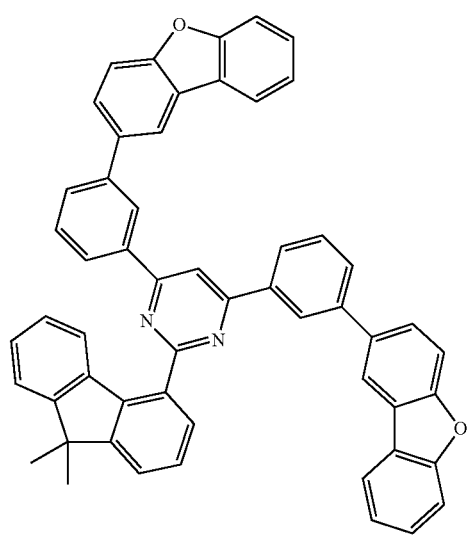

(108)
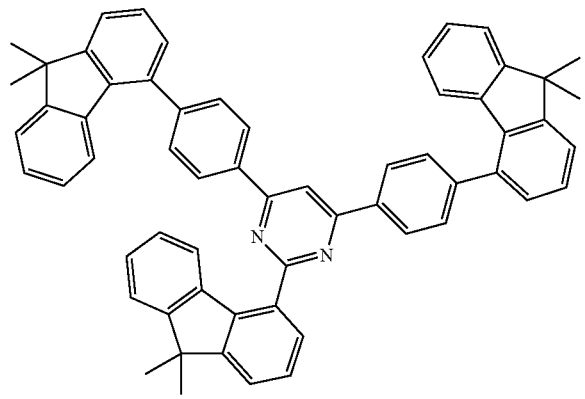
(109)
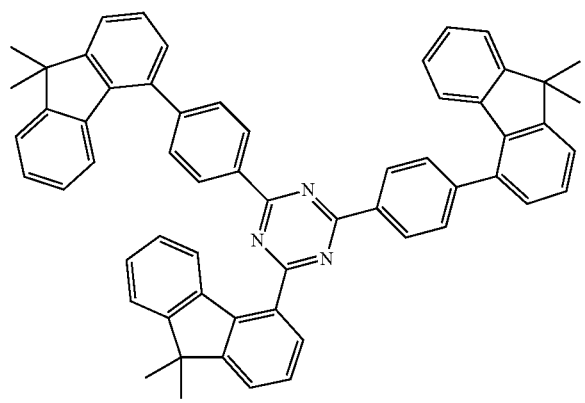
(110)
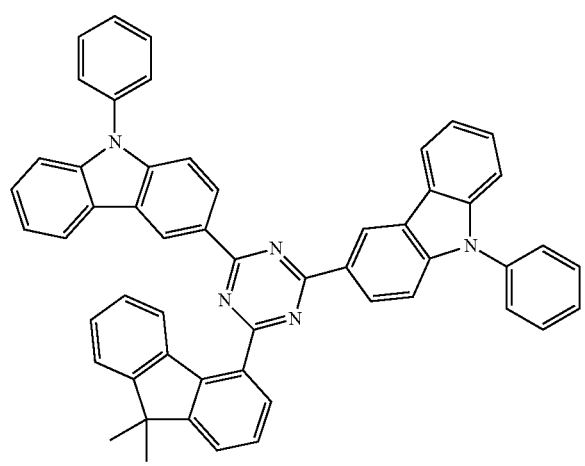
(111)
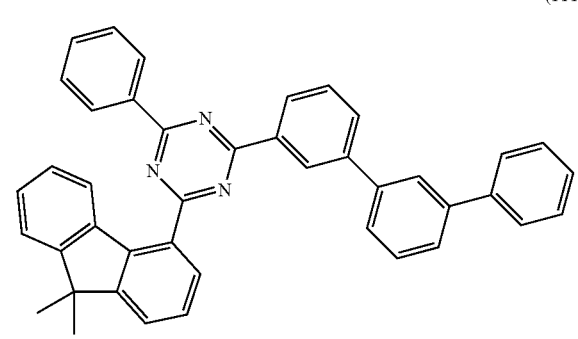
(112)
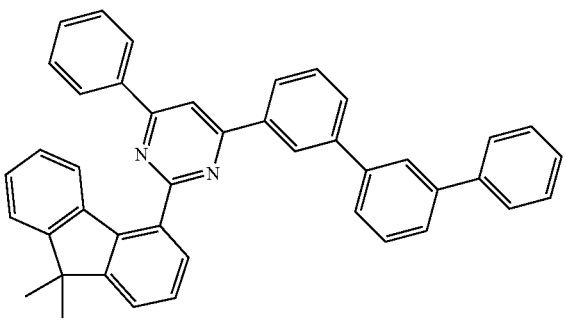
(113)
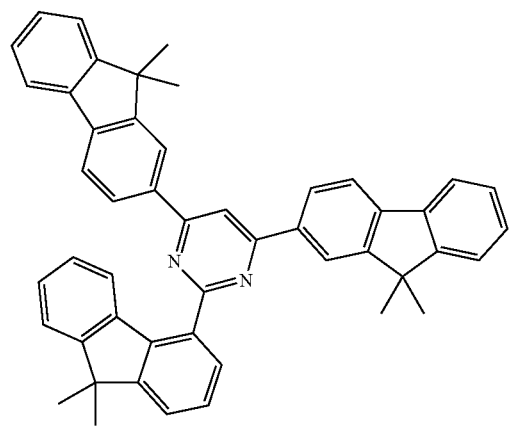
(114)
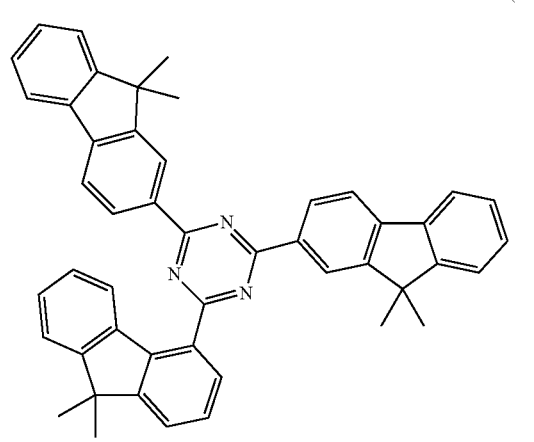

(115)
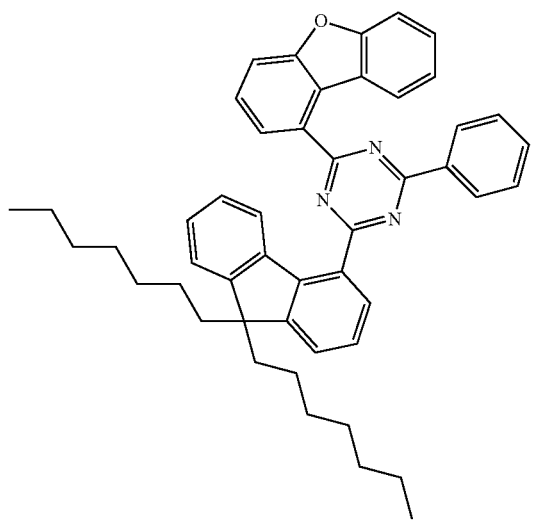
(116)
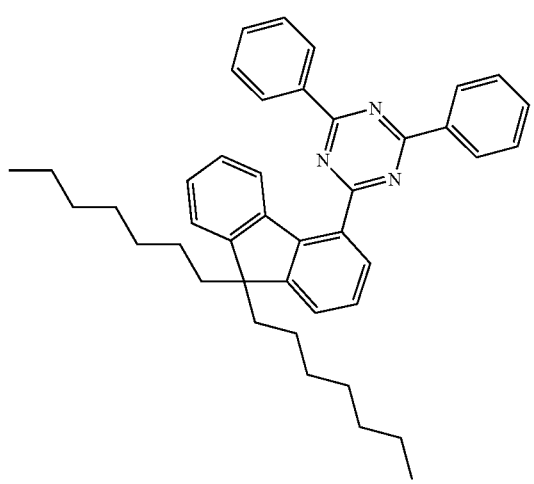
(117)
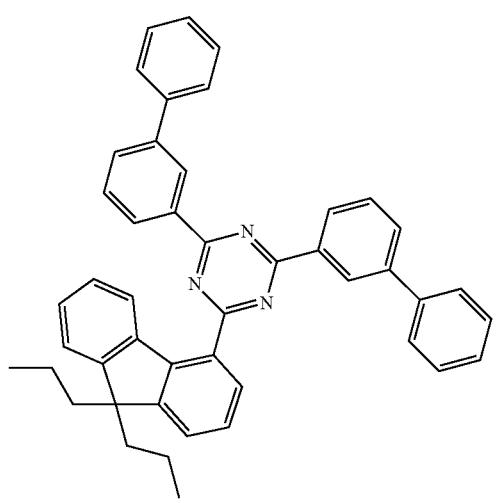
(118)
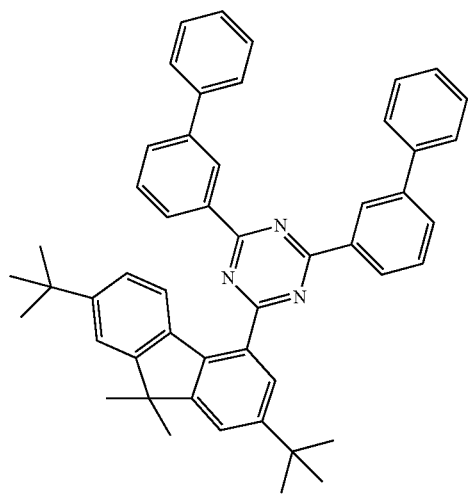
(119)
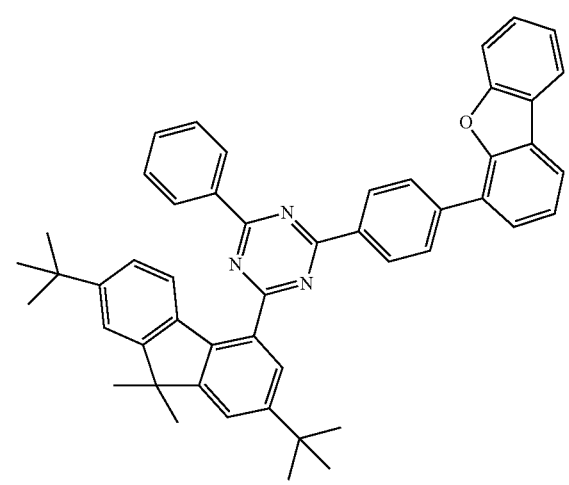
(120)
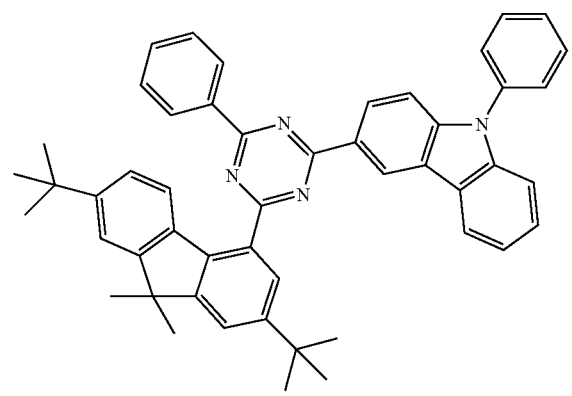

(121)
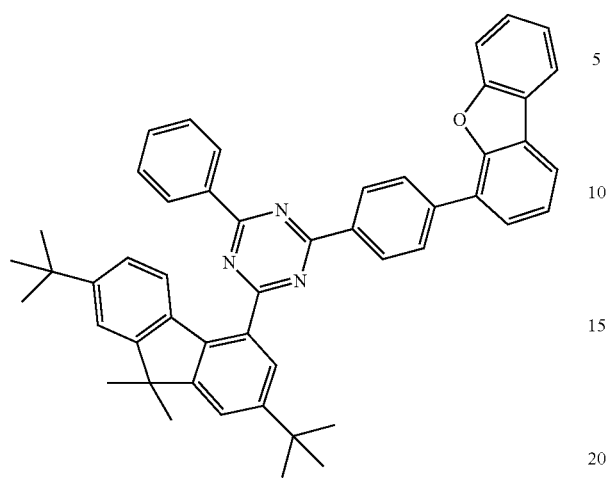
(124)
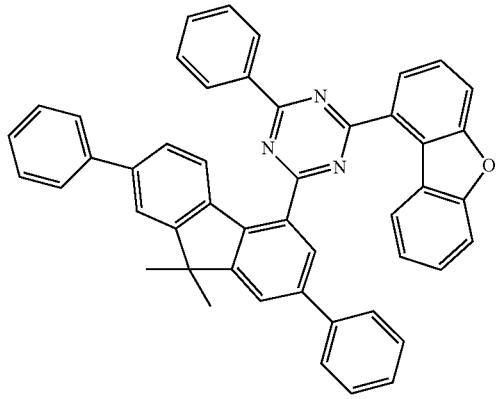
(122)
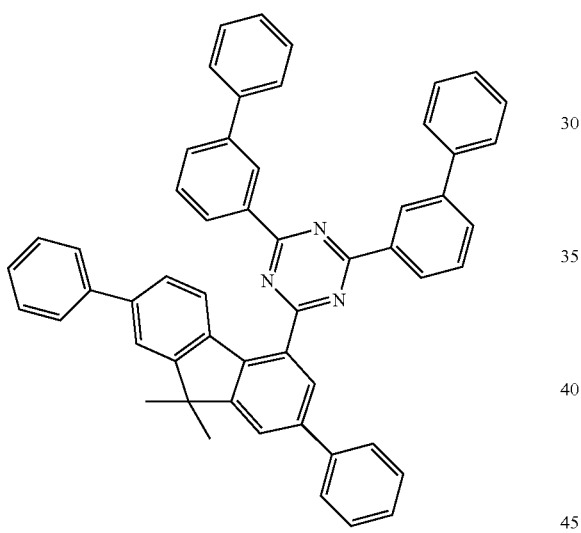
(125)
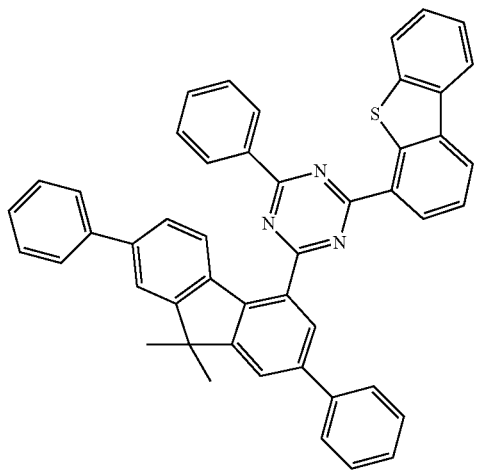
(123)
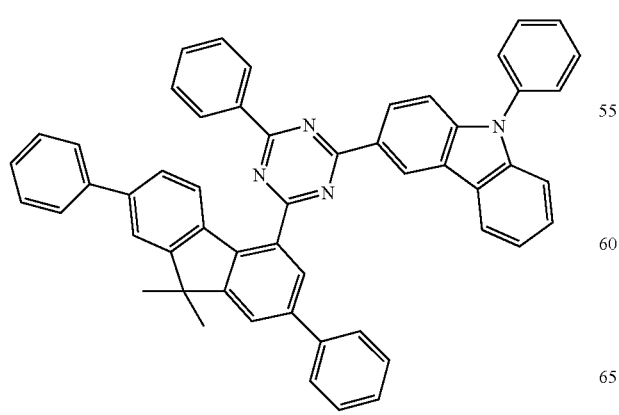
(126)
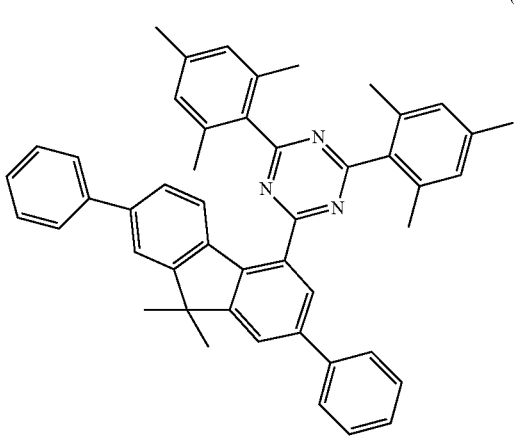

-continued
(127)
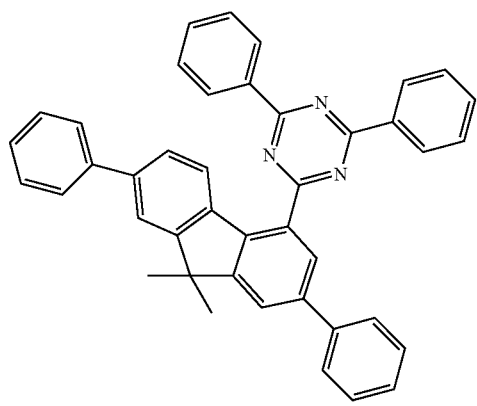
(128)
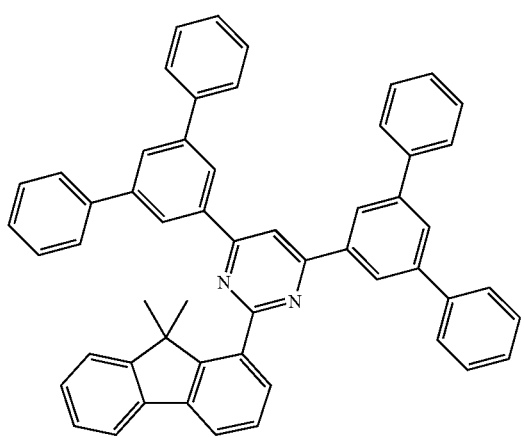
(129)
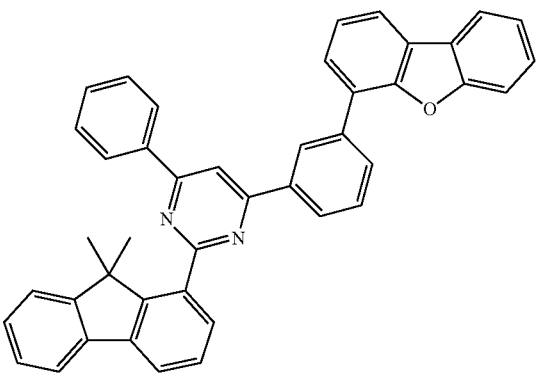
(130)
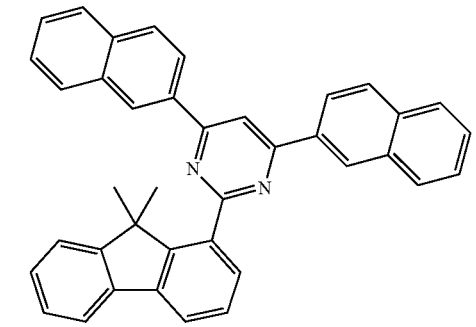
-continued
(131)
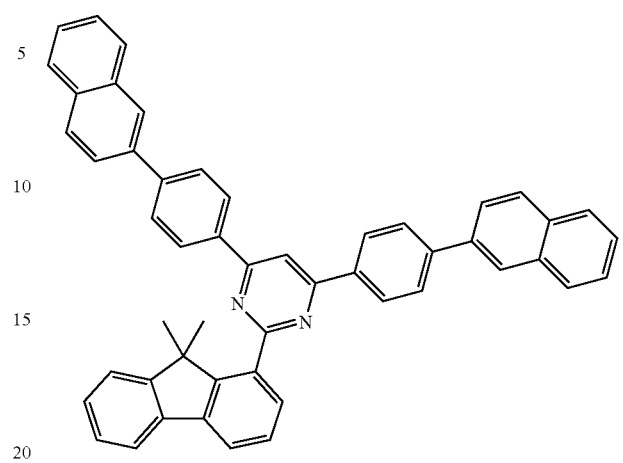
(132)
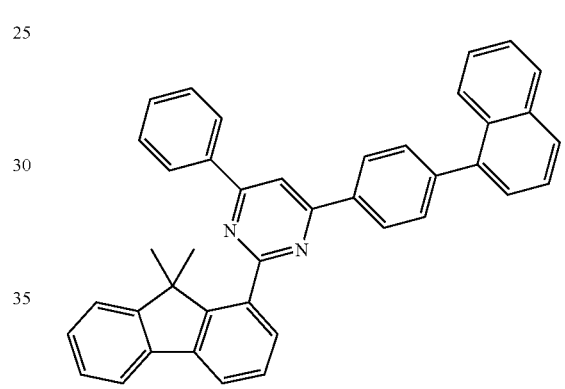
(133)
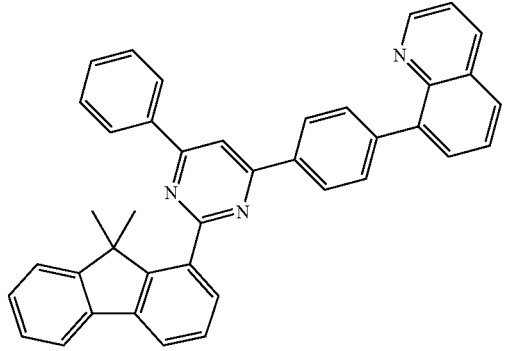
(134)
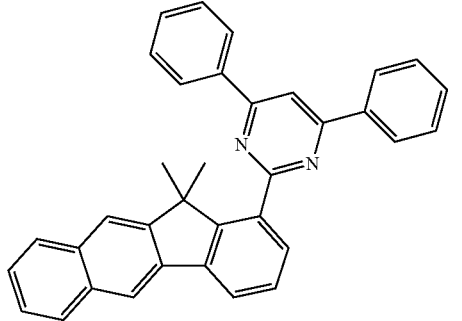

(135)
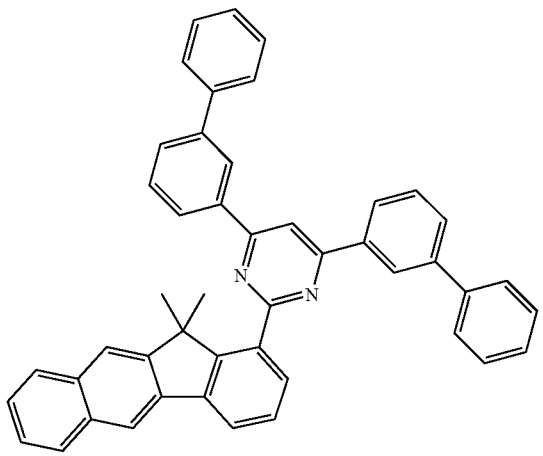
(136)
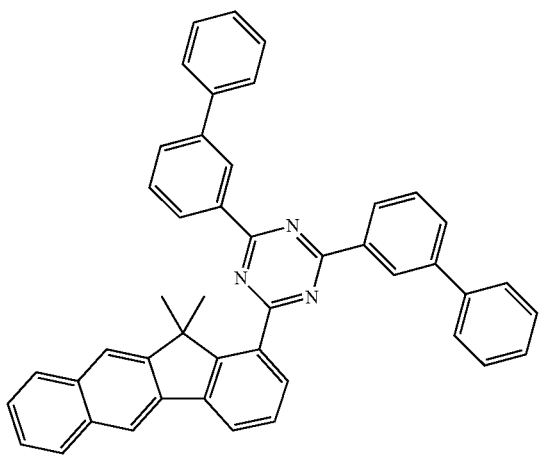
(137)
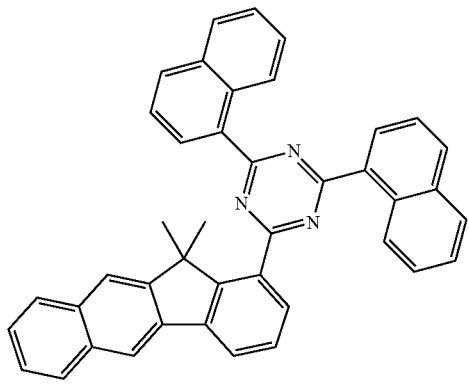
(138)
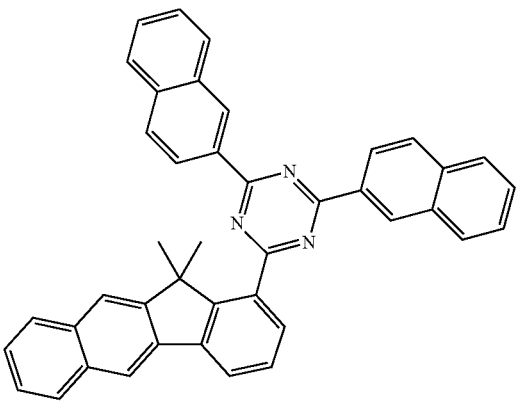
(139)
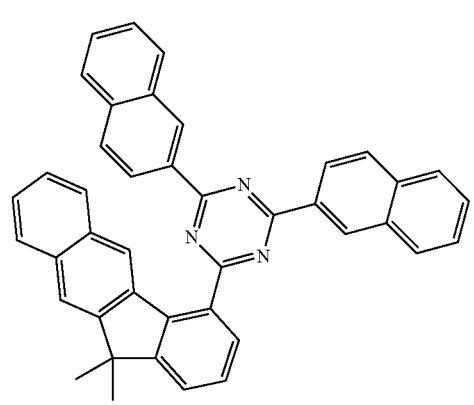
(140)
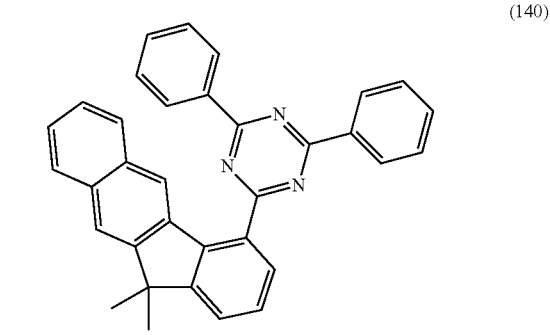
(141)
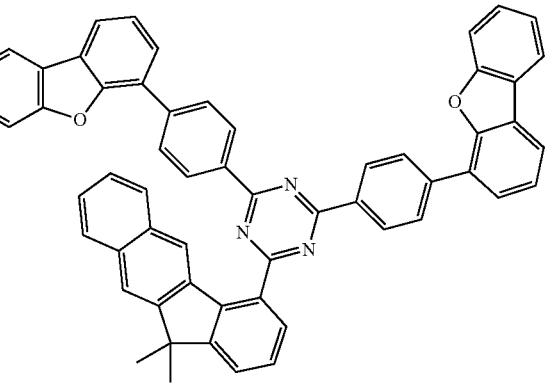

(142)
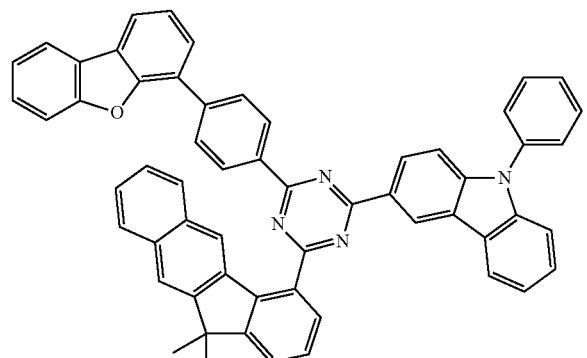
(143)
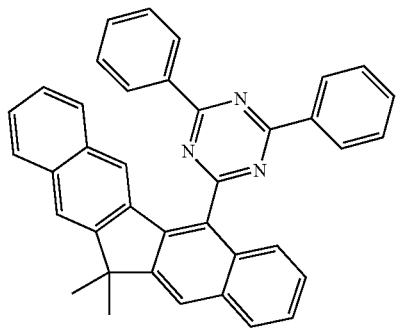
(144)
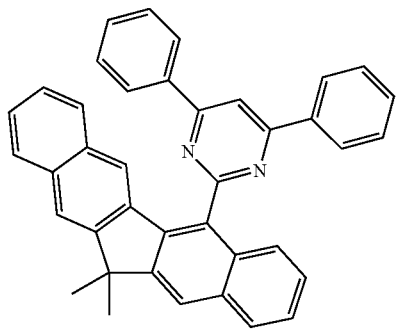
(145)
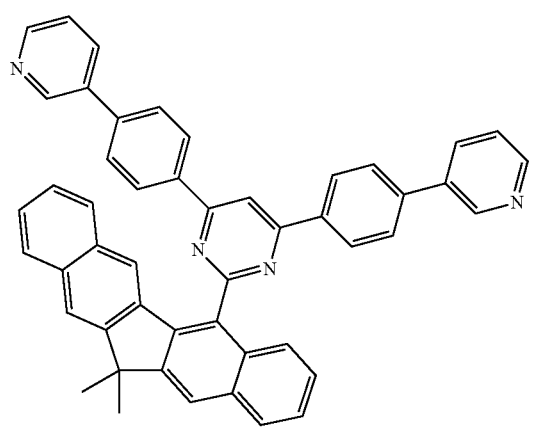
(147)
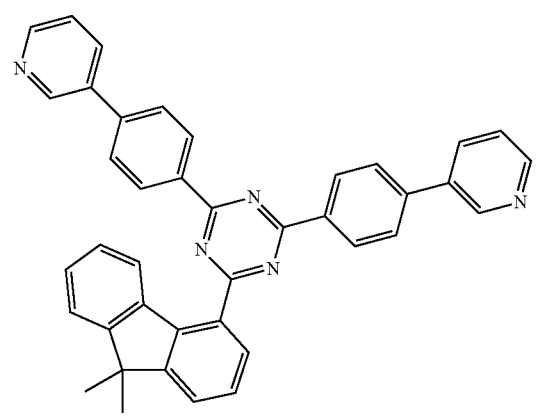
(148)
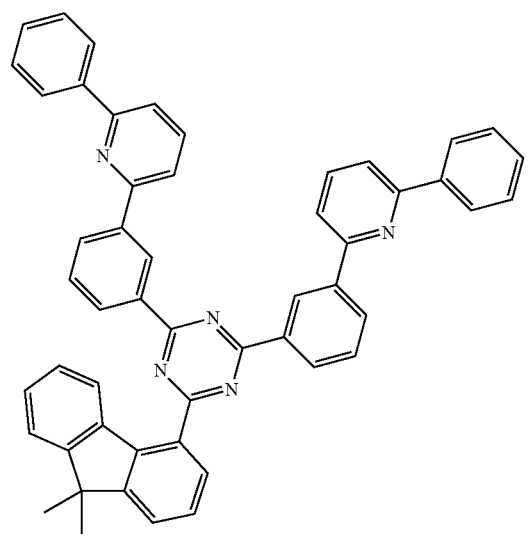
(149)
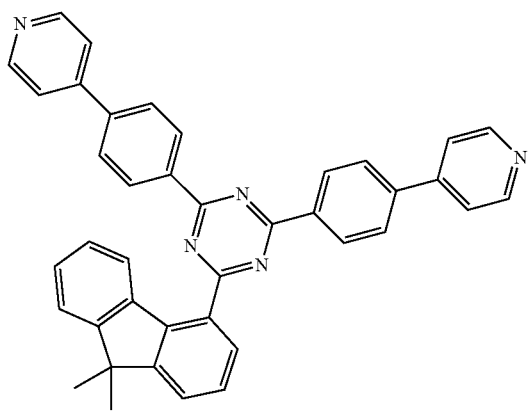

(150)
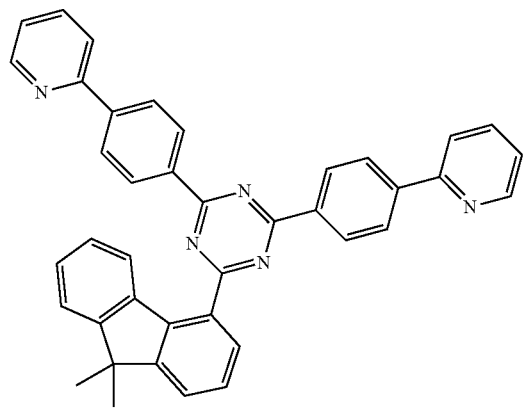
(151)
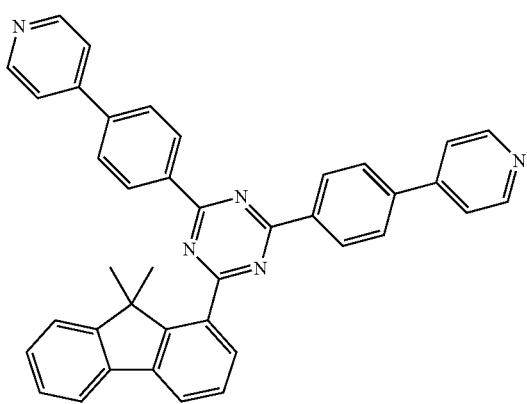
(152)
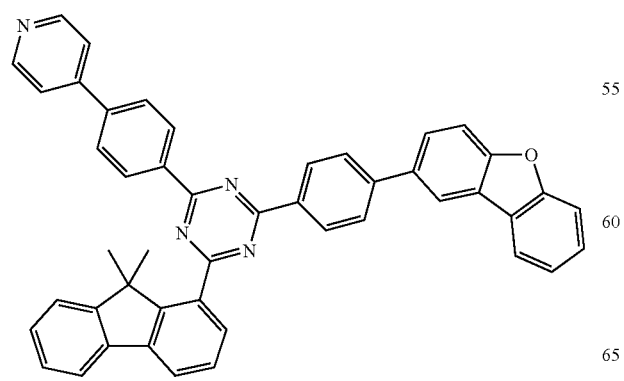
(153)
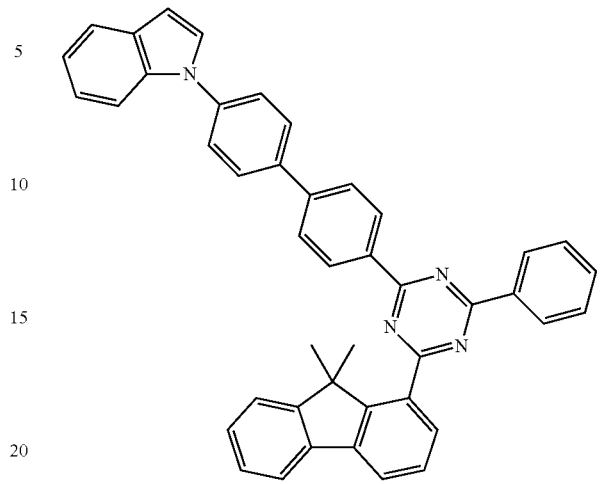
(154)
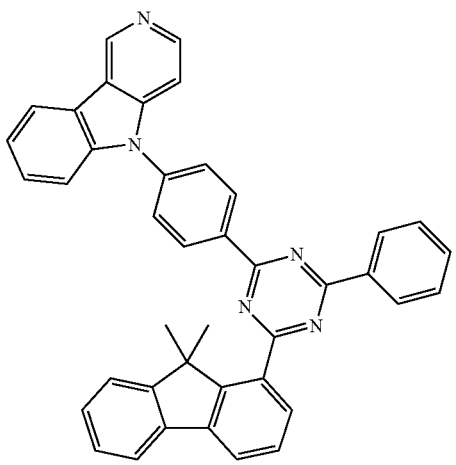
(155)
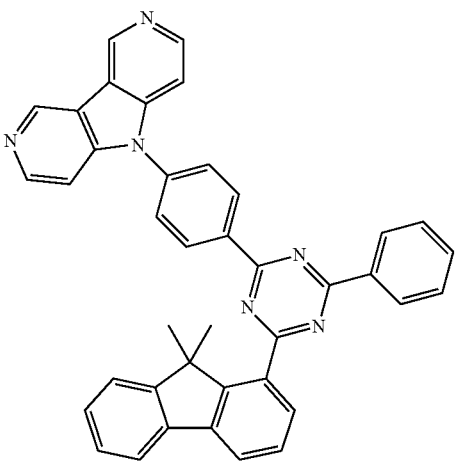

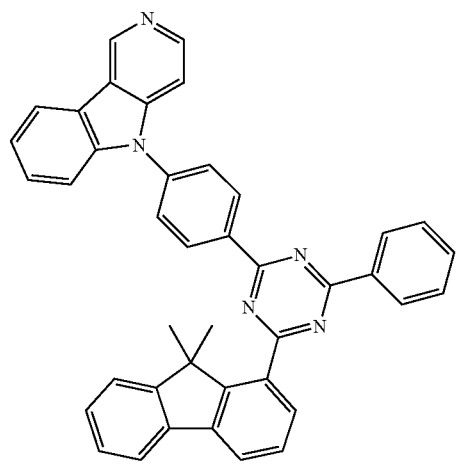
(156)
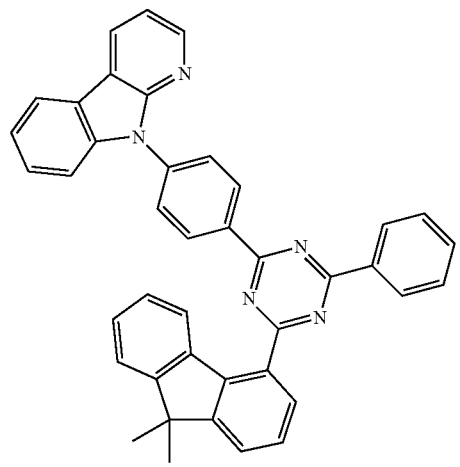
(159)
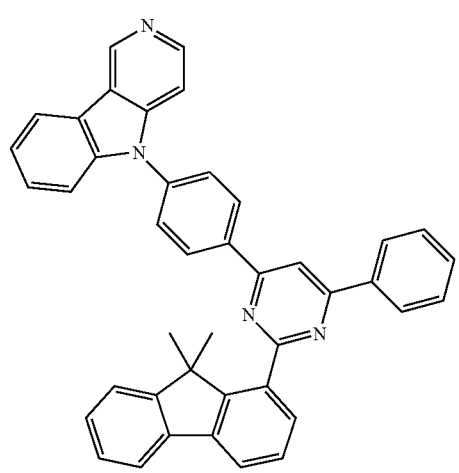
(157)
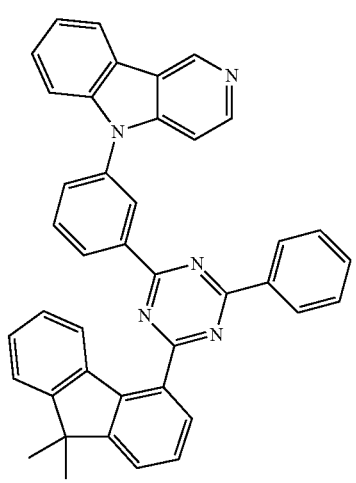
(160)
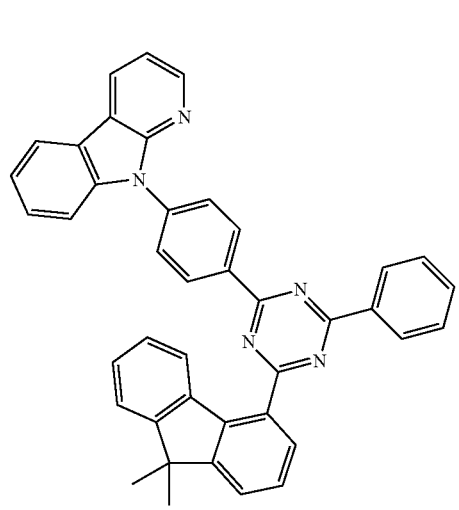
(158)
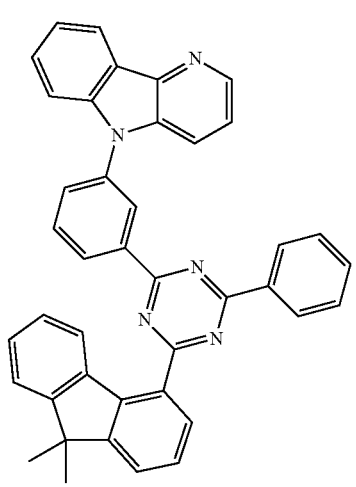
(161)

(162)
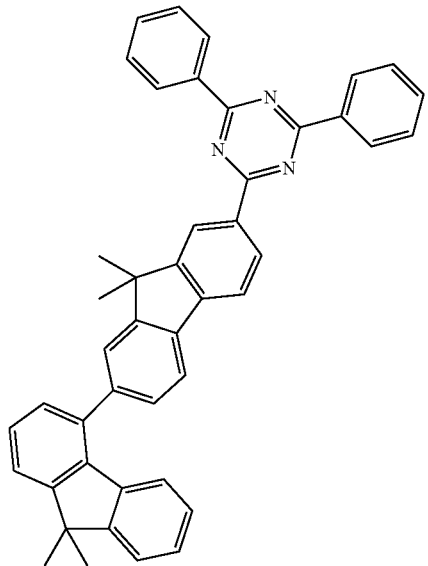
(163)
(164)
(165)
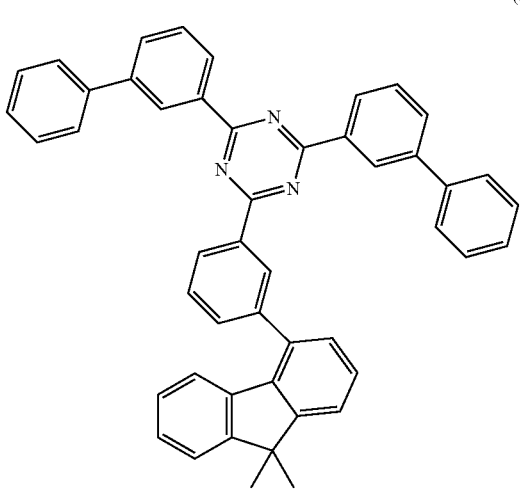
(166)
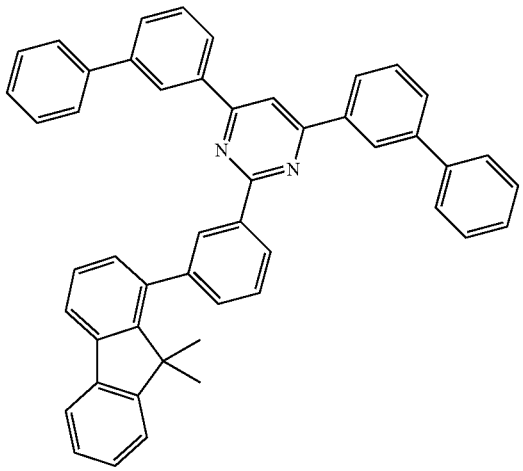
(167)
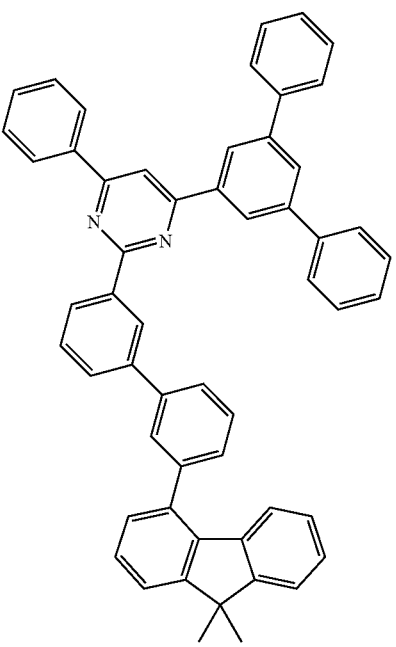

(168)
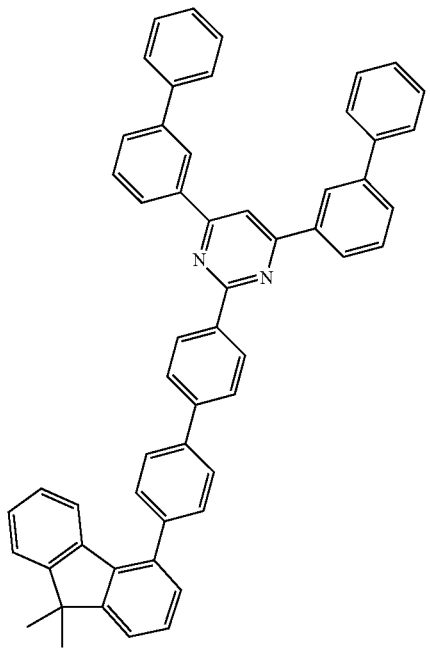
(169)
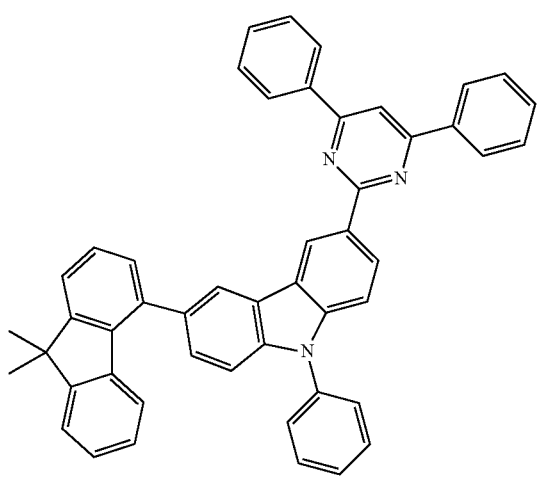
(170)
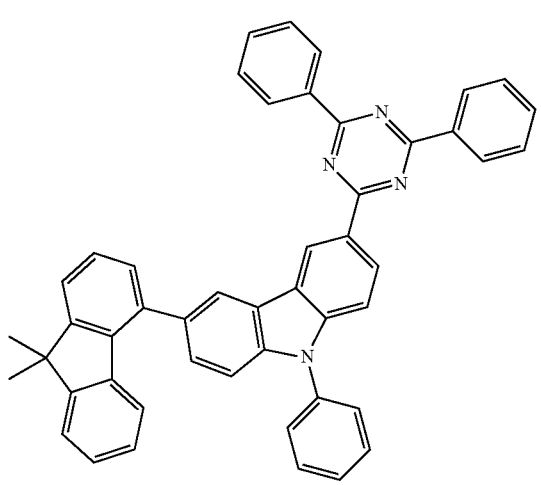
(171)
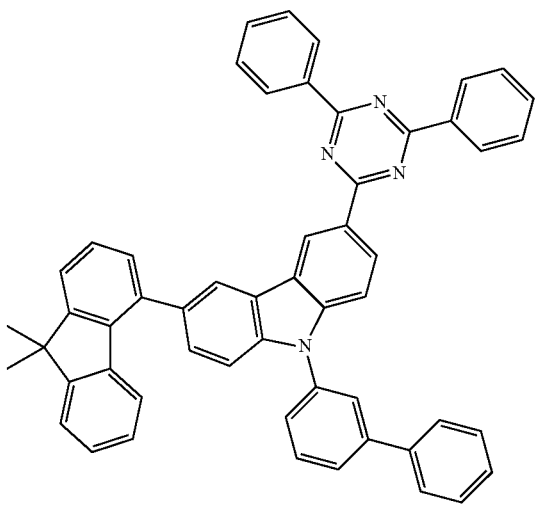
(172)
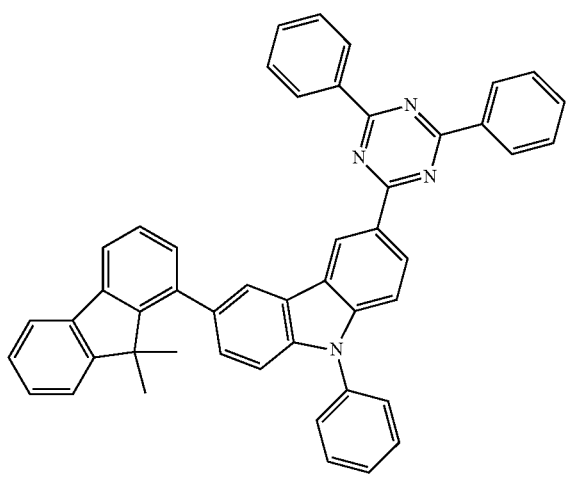
(173)
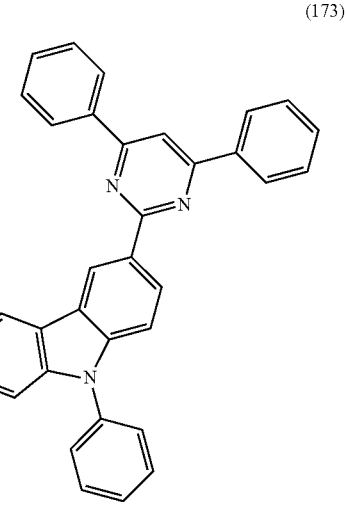

(174)
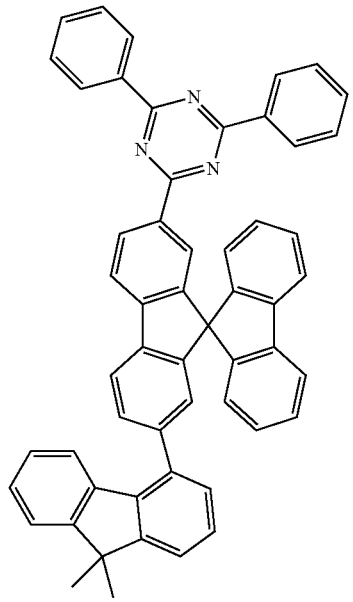
(177)
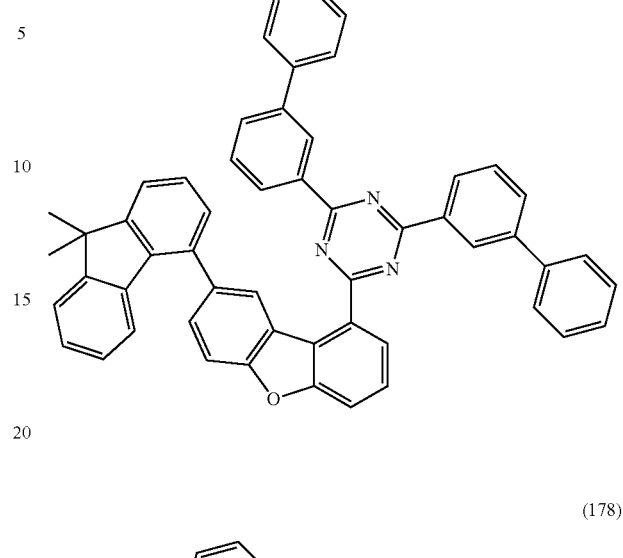
(175)
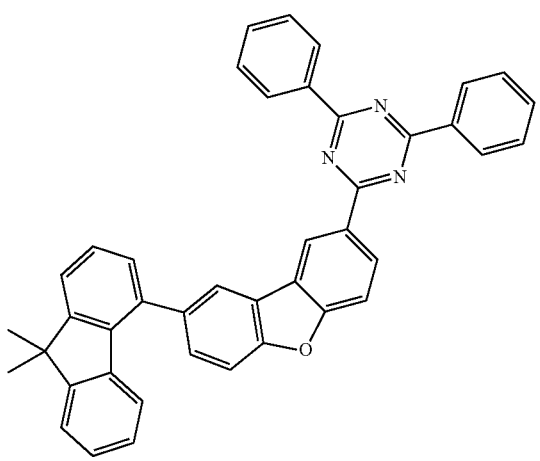
(178)
(176)
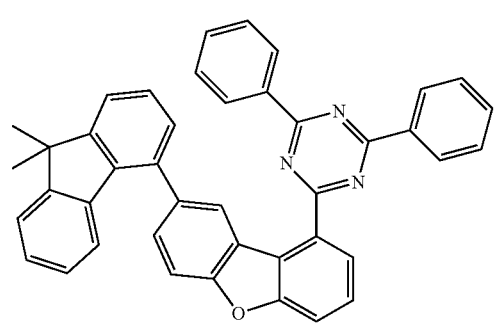
(179)
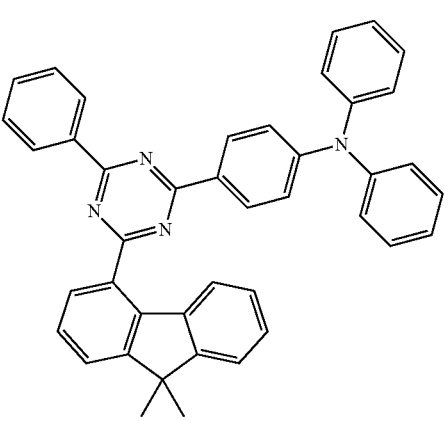

-continued
(180)
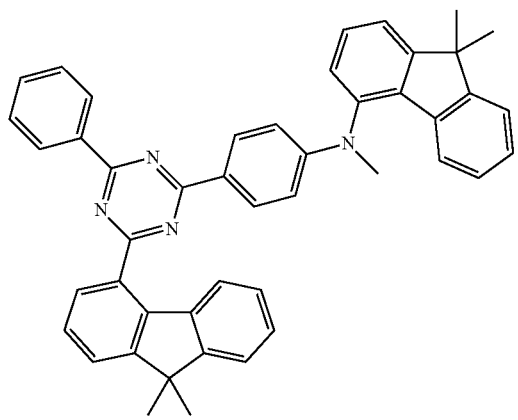
(181)
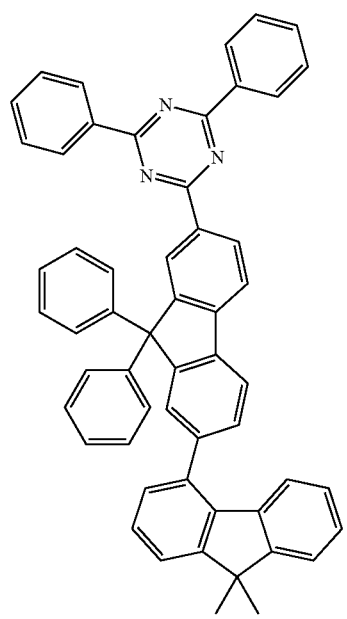
(182)
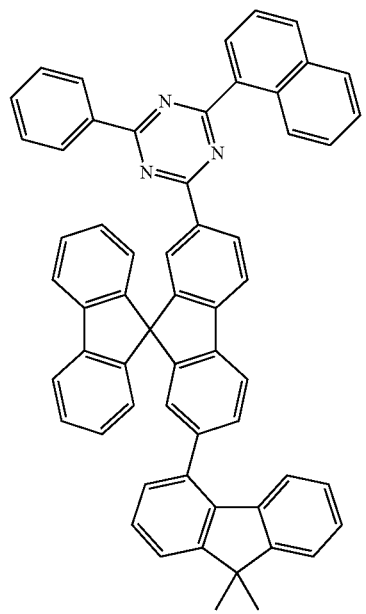
-continued
(183)
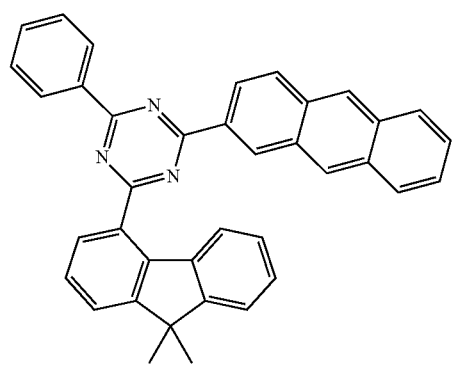
(184)
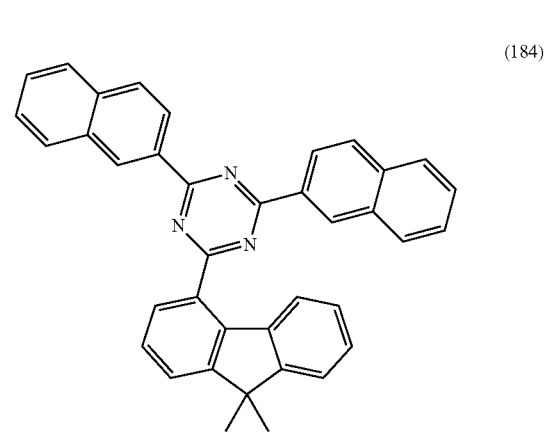
(185)
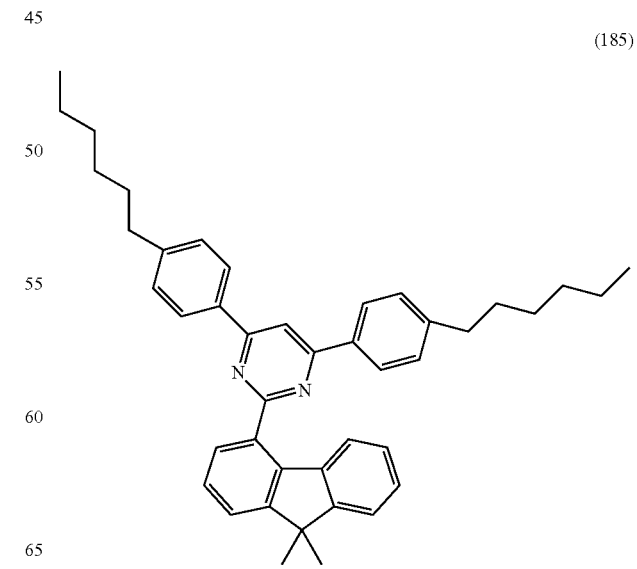

(186)
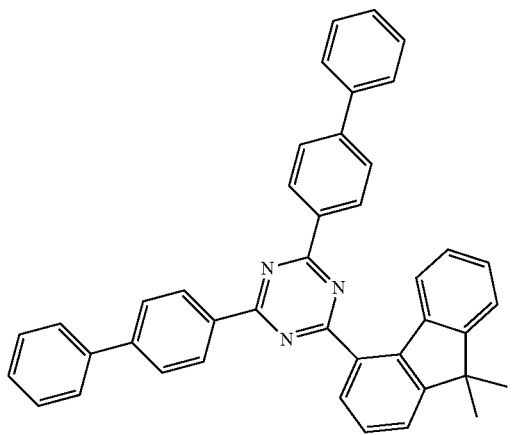
(187)
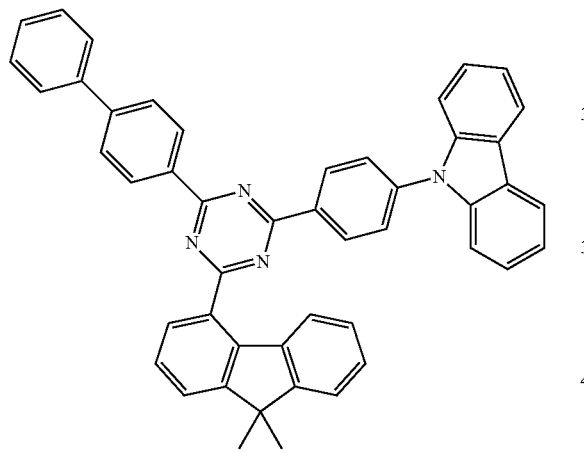
(188)
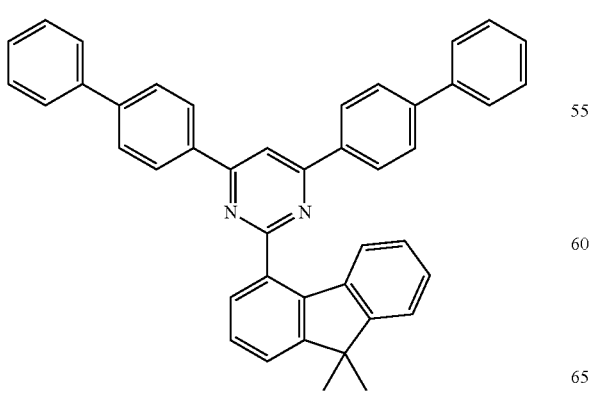
(189)
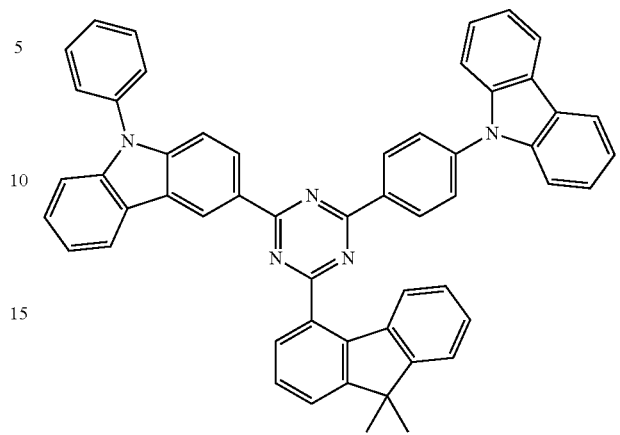
(190)
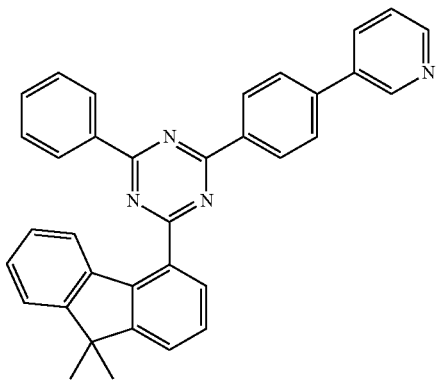
(191)
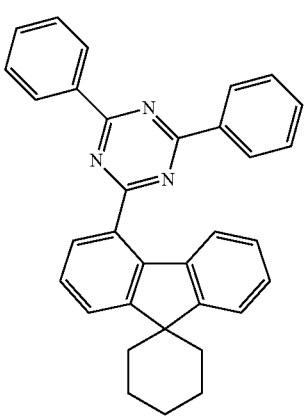

(192)
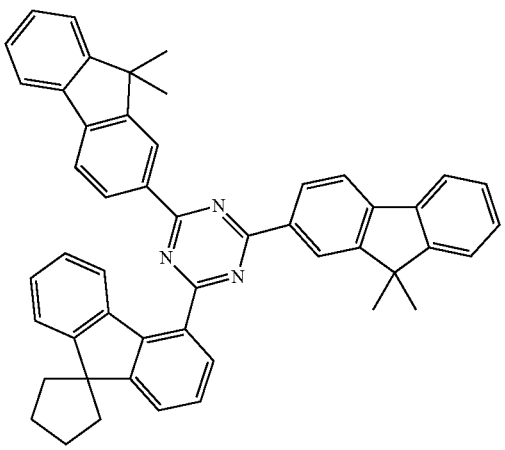
(193)
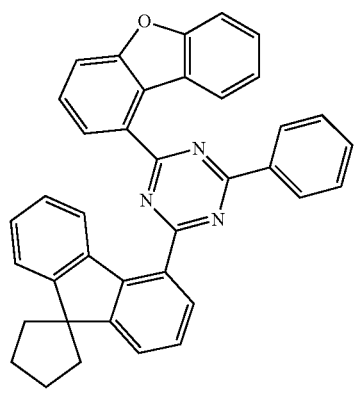
(194)
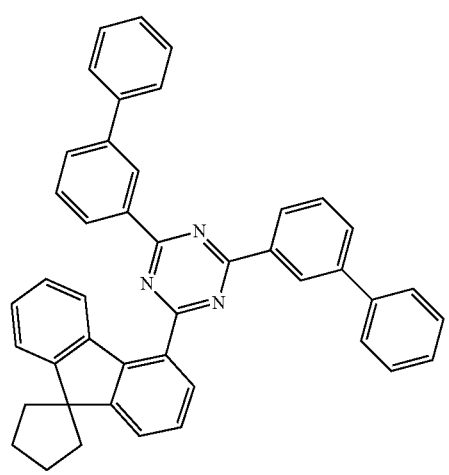
(195)
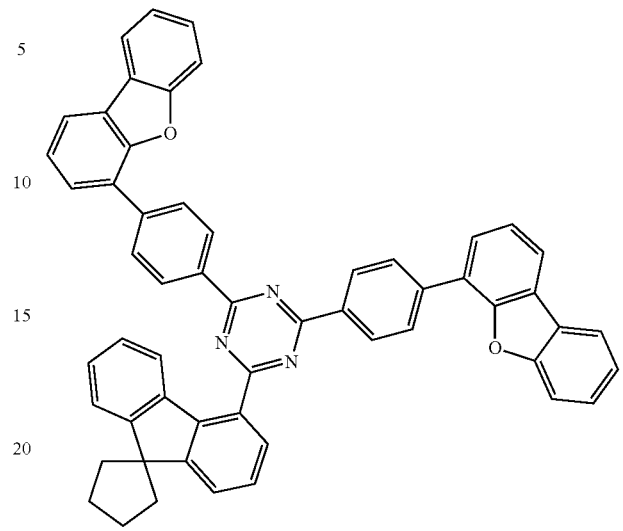
(196)
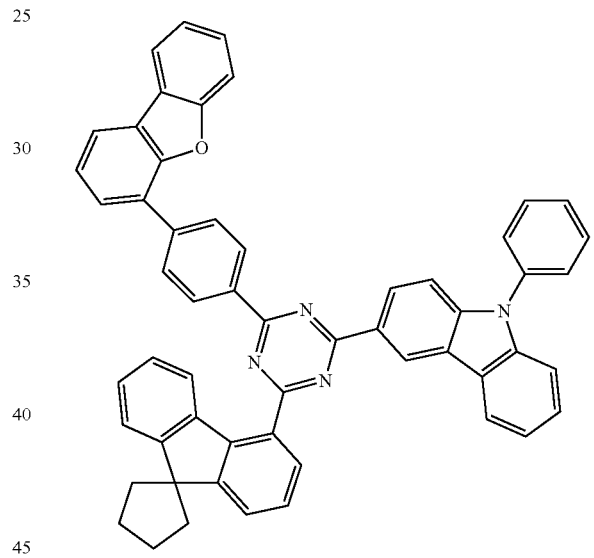
(197)
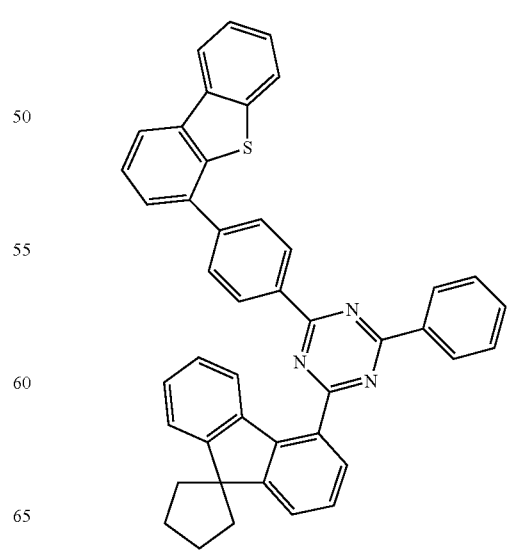

(198)
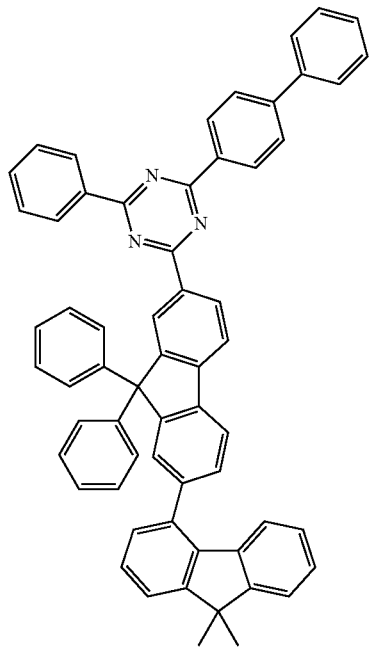
(200)
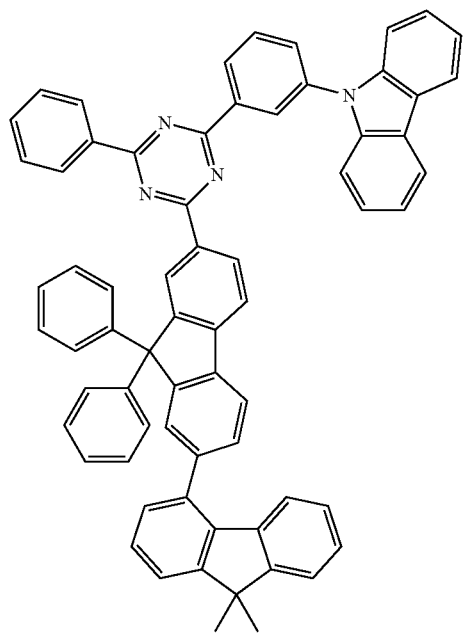
(199)
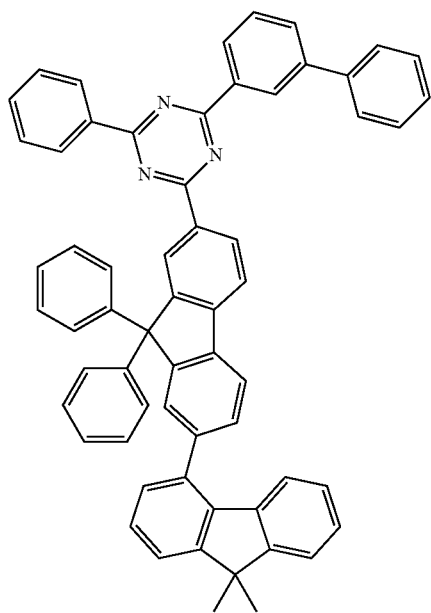
(201)
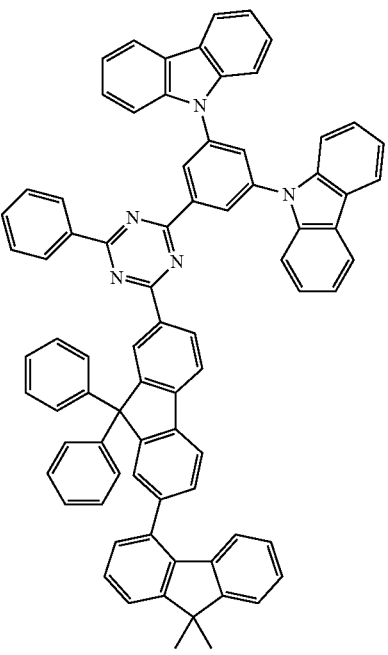

(202)
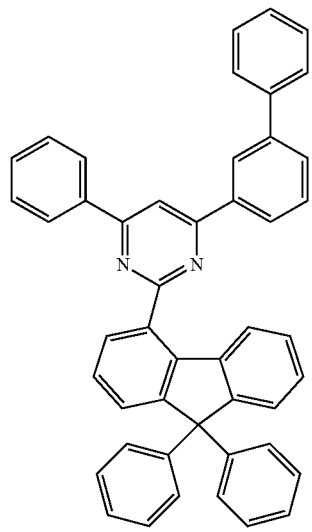
(203)
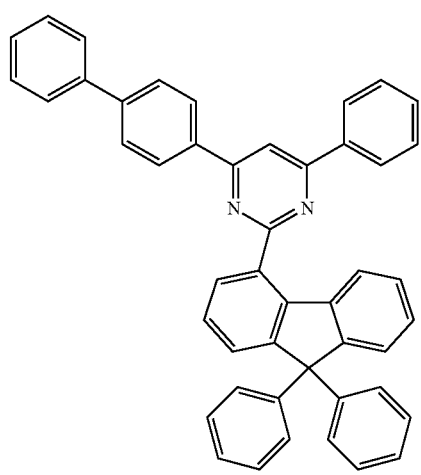
(204)
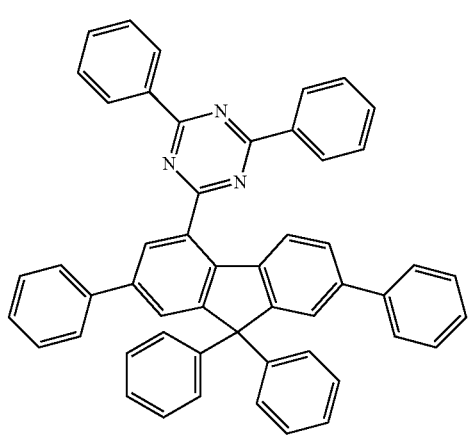
(205)
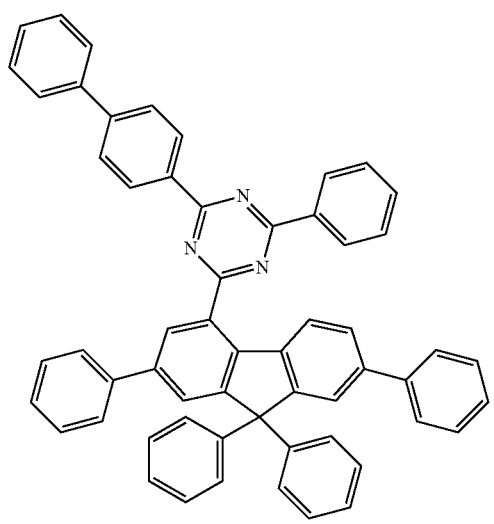
(206)
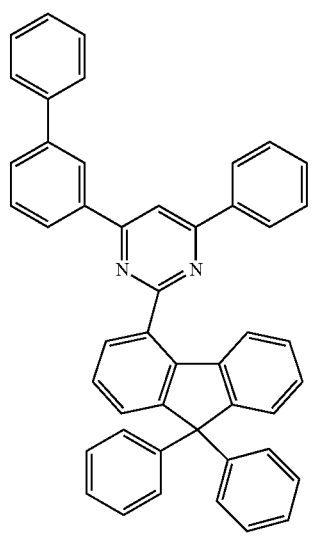
(207)
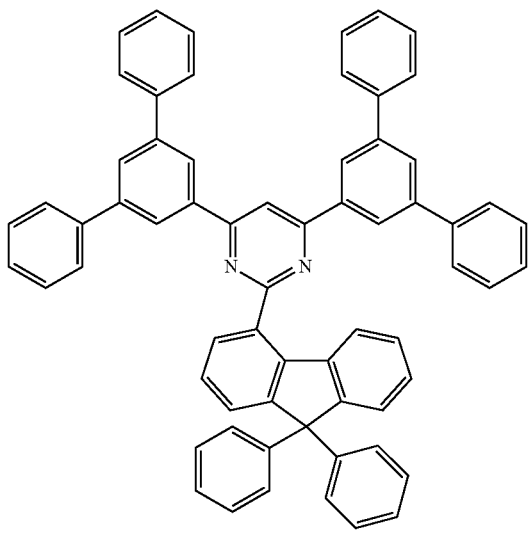

(208)
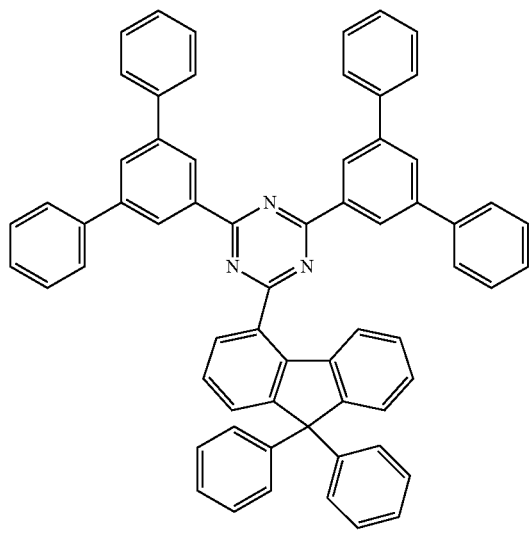
(209)
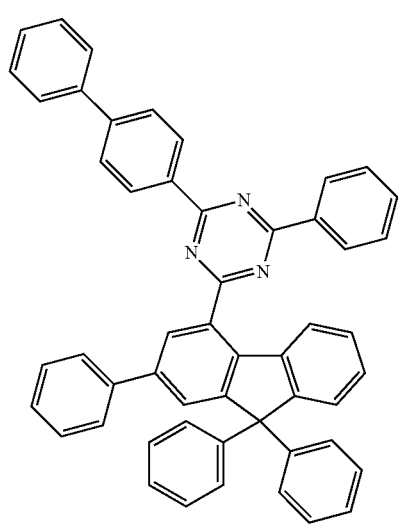
(210)
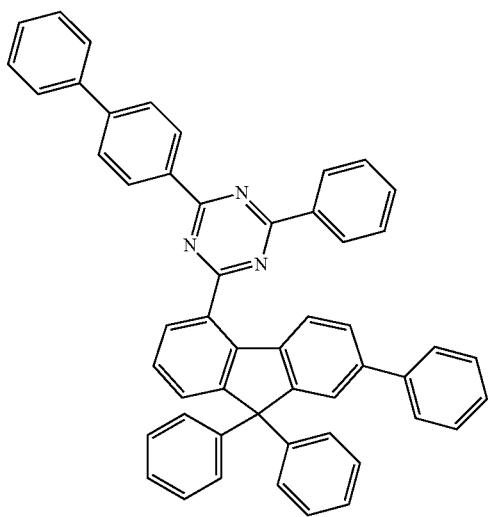
(211)
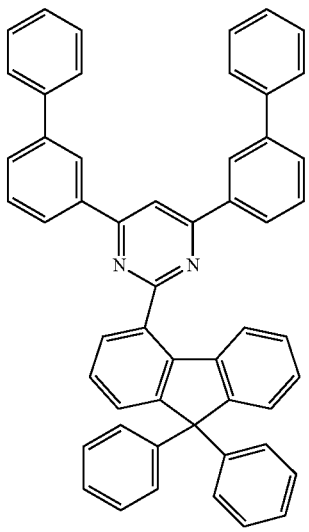
(212)
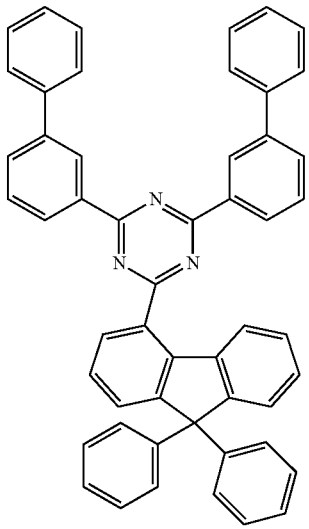
(213)
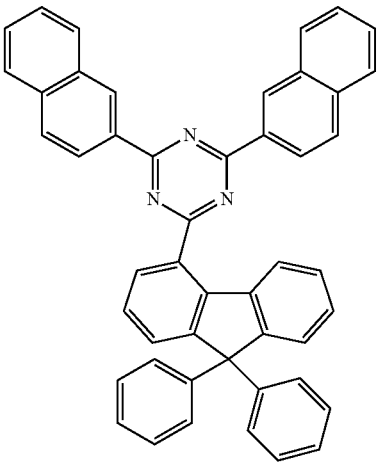

(214)
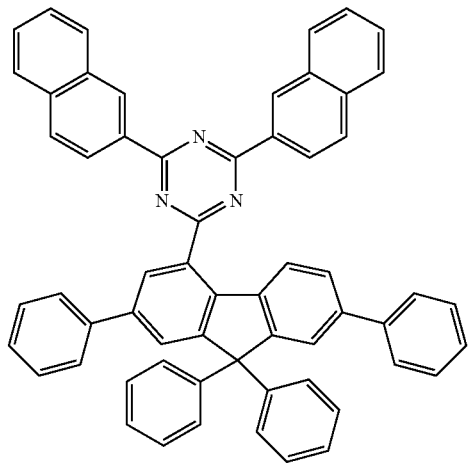
(215)
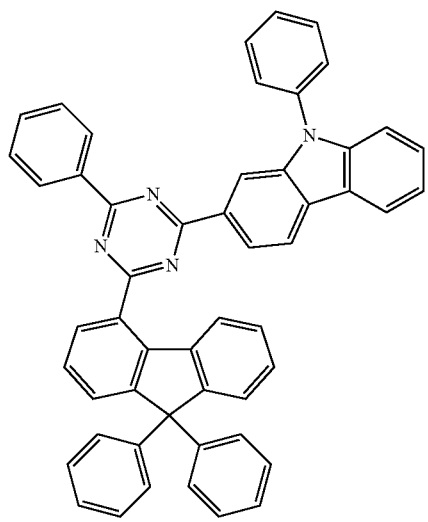
(216)
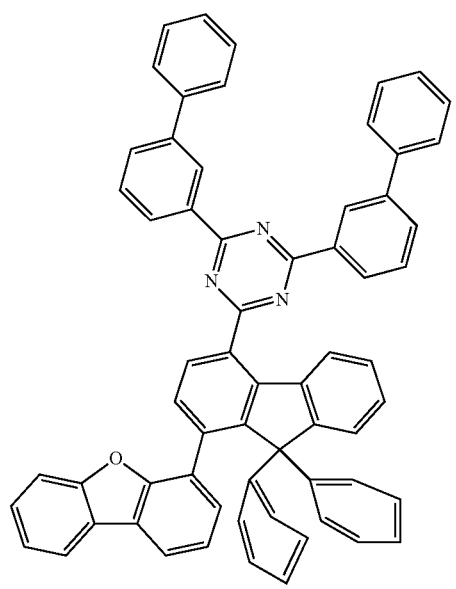
(217)
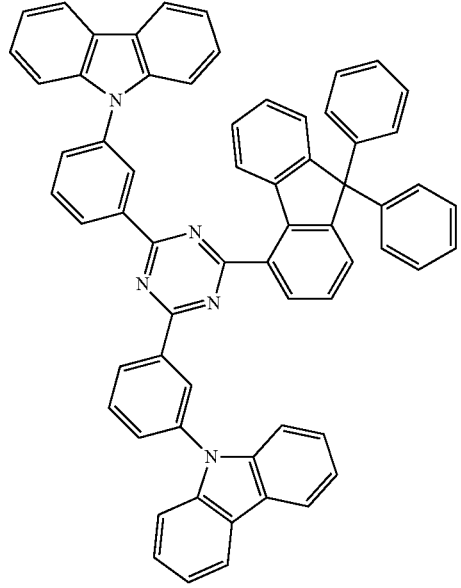
(218)
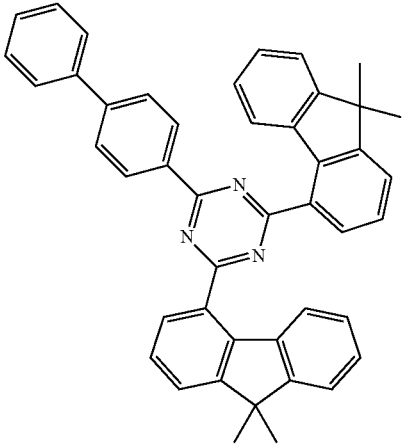
(219)
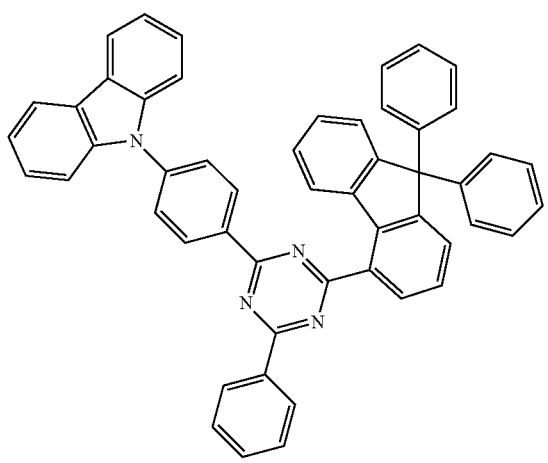

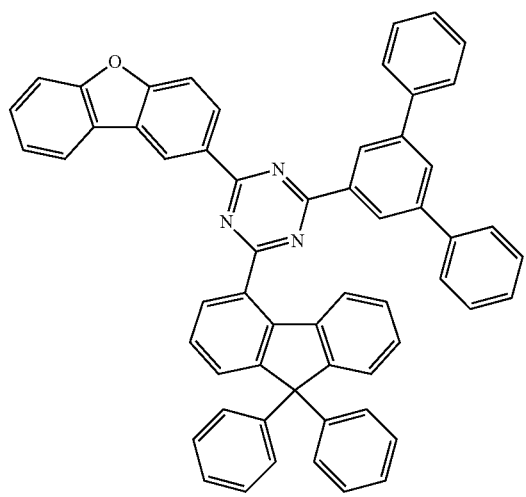
(219)
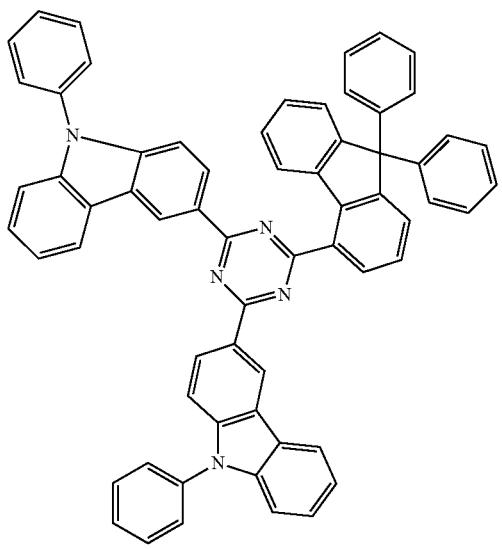
(220)
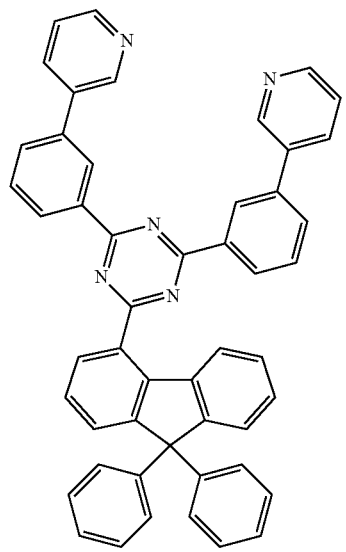
(221)
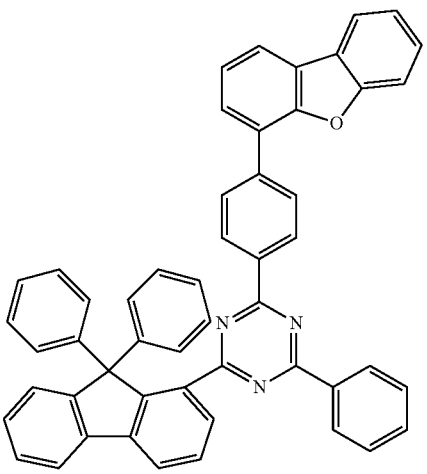
(222)
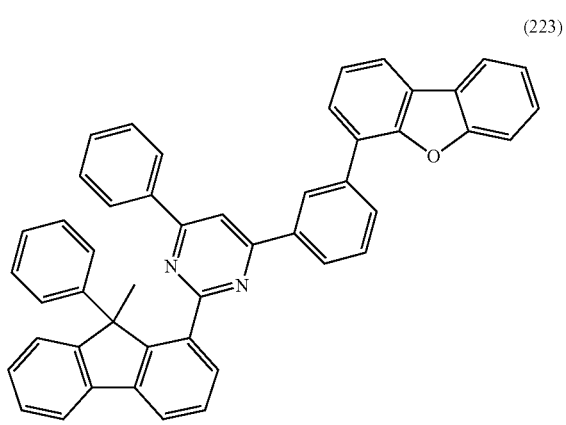
(223)
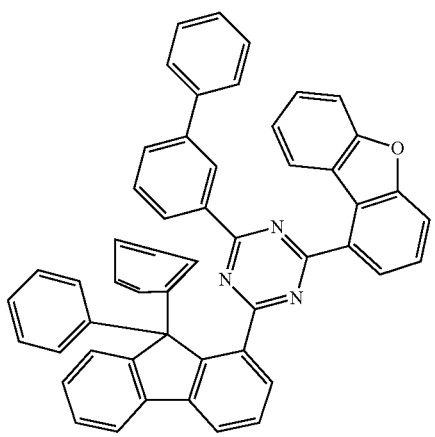
(224)

(225)
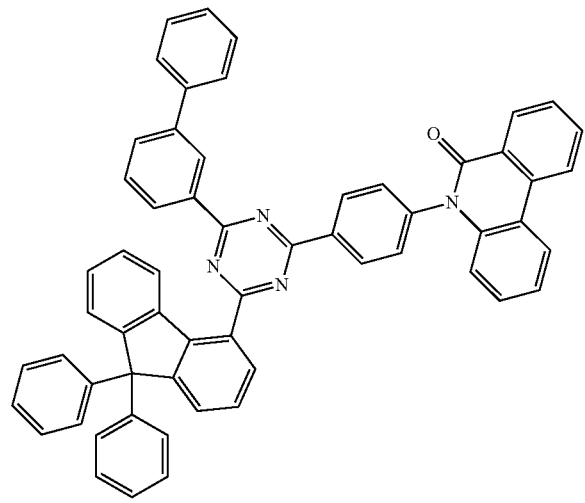
(226)
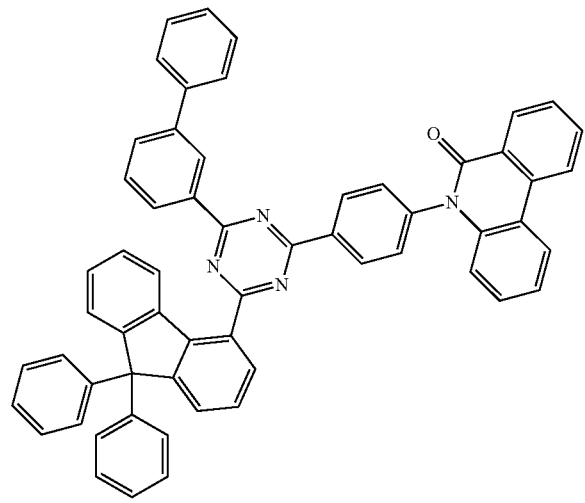
(227)
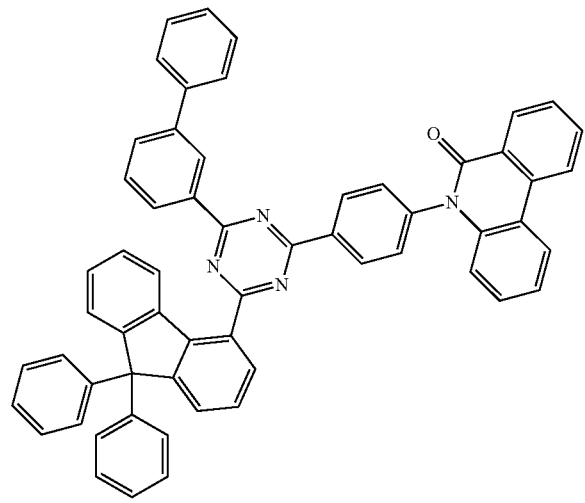
(228)
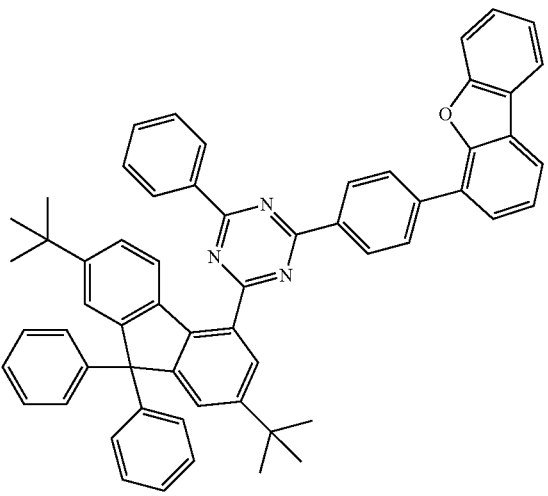
(229)
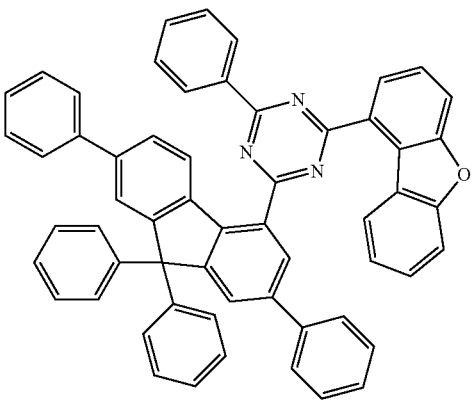
(230)
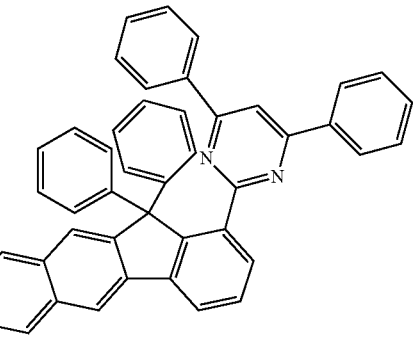
(231)
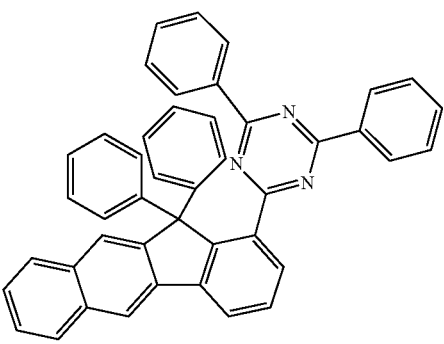

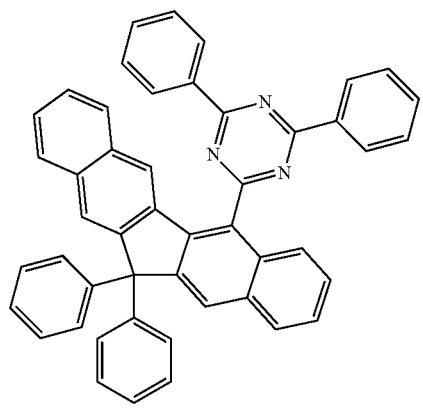
(232)
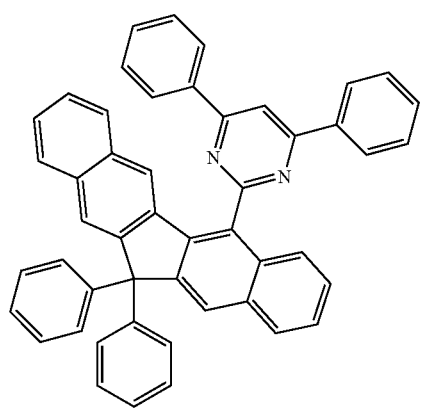
(233)
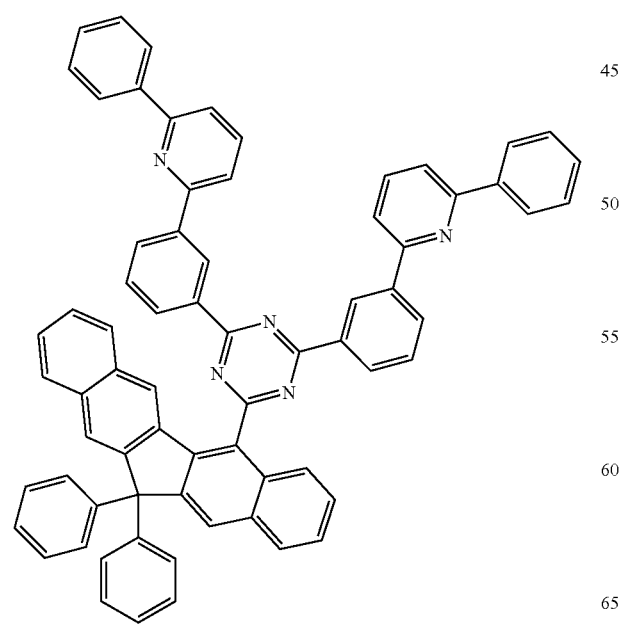
(234)
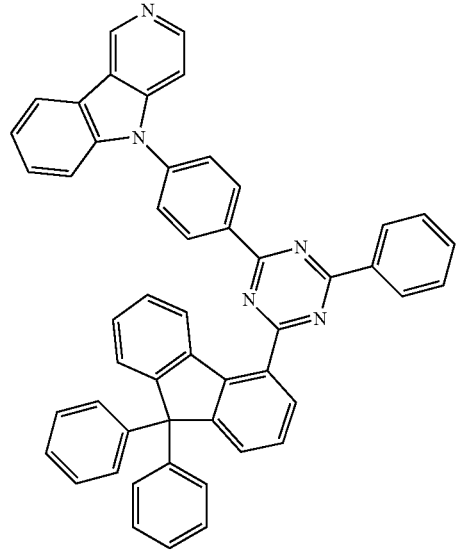
(235)
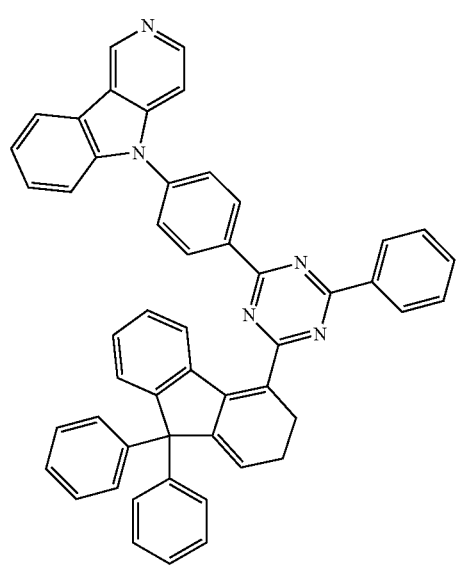
(236)
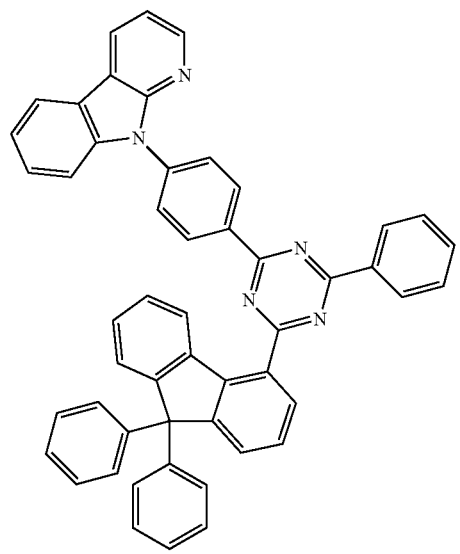
(237)

-continued
(237)
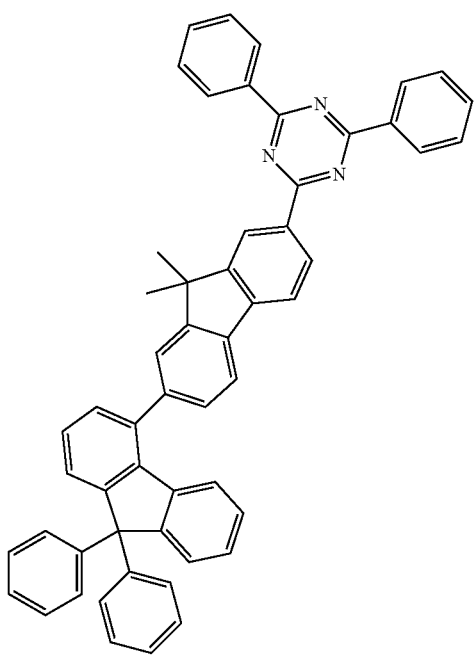
(238)
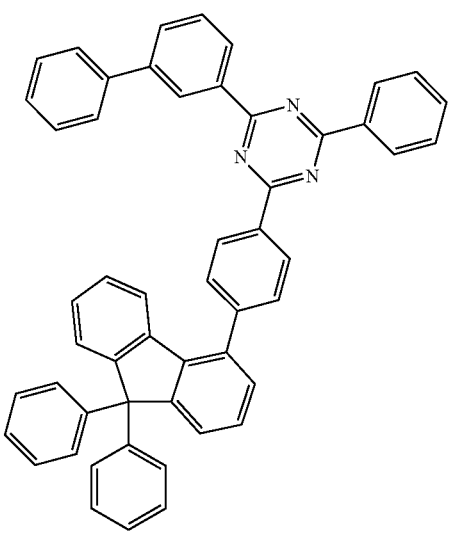
-continued
(239)
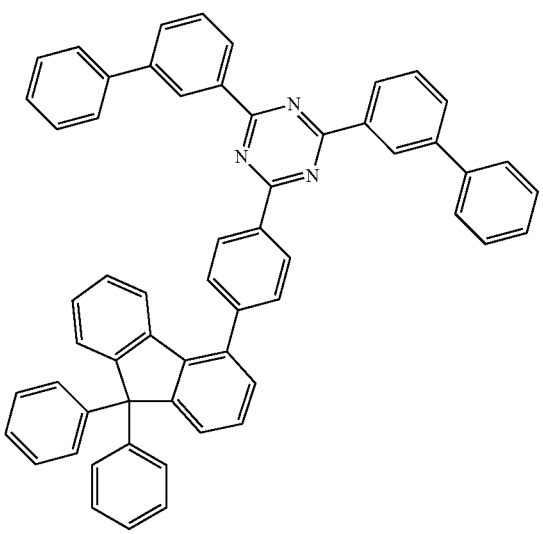
(240)

(241)
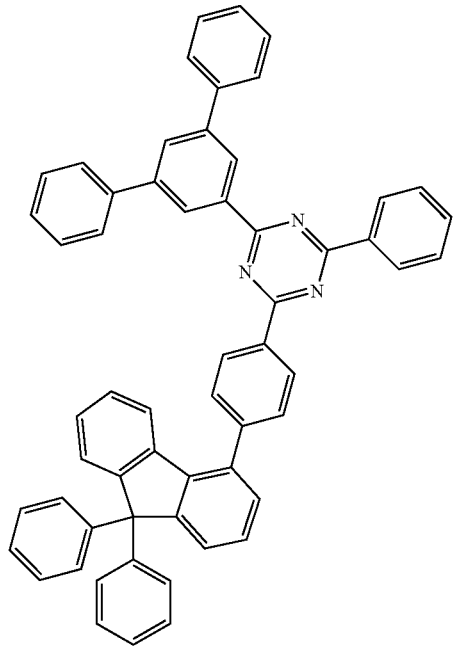
(242)
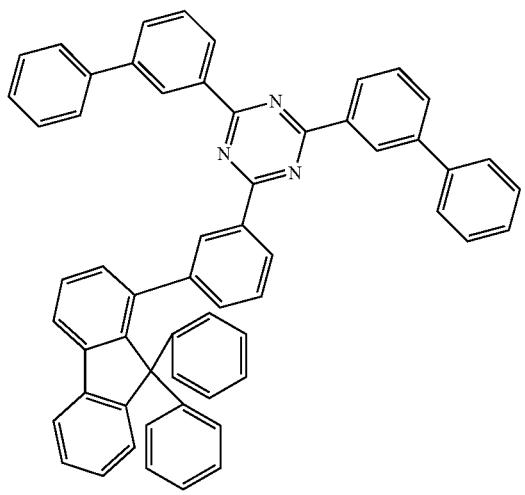
(243)
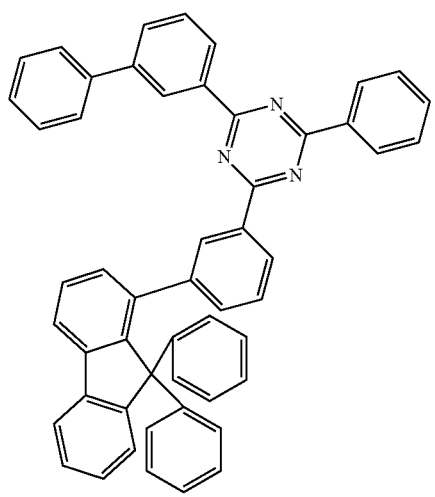
(244)
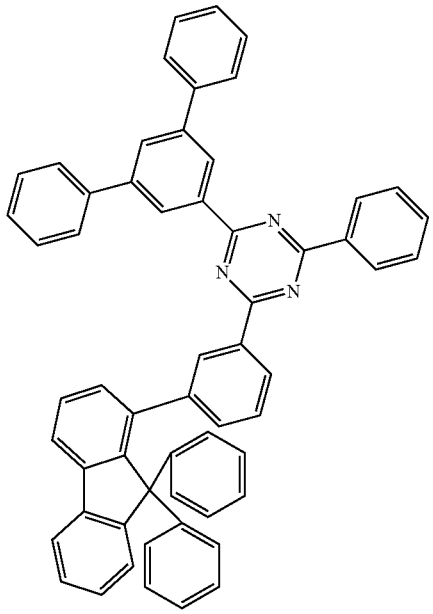
(245)
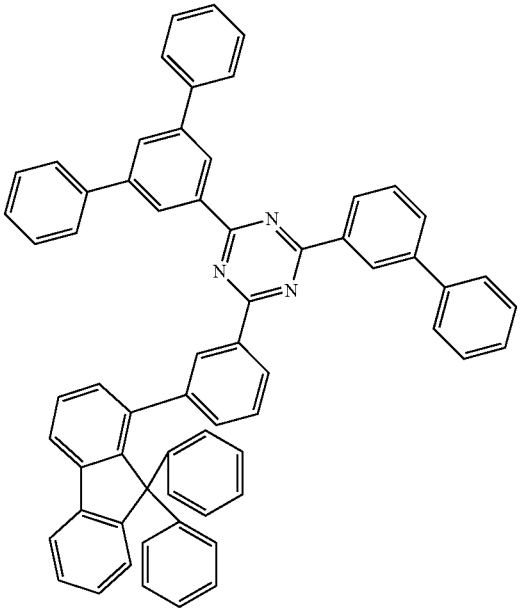

(246)
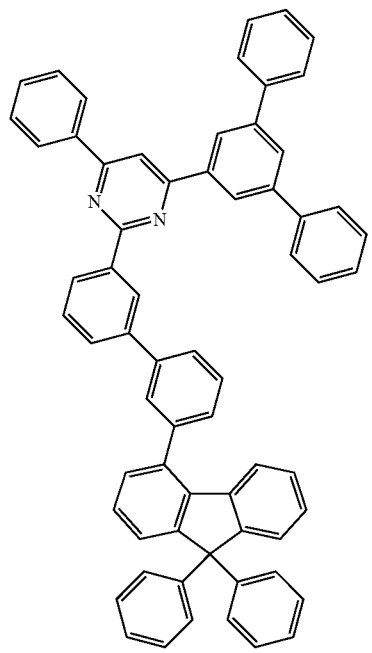
(247)
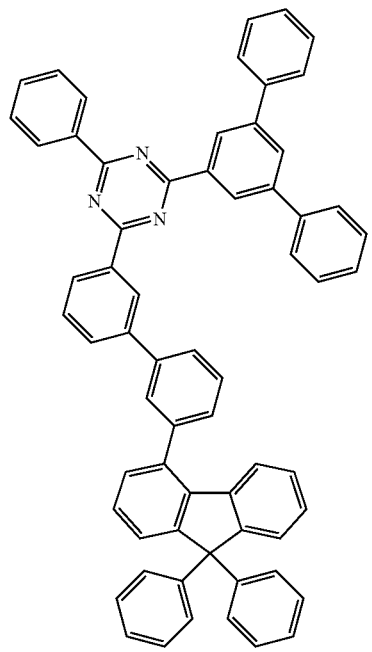
(248)
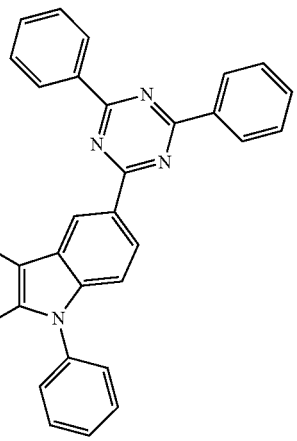
(249)
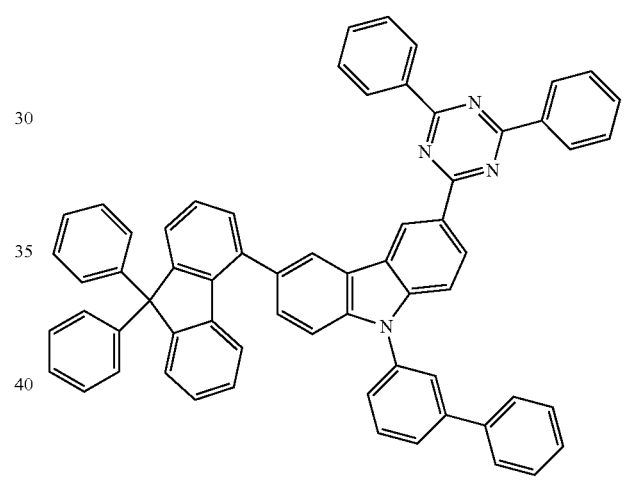
(250)
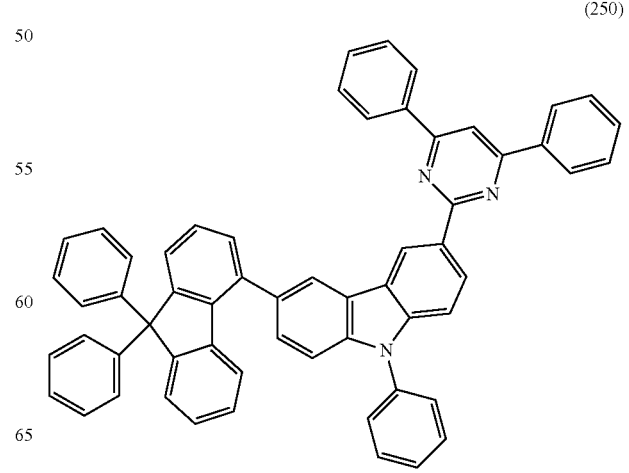

(251)
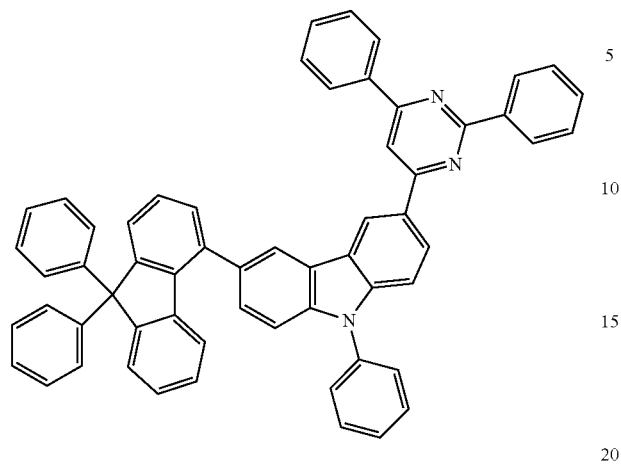
(254)
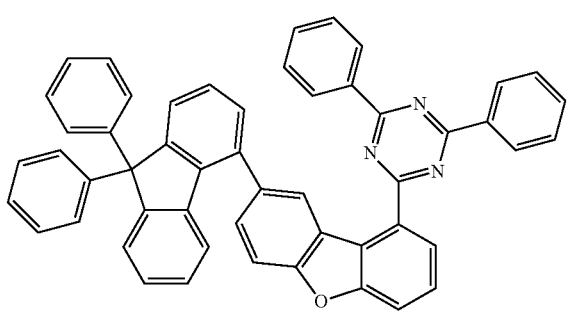
(252)
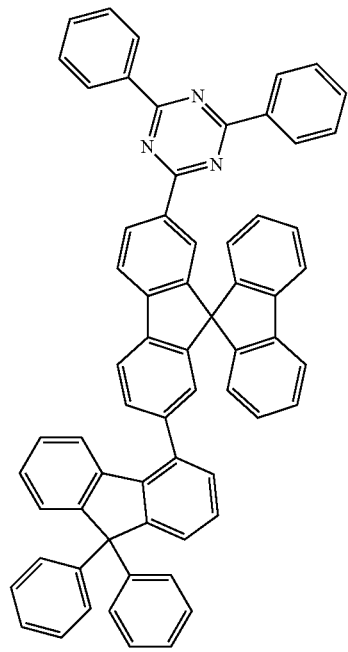
(255)
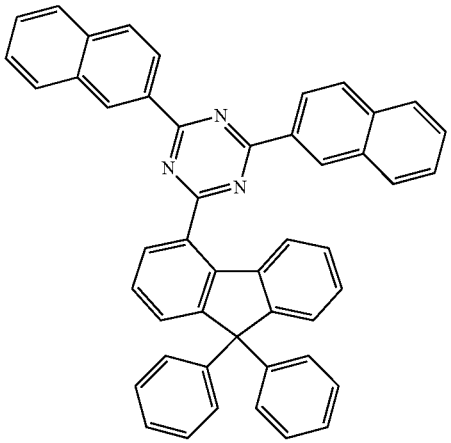
(253)
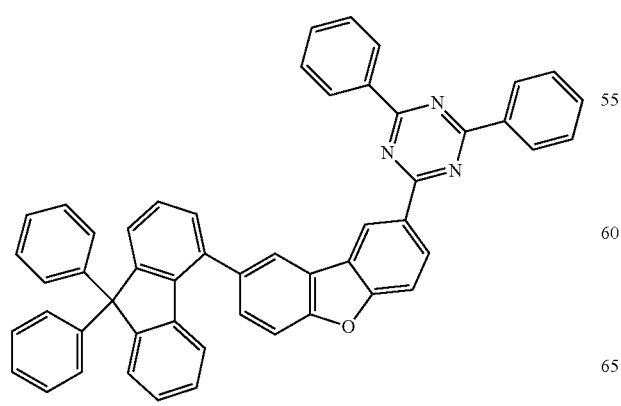
(256)
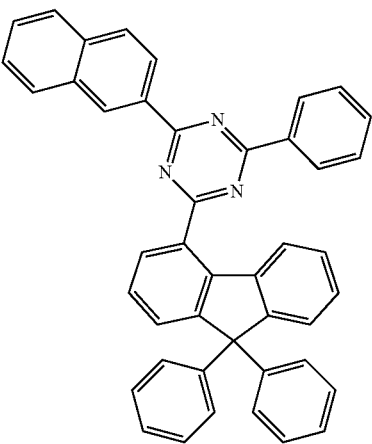

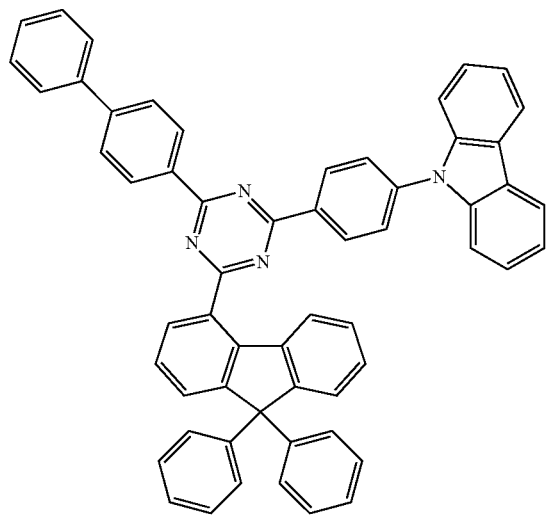
(257)
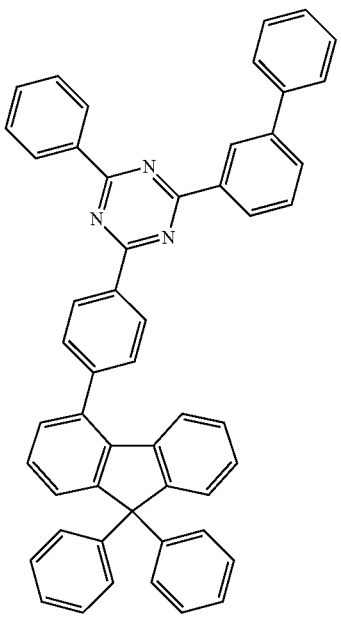
(258)
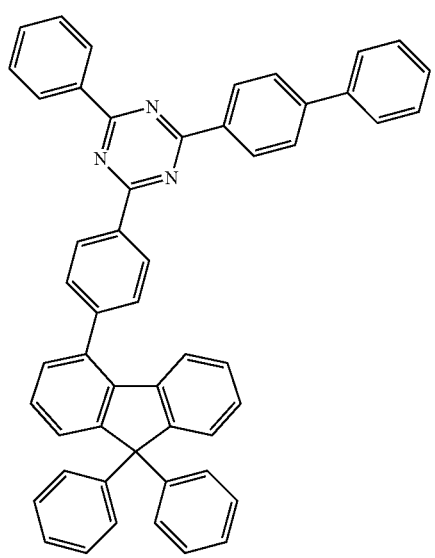
(257)
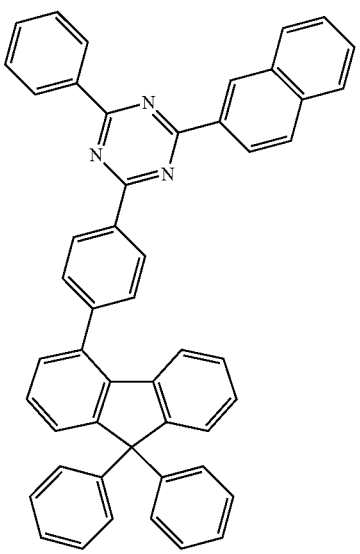
(259)

(260) 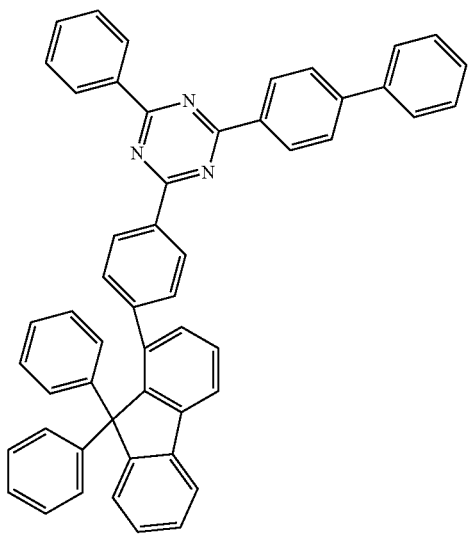
(261) 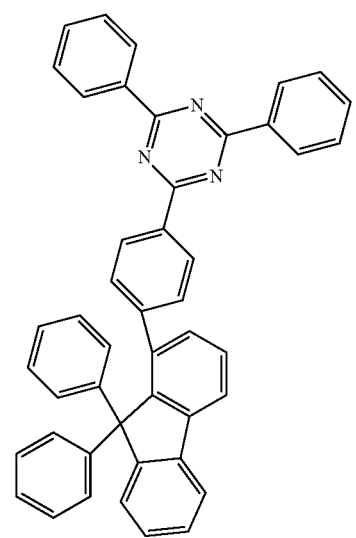
(262) 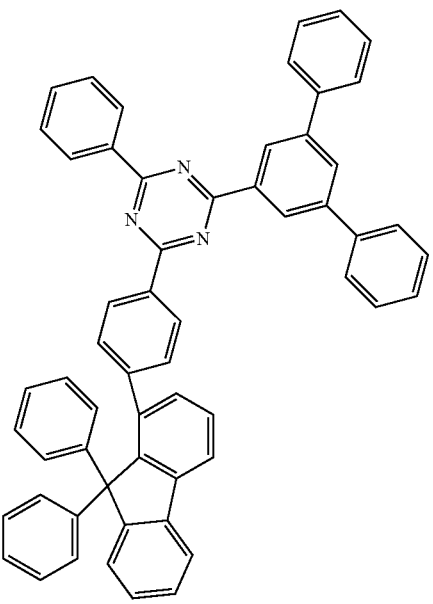
(263) 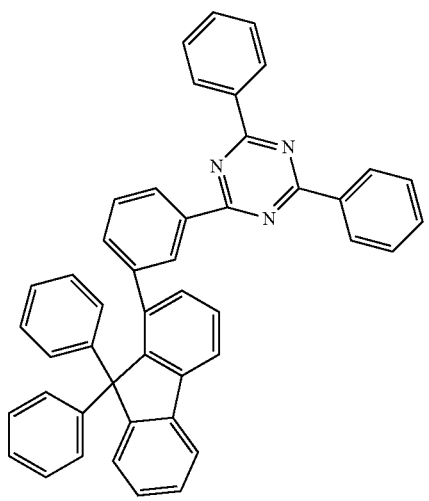
(264) 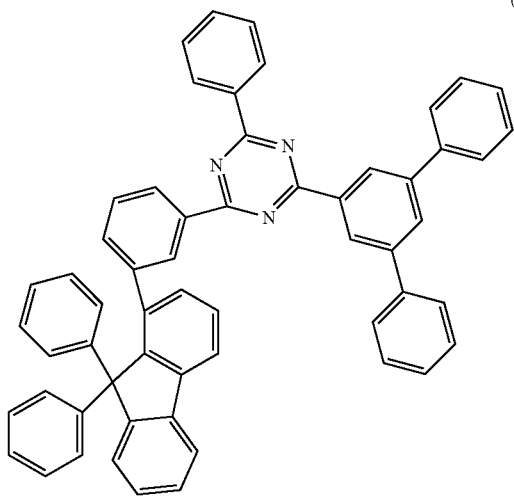

(265)
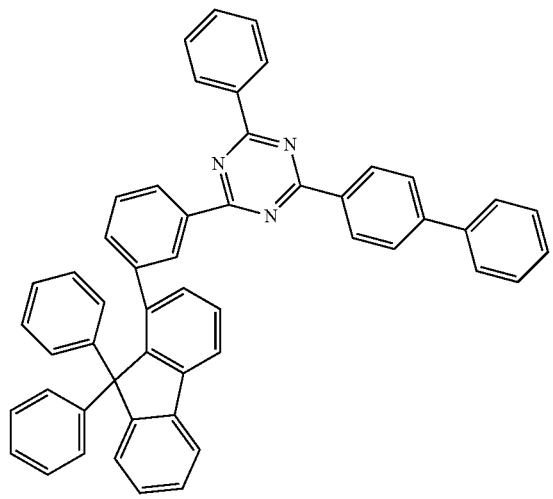
(266)
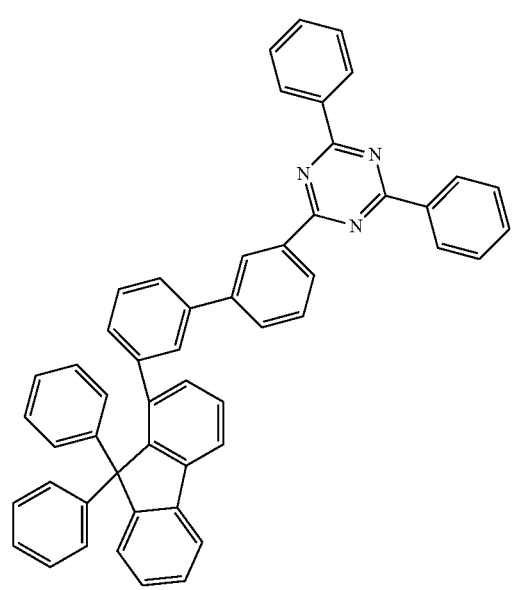
(267)
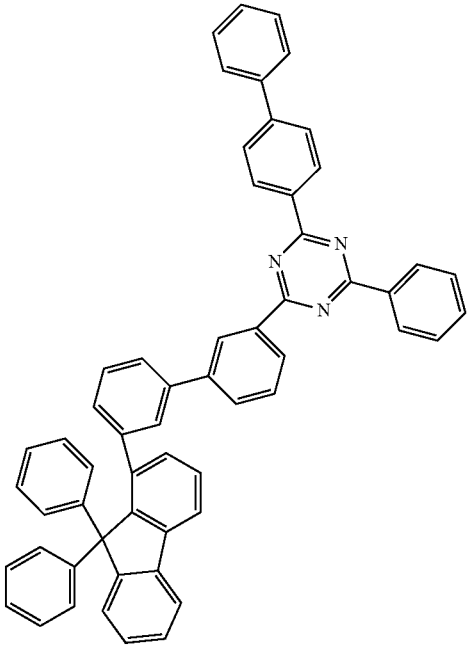
(268)
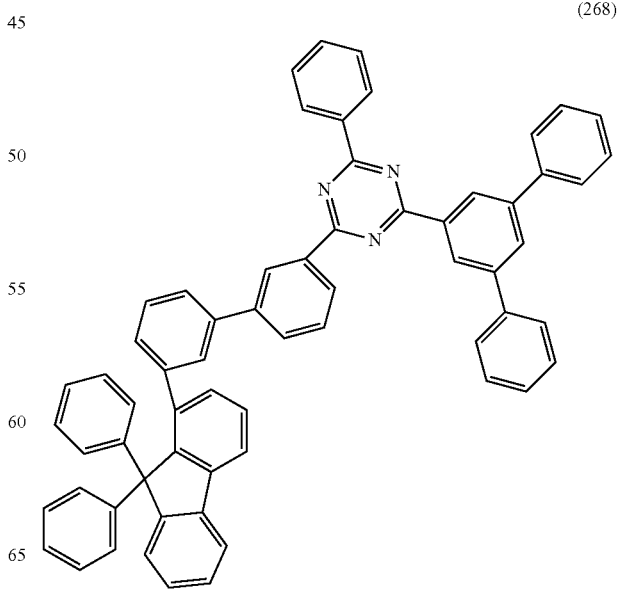

(269)
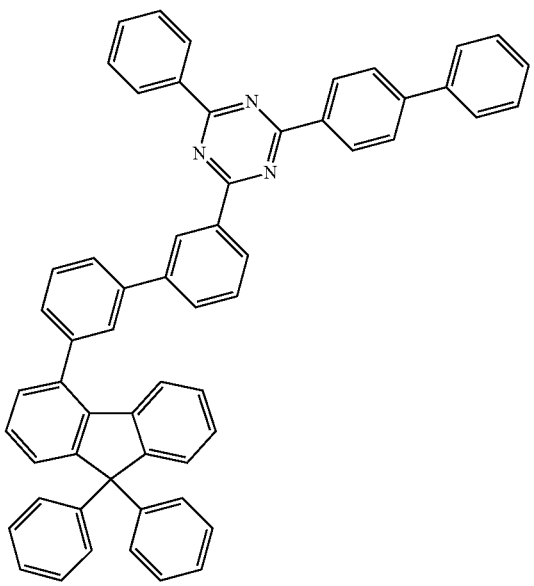
(270)
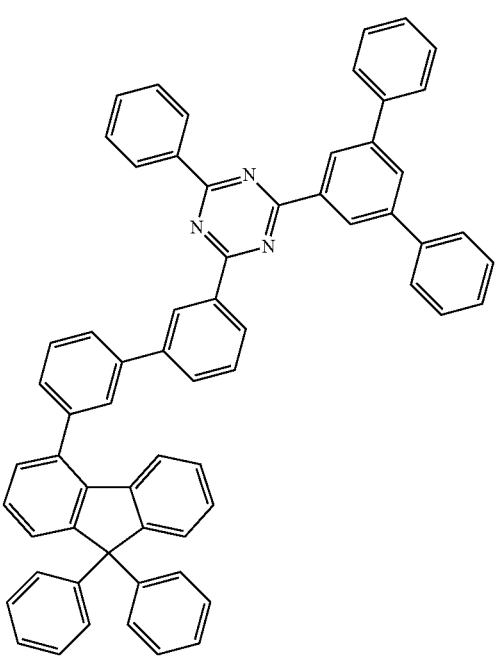
(271)
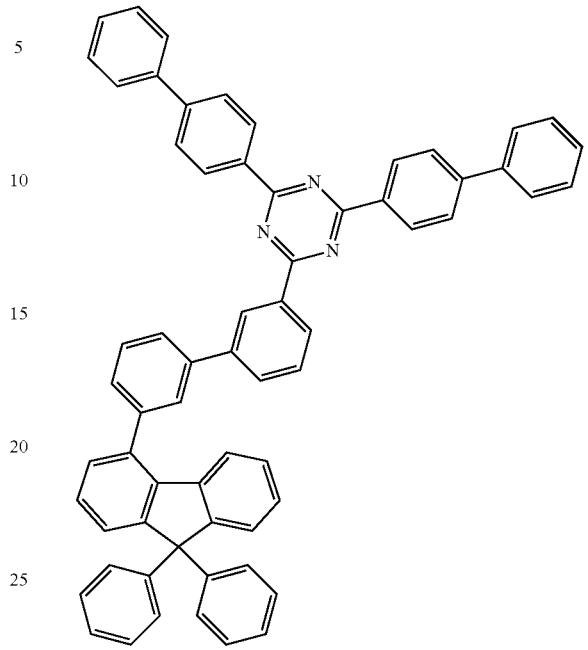
(272)
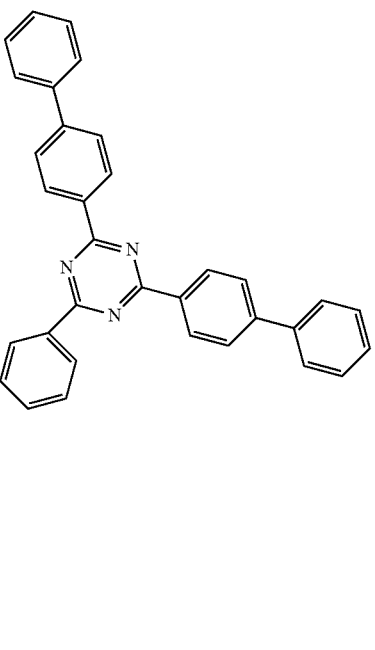

(273)
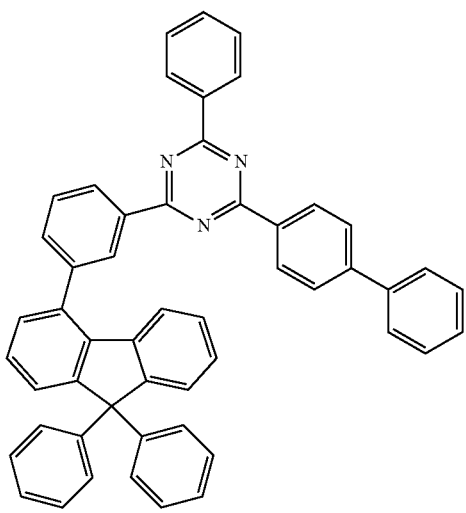

(274)
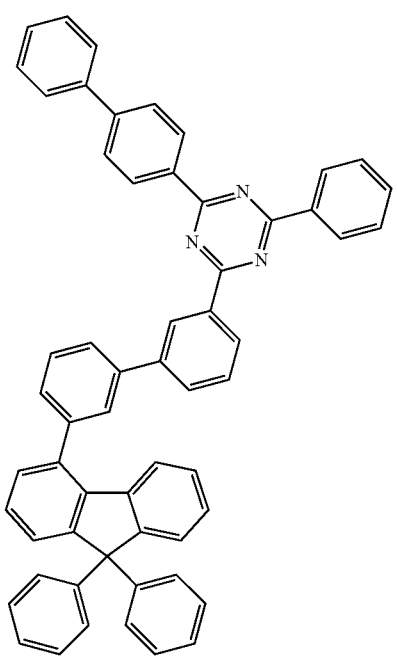

(275)
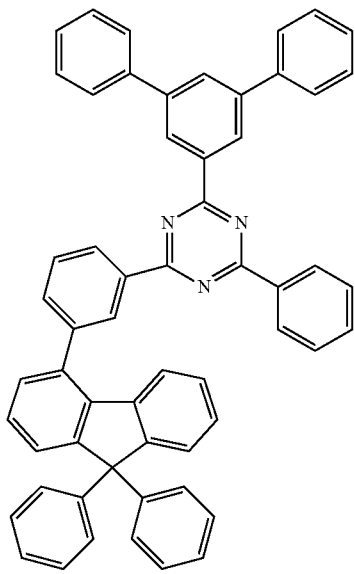

For the processing of the compounds according to the invention from the liquid phase, for example by spin coating or by printing processes, formulations of the compounds according to the invention are necessary. These formulations can be, for example, solutions, dispersions or emulsions. It may be preferred to use mixtures of two or more solvents for this purpose. Suitable and preferred solvents are, for example, toluene, anisole, o-, m- or p-xylene, methyl benzoate, mesitylene, tetraline, veratrole, THF, methyl-THF, THP, chlorobenzene, dioxane, phenoxytoluene, in particular 3-phenoxytoluene, (-)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, hexamethylindane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycoldimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The present invention therefore furthermore relates to a formulation comprising a compound according to the invention and at least one further compound. The further compound may be, for example, a solvent, in particular one of the above-mentioned solvents or a mixture of these solvents. However, the further compound may also be at least one further organic or inorganic compound which is likewise employed in the electronic device, for example an emitting compound and/or a further matrix material. Suitable emitting compounds and further matrix materials are indicated below in connection with the organic electroluminescent device. This further compound may also be polymeric.

The compounds according to the invention are suitable for use in an electronic device, in particular in an organic electroluminescent device. The present invention therefore furthermore relates to the use of a compound according to the invention in an electronic device, in particular in an organic electroluminescent device. The present invention still furthermore relates to an electronic device comprising at least one compound according to the invention.

An electronic device in the sense of the present invention is a device which comprises at least one layer which comprises at least one organic compound. The component may also comprise inorganic materials or also layers which are built up entirely from inorganic materials. The electronic device is preferably selected from the group consisting of organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), dye-sensitised organic solar cells (DSSCs), organic optical detectors, organic photoreceptors, organic field-quench devices (O-FQDs), light-emitting electrochemical cells (LECs), organic laser diodes (O-lasers) and "organic plasmon emitting devices", but preferably organic electroluminescent devices (OLEDs), particularly preferably phosphorescent OLEDs.

The organic electroluminescent device comprises cathode, anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers and/or charge-generation layers. Interlayers, which have, for example, an exciton-blocking function, may likewise be introduced between two emitting layers. However, it should be pointed out that each of these layers does not necessarily have to be present. The organic electroluminescent device here may comprise one emitting layer, or it may comprise a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to systems having two emitting layers, where the two layers exhibit blue and orange or yellow emission, or three emitting layers, where the three layers exhibit blue, green and orange or red emission (for the basic structure see, for example, WO 2005/011013). The organic electroluminescent device according to the invention may also be a tandem OLED, in particular also for white-emitting OLEDs.

The compound according to the invention in accordance with the embodiments indicated above can be employed in various layers of the electronic device, depending on the precise structure. Preference is given to an organic electroluminescent device comprising a compound of the formula (I) or the preferred embodiments indicated above as matrix material for phosphorescent or fluorescent emitters, in particular for phosphorescent emitters, and/or in an electron-blocking or exciton-blocking layer and/or in a charge generation layer and/or in a hole-blocking or electron-transport layer, depending on the precise substitution.

In a preferred embodiment of the invention, the compound according to the invention is employed as matrix material for a phosphorescent compound in an emitting layer. The organic electroluminescent device here may comprise one emitting layer, or it may comprise a plurality of emitting layers, where at least one emitting layer comprises at least one compound according to the invention as matrix material.

If the compound according to the invention is employed as matrix material for a phosphorescent compound in an emitting layer, it is preferably employed in combination with one or more phosphorescent materials (triplet emitters). Phosphorescence in the sense of this invention is taken to mean the luminescence from an excited state having relatively high spin multiplicity, i.e. a spin state >1, in particular from an excited triplet state. In the sense of this application, all luminescent complexes containing transition metals or lanthanides, in particular all iridium, platinum and copper complexes, are to be regarded as phosphorescent compounds.

The mixture of the compound according to the invention and the emitting compound comprises between 99 and 1% by vol., preferably between 98 and 10% by vol., particularly preferably between 97 and 60% by vol., in particular between 95 and 80% by vol., of the compound according to the invention, based on the entire mixture comprising emitter and matrix material. Correspondingly, the mixture comprises between 1 and 99% by vol., preferably between 2 and 90% by vol., particularly preferably between 3 and 40% by vol., in particular between 5 and 20% by vol., of the emitter, based on the entire mixture comprising emitter and matrix material.

A further preferred embodiment of the present invention is the use of the compound according to the invention as matrix material for a phosphorescent emitter in combination with a further matrix material. Particularly suitable matrix materials which can be employed in combination with the compounds according to the invention are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-biscarbazolylbiphenyl) or the carbazole derivatives disclosed in WO 2005/039246, US 2005/0069729, JP 2004/288381, EP 1205527, WO 2008/086851 or WO 2013/041176, indolocarbazole derivatives, for example in accordance with WO 2007/063754 or WO 2008/056746, indenocarbazole derivatives, for example in accordance with WO 2010/136109, WO 2011/000455, WO 2013/041176 or WO 2013/056776, azacarbazole derivatives, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2007/063754, WO 2008/056746, WO 2010/015306, WO 2011/057706, WO 2011/060859 or WO 2011/060877, zinc complexes, for example in accordance with EP 652273 or WO 2009/062578, diazasilole or tetraazasilole derivatives, for example in accordance with WO 2010/054729, diazaphosphole derivatives, for example in accordance with WO 2010/054730, bridged carbazole derivatives, for example in accordance with WO 2011/042107, WO 2011/060867, WO 2011/088877 and WO 2012/143080, or triphenylene derivatives, for example in accordance with WO 2012/048781. A further phosphorescent emitter which emits at shorter wavelength than the actual emitter may likewise be present in the mixture as co-host, or a compound which does not participate in the charge transport to a significant extent, if at all, as described, for example, in WO 2010/108579. It is well within the art to select appropriate matrix materials and emitters for light-emitting layers along with determining the appropriate relative proportions of all the materials present.

Suitable phosphorescent compounds (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80, in particular a metal having this atomic number. The phosphorescence emitters used are preferably compounds which contain copper, molybdenum, tungsten, rhenium, ruthenium, osmium, rhodium, iridium, palladium, platinum, silver, gold or europium, in particular compounds which contain iridium or platinum.

Examples of the emitters described above are revealed by the applications WO 00/70655, WO 2001/41512, WO 2002/02714, WO 2002/15645, EP 1191613, EP 1191612, EP 1191614, WO 2005/033244, WO 2005/019373, US 2005/0258742, WO 2010/086089, WO 2011/157339, WO 2012/007086, WO 2012/163471, WO 2013/000531, WO 2013/020631, WO 2014/008982 and WO 2014/023377. In general, all phosphorescent complexes as are used in accordance with the prior art for phosphorescent OLEDs and as are known to the person skilled in the art in the area of organic electroluminescence are suitable, and the person skilled in the art will be able to use further phosphorescent complexes without inventive step.

The compounds according to the invention are also suitable, in particular, as matrix materials for phosphorescent emitters in organic electroluminescent devices, as described, for example, in US 2011/0248247 and US 2012/0223633. In these multicoloured display components, an additional blue emission layer is applied by vapour deposition over the entire area to all pixels, also those having a colour other than blue. It has been found here, surprisingly, that the compounds according to the invention, when employed as matrix materials for the red and/or green pixels, continue to result in very good emission together with the vapour-deposited blue emission layer.

In a further embodiment of the invention, the organic electroluminescent device according to the invention does not comprise a separate hole-injection layer and/or hole-transport layer and/or hole-blocking layer and/or electron-transport layer, i.e. the emitting layer is directly adjacent to the hole-injection layer or the anode, and/or the emitting layer is directly adjacent to the electron-transport layer or the electron-injection layer or the cathode, as described, for example, in WO 2005/053051. It is furthermore possible to use a metal complex which is the same as or similar to the metal complex in the emitting layer as hole-transport or hole-injection material directly adjacent to the emitting layer, as described, for example, in WO 2009/030981.

In a further embodiment of the invention, the compound according to the invention is employed in an exciton-blocking layer.

In still a further preferred embodiment of the invention, the compound according to the invention is employed as electron-transport material in an electron-transport or electron-injection layer. The emitting layer here may be fluorescent or phosphorescent. If the compound is employed as electron-transport material, it may be preferred for it to be doped, for example with alkali metals or alkali-metal complexes, such as, for example, Li or LiQ (lithium hydroxyquinolinate).

In still a further preferred embodiment of the invention, the compound according to the invention is employed in a hole-blocking layer. A hole-blocking layer is taken to mean a layer which is directly adjacent to an emitting layer on the cathode side. Another preferred embodiment is employing the compound as part of a charge generation layer. A charge generation layer (CGL) works as an injector of an electron-hole pair upon voltage application and is well-known in the art. Generally, a CGL consists of a electron-rich layer (for example, a n-doped electron transporting layer) adjacent to an electron-poor layer (for example, a p-doped hole transporting layer). However, in some cases, the CGL can be only a single layer. In other cases, one or both layers of the CGL may or may not be doped.

In the further layers of the organic electroluminescent device according to the invention, all materials can be used as are usually employed in accordance with the prior art. The person skilled in the art will therefore be able to employ all materials which are known for organic electroluminescent devices in combination with the compounds of the formula (I) according to the invention or the preferred embodiments indicated above without inventive step.

Preference is furthermore given to an organic electroluminescent device, characterised in that one or more layers are coated by means of a sublimation process, in which the materials are applied by vapour deposition in vacuum sublimation units at an initial pressure of less than $10^{-5}$ mbar, preferably less than $10^{-6}$ mbar. However, it is also possible for the initial pressure to be even lower, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, offset printing, LITI (light induced thermal imaging, thermal transfer printing), inkjet printing or nozzle printing. Soluble compounds, which are obtained, for example, by suitable substitution, are necessary for this purpose.

Also possible are hybrid processes, in which, for example, one or more layers are applied from solution and one or more further layers are applied by vapour deposition. These processes are generally known to the person skilled in the art and can be applied by him without inventive step to organic electroluminescent devices comprising the compounds according to the invention.

The compounds according to the invention and the organic electroluminescent devices according to the invention are distinguished by one or more of the following surprising advantages over the prior art:

1. The compounds according to the invention, employed as matrix material for fluorescent or phosphorescent emitters, result in long lifetimes. This applies, in particular, if the compounds are employed as matrix material for a phosphorescent emitter.
2. The compounds according to the invention result in very high efficiency. This applies, in particular, if the compounds are employed as matrix material for a phosphorescent emitter or as a hole-blocking material.
3. In some embodiments, the compounds according to the invention result in low voltage devices. This applies, in particular, if the compounds are employed as matrix material for a phosphorescent emitter or in an electron-transport layer.

These above-mentioned advantages are not accompanied by an impairment in the other electronic properties.

The invention is explained in greater detail by the following examples without wishing to restrict it thereby. The person skilled in the art will be able to use the descriptions to carry out the invention throughout the range disclosed and prepare further compounds according to the invention without inventive step and use them in electronic devices or apply the process according to the invention.

EXAMPLES

Synthesis Examples

The following syntheses are carried out, unless indicated otherwise, under a protective-gas atmosphere in dried solvents. The solvents and reagents can be purchased from ALDRICH or ABCR. The numbers indicated in the case of the starting materials which are commercially available are the corresponding CAS numbers.

The materials of the invention can generally be prepared according to the following synthetic scheme 1 (Note: In Scheme 1, two or three X will be N and for when there are two nitrogens, the other X will be $CR_1$ and $R_3$ is preferably, but is not limited to, the fluorene skeleton; in some embodiments, the fluorene skeleton may be added in step 1 or 2a/b):

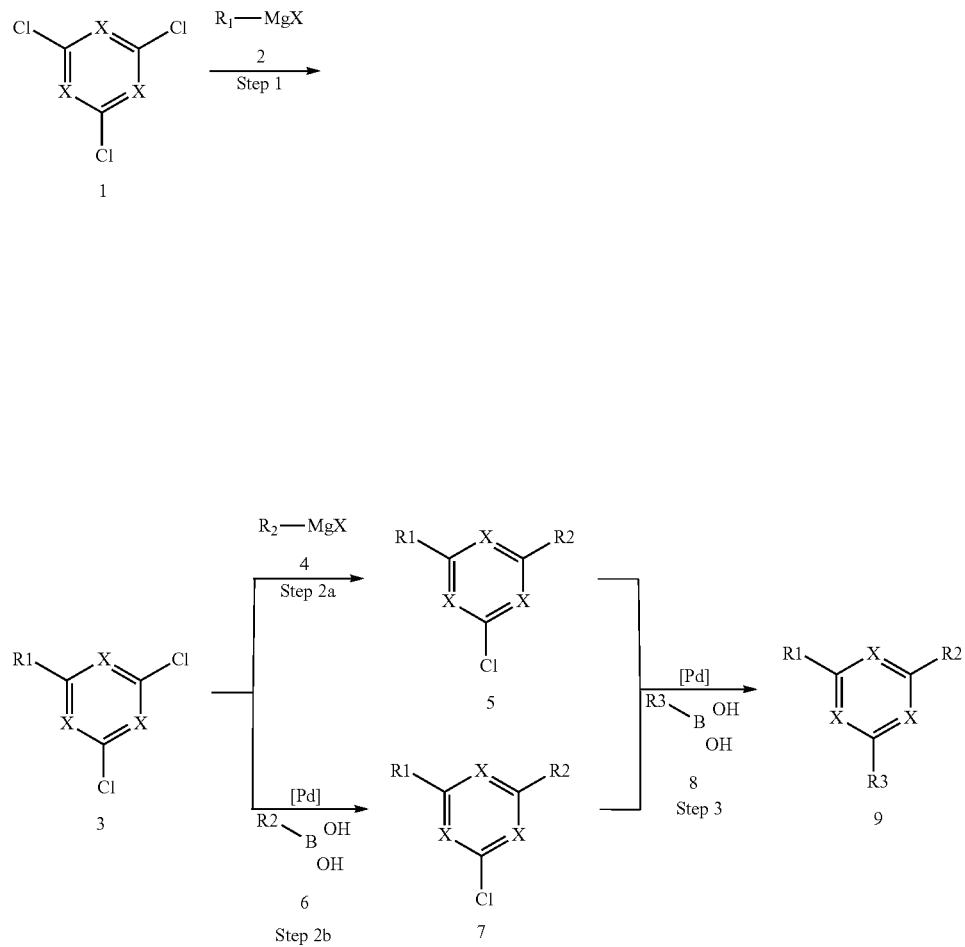

Step 1:

295 g (1.6 mol, 1.0 eq) of 2,4,6-trichloro-1,3,5-triazine [108-77-0] 1 are solved in 800 ml dried THF in a four-necked flask under an inert atmosphere. The solution is cooled with an ice bath to about 0° C. and 800 ml (1.6 mol, 1.0 eq) of a 2 mol/l phenylmagnesiumchloride solution are added slowly to maintain the temperature below 10° C. Then, the mixture is stirred at room temperature overnight and after the reaction had finished, 800 ml of toluene and 1.2 L of HCl 2% are added. The organic phase is separated, extracted three times with water and dried over sodium sulfate. The solvent is evaporated under reduced pressure until the product precipitates. After washing the solid with ethanol, 242 g (1.1 mol, 67%) of the desired product 3a are obtained.

Other examples are obtained analogously:

| Cmpd. | Reactant 1 | Reactant 2 | Product 3 | Yield [%] |
|---|---|---|---|---|
| 3a | [108-77-0] | | | 67 |
| 3b | [108-77-0] | [103068-18-4] | | 74 |
| 3c | [108-77-0] | 2.0 eq [103068-18-4] | | 89 |
| 3d | [108-77-0] | [247575-72-0] | | 62 |

-continued

| Cmpd. | Reactant 1 | Reactant 2 | Product 3 | Yield [%] |
|---|---|---|---|---|
| 3e | Cl-triazine-Cl, Cl [108-77-0] | 9-phenylcarbazol-3-yl-MgBr [1329630-15-0] | 9-phenyl-3-(4,6-dichloro-1,3,5-triazin-2-yl)carbazole | 45 |
| 3f | 2,4,6-trichloropyrimidine [3764-01-1] | 3-biphenyl-MgBr 2.0 eq [103068-18-4] | 4,6-bis(3-biphenyl)-2-chloropyrimidine | 86 |
| 3g | 2,4,6-trichloropyrimidine [3764-01-1] | 4-biphenyl-MgBr [3315-91-1] | 4,6-bis(4-biphenyl)-2-chloropyrimidine | 81 |
| 3h | 2,4,6-trichloropyrimidine [3764-01-1] | 4-(1-naphthyl)phenyl-MgBr 2.0 eq [1195975-06-4] | 4,6-bis(4-(1-naphthyl)phenyl)-2-chloropyrimidine | 65 |

Step 2a:

1.5 g (61 mmol, 1.12 eq) of magnesium turnings are heated in a four-necked flask for a few minutes. Then, a few ml of 19 g (60 mmol, 1.10 eq) of 1-Bromo-3,5-diphenyl-benzene [103068-20-8] in 100 ml dried THF were added until the Grignard reaction starts. Then, the solution was added slowly to maintain the Grignard reaction at reflux. After the addition is complete, the mixture was cooled to about 0° C. with an ice bath. In a second apparatus, 12.3 g (54 mmol, 1.0 eq) 2,4-dichloro-6-phenyl-[1,3,5]-triazine 3a are solved in 60 ml dried THF and cooled with an ice bath. The Grignard reagent was transferred into a dropping funnel and slowly added to the solution of 3a. After stirring over night at room temperature, the mixture was diluted with 100 ml THF and 50 ml of a 1 M HCl are added. The formed precipitate is washed with water, ethanol and heptane. After purification by hot extraction from toluene 16 g (39 mmol, 72%) of the desired product 5a are obtained.

Other examples are obtained analogously

| Cmpd. | Reactant 3 | Reactant 4 | Product 5 | Yield [%] |
|---|---|---|---|---|
| 5a | 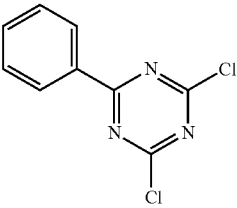 [SMILES: Clc1nc(Cl)nc(-c2ccccc2)n1] | 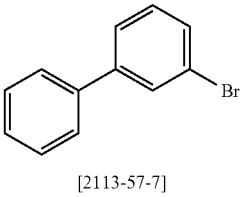 [SMILES: Brc1cccc(-c2ccccc2)c1] [2113-57-7] | 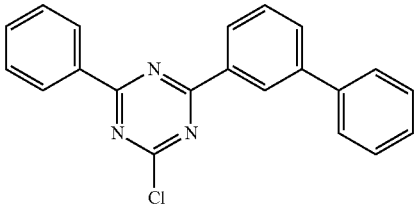 [SMILES: Clc1nc(-c2ccccc2)nc(-c2cccc(-c3ccccc3)c2)n1] | 71 |
| 5b | 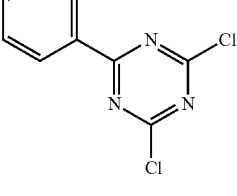 | 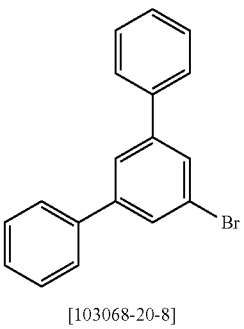 [SMILES: Brc1cc(-c2ccccc2)cc(-c2ccccc2)c1] [103068-20-8] | 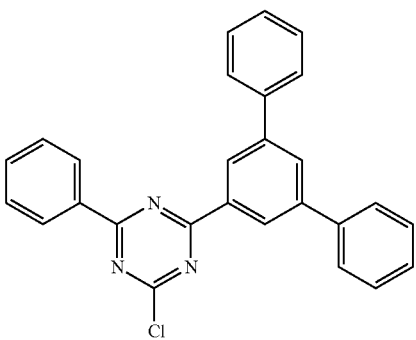 [SMILES: Clc1nc(-c2ccccc2)nc(-c2cc(-c3ccccc3)cc(-c3ccccc3)c2)n1] | 65 |
| 5c | 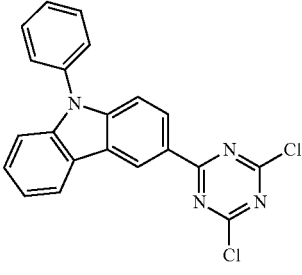 [SMILES: Clc1nc(Cl)nc(-c2ccc3c(c2)c2ccccc2n3-c2ccccc2)n1] | 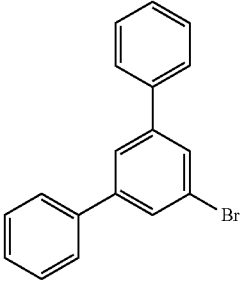 [103068-20-8] | 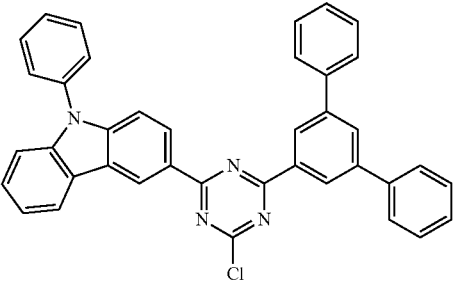 [SMILES: Clc1nc(-c2cc(-c3ccccc3)cc(-c3ccccc3)c2)nc(-c2ccc3c(c2)c2ccccc2n3-c2ccccc2)n1] | 62 |
| 5d | 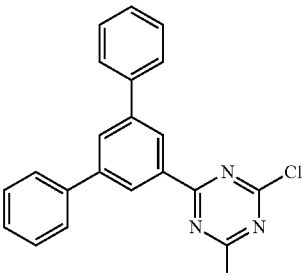 | 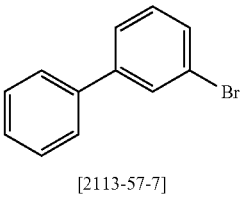 [SMILES: Brc1cccc(-c2ccccc2)c1] [2113-57-7] | 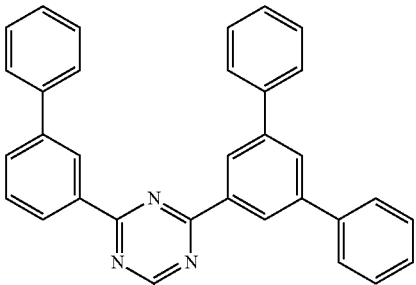 | 83 |

Step 2b:

35 g (150 mmol, 1.0 eq) 2,4-Dichloro-6-phenyl-[1,3,5]triazine, 35 g (150 mmol, 1.0 eq) dibenzothiophene-4-boronic acid [108847-20-7] and 18 g (170 mmol, 1.10 eq) sodium carbonate are dissolved in 300 ml 1,4-dioxane, 300 ml water and 120 ml toluene under an inert atmosphere. Then, 1.8 g (1.5 mmol, 0.01 eq) tetrakis(triphenylphosphine) palladium is added and the mixture refluxed over night at 110° C. After the reaction is completed, 100 ml water are added and the precipitated (48 g) solid is filtered. The organic layer is separated, washed with water and dried over sodium sulfate. After evaporation of the solvent, another 13 g of the crude product are obtained. The combined solids are recrystallized twice from toluene to give 32 g (86 mmol, 56%) of the desired product 7a.

Other examples are obtained analogously

| Cmpd. | Reactant 3 | Reactant 6 | Product 7 | Yield [%] |
|---|---|---|---|---|
| 7a | 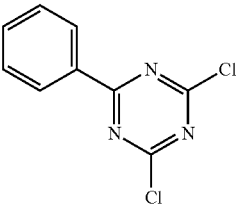 [SMILES: Clc1nc(Cl)nc(-c2ccccc2)n1] | 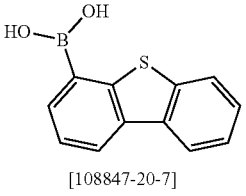 [SMILES: OB(O)c1cccc2c1sc1ccccc12] [108847-20-7] | 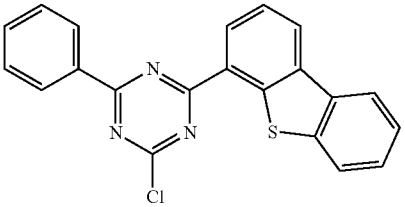 [SMILES: Clc1nc(-c2ccccc2)nc(-c2cccc3c2sc2ccccc23)n1] | 65 |
| 7b | 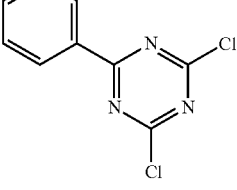 | 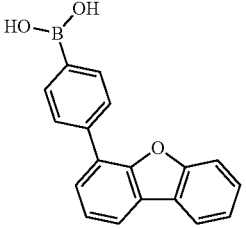 [796071-96-0] | 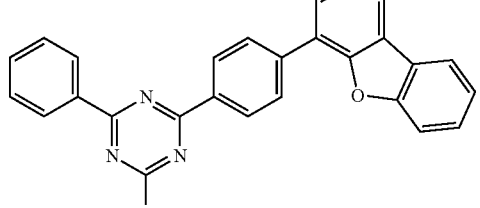 | 76 |
| 7c | 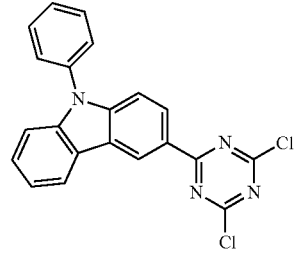 [SMILES: Clc1nc(Cl)nc(-c2ccc3c(c2)c2ccccc2n3-c2ccccc2)n1] | 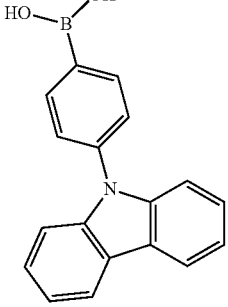 [419536-33-7] | 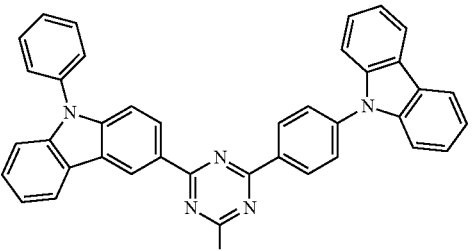 | 45 |
| 7d | 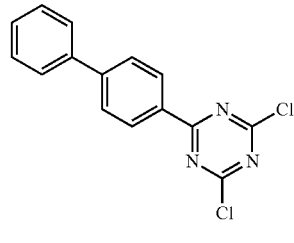 [SMILES: Clc1nc(Cl)nc(-c2ccc(-c3ccccc3)cc2)n1] | 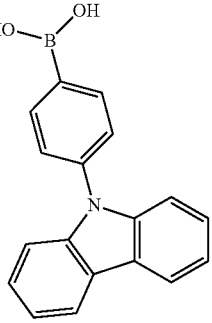 [419536-33-7] | 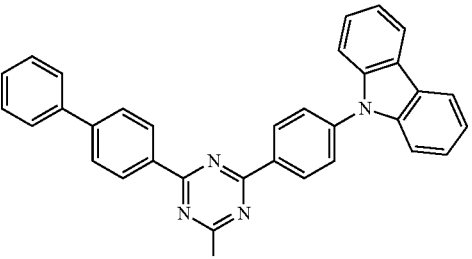 | 62 |

-continued
| Cmpd. | Reactant 3 | Reactant 6 | Product 7 | Yield [%] |
|---|---|---|---|---|
| 7e | 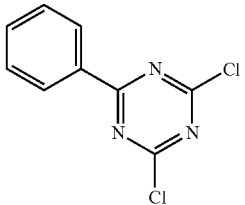 [SMILES: Clc1nc(Cl)nc(-c2ccccc2)n1] | 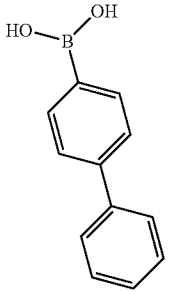
[170230-28-1] | 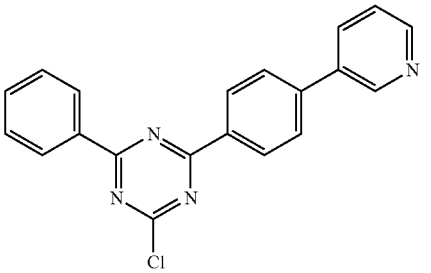 [SMILES: Clc1nc(-c2ccccc2)nc(-c2ccc(-c3cccnc3)cc2)n1] | 71 |
| 7f | 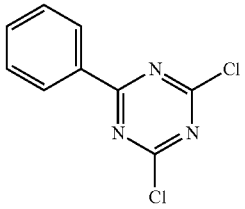 [SMILES: Clc1nc(Cl)nc(-c2ccccc2)n1] | 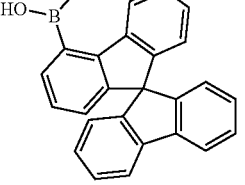
[1421789-05-0] | 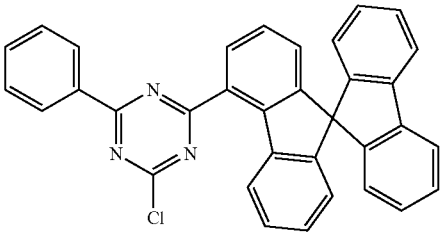 [SMILES: Clc1nc(-c2ccccc2)nc(-c2cccc3c2-c2ccccc2C32c3ccccc3-c3ccccc32)n1] | 39 |
| 7g | 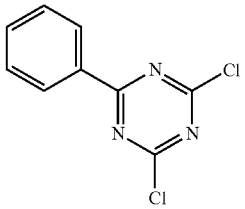 [SMILES: Clc1nc(Cl)nc(-c2ccccc2)n1] | 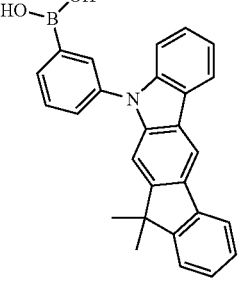
[1369587-64-3] | 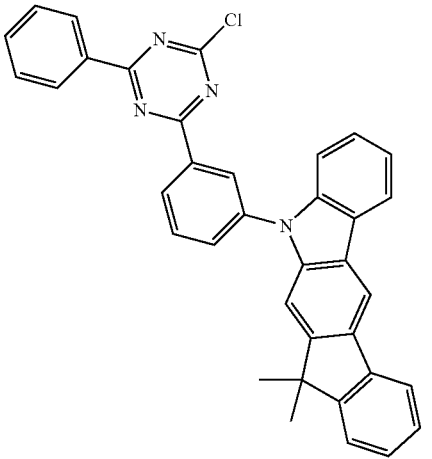 [SMILES: CC1(C)c2ccccc2-c2cc3c4ccccc4n(-c4cccc(-c5nc(Cl)nc(-c6ccccc6)n5)c4)c3cc21] | 46 |
| 7h | 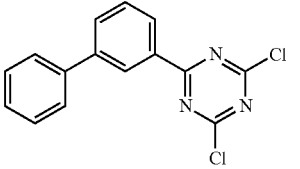 [SMILES: Clc1nc(Cl)nc(-c2cccc(-c3ccccc3)c2)n1] | 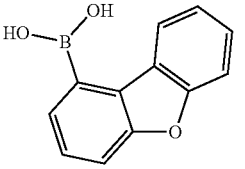
[262607-19-4] | 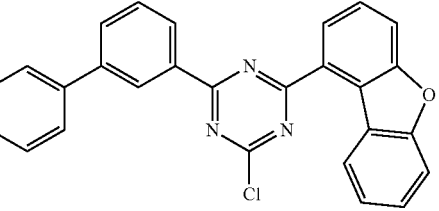 | 68 |

-continued

| Cmpd. | Reactant 3 | Reactant 6 | Product 7 | Yield [%] |
|---|---|---|---|---|
| 7i | 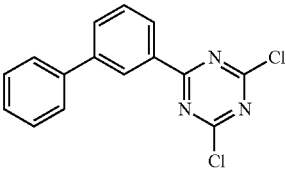 [SMILES: Clc1nc(Cl)nc(-c2cccc(-c3ccccc3)c2)n1] | 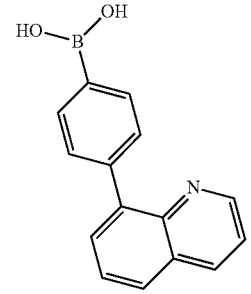 [1233131-18-4] | 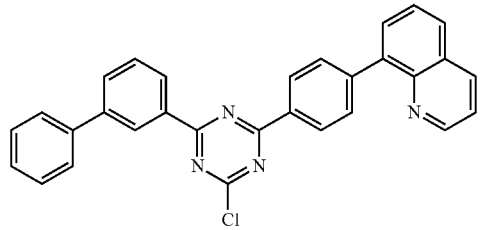 [SMILES: Clc1nc(-c2ccc(-c3cccc4cccnc34)cc2)nc(-c2cccc(-c3ccccc3)c2)n1] | 77 |
| 7j | 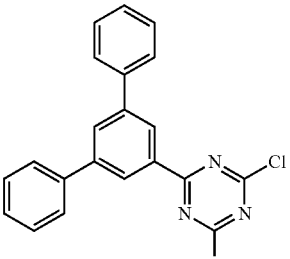 | 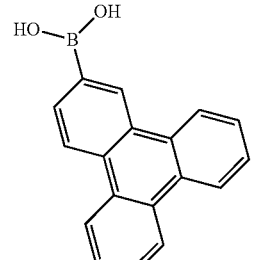 [654664-63-8] | 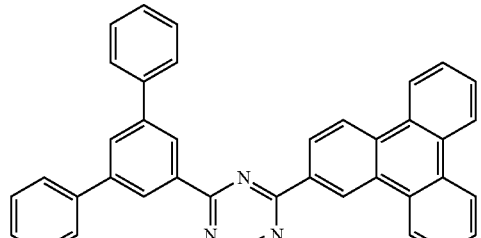 | 62 |

Step 3b:

30 g (80 mmol, 1.0 eq) of 7a, 21 g (88 mmol, 1.1 eq) 9,9-Dimethyl-9H-fluoren-4-yl-boronic acid [1246022-50-3] and 17 g (160 mmol, 2.0 eq) sodium carbonate are dissolved in 400 ml toluene, 250 ml water and 170 ml ethanol under an inert atmosphere. Then, 0.93 g (0.80 mmol, 0.01 eq) tetrakis(triphenylphosphine)palladium is added and the mixture refluxed over night at 110° C. After the reaction is completed, 300 ml water were added and the precipitated (36 g) solid is filtered. The organic layer is separated, washed with water and dried over sodium sulfate. After evaporation of the solvent, another 5.1 g of the crude product are obtained. The combined solids are purified by hot extraction from toluene/heptane, recrystallized twice from toluene/heptane and sublimed to give 20 g (38 mmol, 47%) of the desired product 9a.

Other examples are obtained analogously:

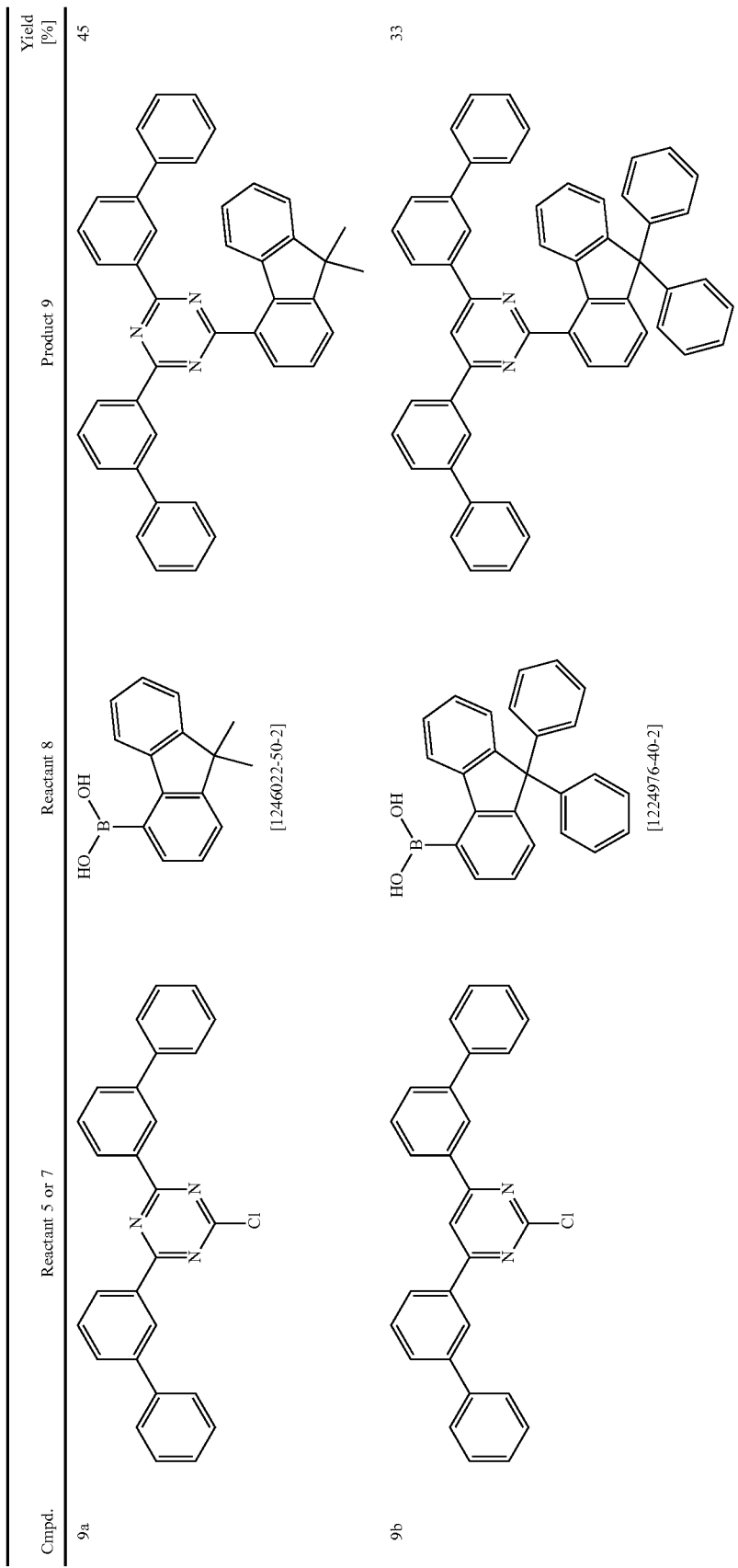

-continued

| Cmpd. | Reactant 5 or 7 | Reactant 8 | Product 9 | Yield [%] |
|---|---|---|---|---|
| 9c | | [1246022-50-2] | | 56 |
| 9d | | [1246022-50-2] | | 31 |

| Cmpd. | Reactant 5 or 7 | Reactant 8 | Product 9 | Yield [%] |
|---|---|---|---|---|
| 9e | 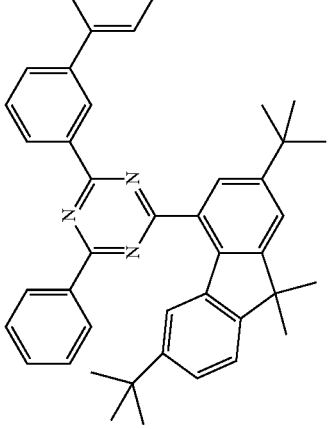 | 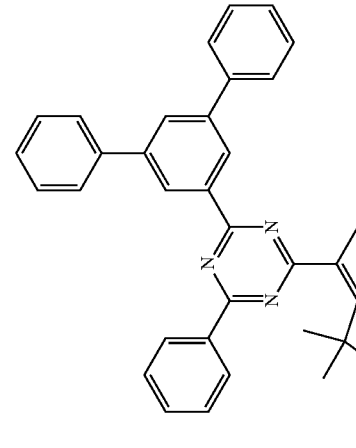 [1092576-56-1] | 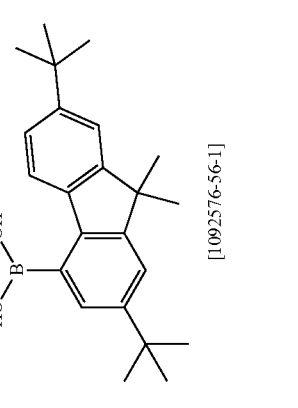 | 28 |
| 9f | 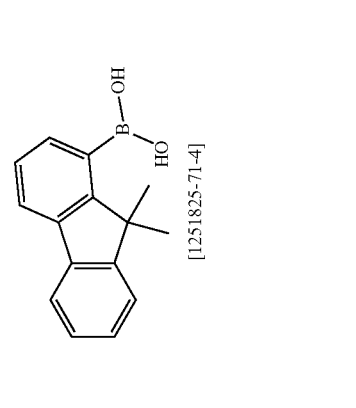 | 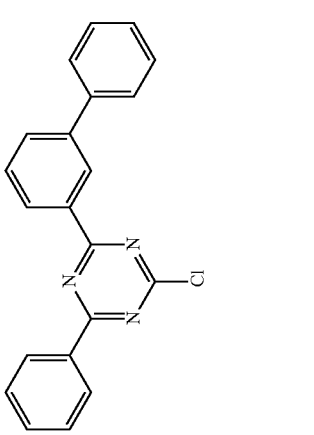 [1251825-71-4] | 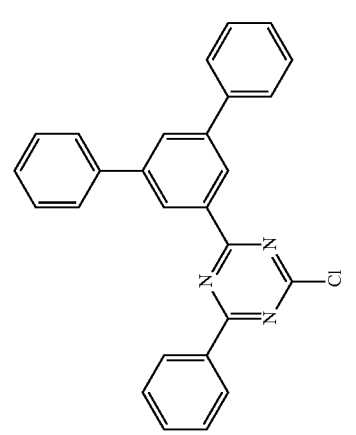 | 55 |

| Cmpd. | Reactant 5 or 7 | Reactant 8 | Product 9 | Yield [%] |
|---|---|---|---|---|
| 9g | 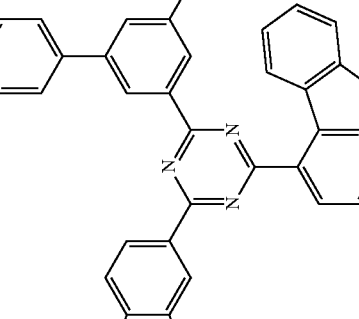 | 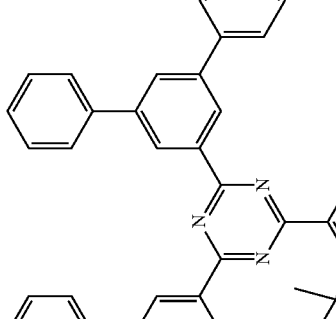 [1246022-50-2] | 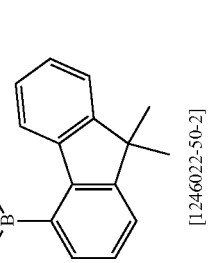 | 67 |
| 9h | 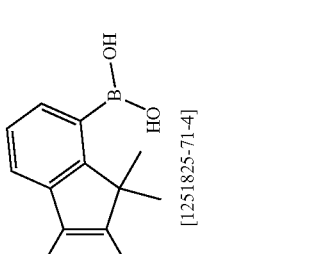 | 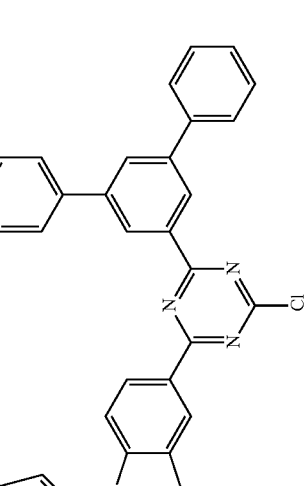 [1251825-71-4] | 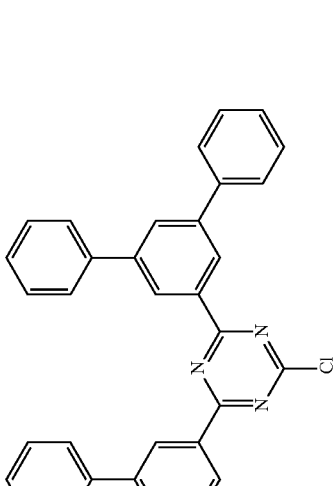 | 53 |

| Cmpd. | Reactant 5 or 7 | Reactant 8 | Product 9 | Yield [%] |
|---|---|---|---|---|
| 9i | dibenzothiophene-phenyl-chloropyrimidine | 9,9-dimethylfluorene-4-boronic acid [1246022-50-2] | product | 41 |
| 9j | dibenzofuran-phenylene-phenyl-chloropyrimidine | 9,9-dimethylfluorene-4-boronic acid [1246022-50-2] | product | 76 |

| Cmpd. | Reactant 5 or 7 | Reactant 8 | Product 9 | Yield [%] |
|---|---|---|---|---|
| 9k | | [1246022-50-2] | | 64 |
| 9l | | [1246022-50-2] | | 37 |

-continued

| Cmpd. | Reactant 5 or 7 | Reactant 8 | Product 9 | Yield [%] |
|---|---|---|---|---|
| 9m | (structure) | (structure) [1246022-50-2] | (structure) | 21 |
| 9n | (structure) | (structure) [1246022-50-2] | (structure) | 49 |

| Cmpd. | Reactant 5 or 7 | Reactant 8 | Product 9 | Yield [%] |
|---|---|---|---|---|
| 9p | 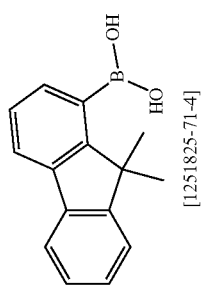 | 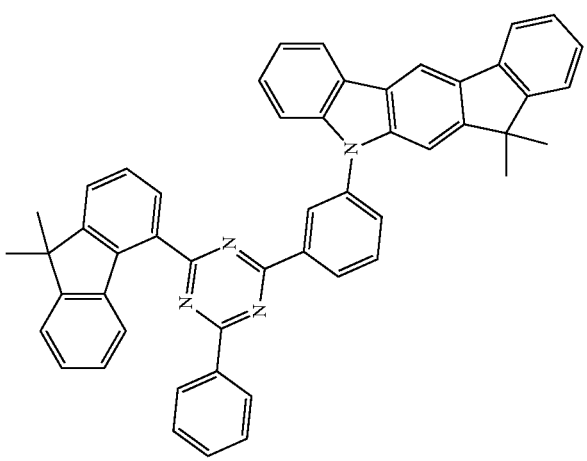 | 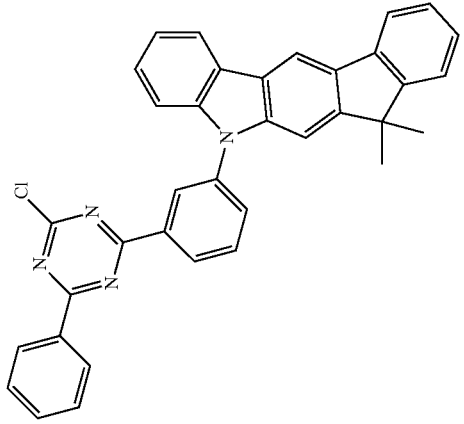 | 37 |
| 9q | 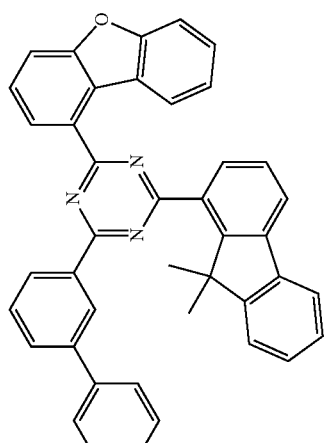 | 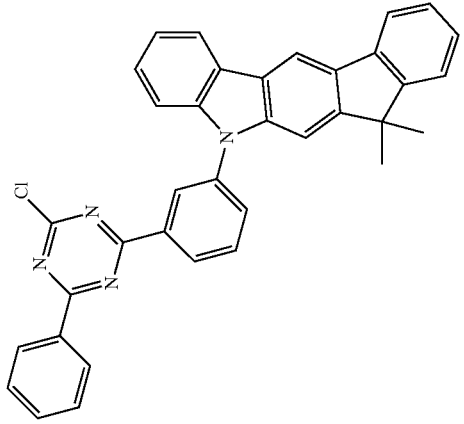 | 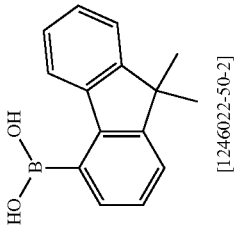 | 52 |

| Cmpd. | Reactant 5 or 7 | Reactant 8 | Product 9 | Yield [%] |
|---|---|---|---|---|
| 9r | | [124602-50-2] | | 56 |
| 9s | | [1251825-71-4] | | 48 |

-continued

| Cmpd. | Reactant 5 or 7 | Reactant 8 | Product 9 | Yield [%] |
|---|---|---|---|---|
| 9t | | [124602-50-2] | | 69 |
| 9x | | [1860896-40-7] | | 58 |

| Cmpd. | Reactant 5 or 7 | Reactant 8 | Product 9 | Yield [%] |
|---|---|---|---|---|
| 9z | 4-chloro-2-(3,5-diphenylphenyl)-6-phenyl-1,3,5-triazine | 4-(3-bromophenyl)-9,9-dimethylfluorene [1860896-40-7] | triazine product with fluorene, phenyl, and 3,5-diphenylphenyl substituents | 64 |
| 9u | 4-biphenyl-2-chloro-6-phenyl-1,3,5-triazine | 4-(3-bromophenyl)-9,9-dimethylfluorene [1860896-40-7] | triazine product with fluorene, phenyl, and biphenyl substituents | 68 |

-continued
| Cmpd. | Reactant 5 or 7 | Reactant 8 | Product 9 | Yield [%] |
|---|---|---|---|---|
| 9v | 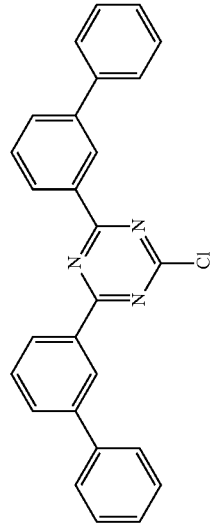 | 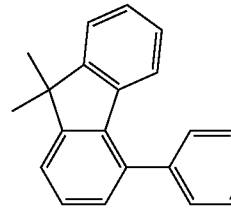 [1860896-38-3] | 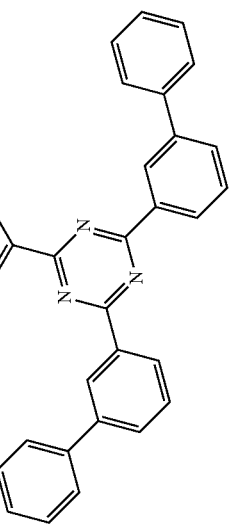 | 63 |
| 9w | 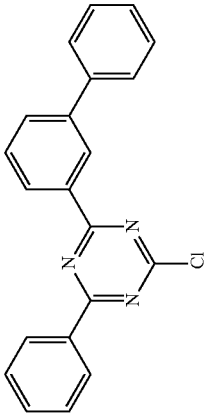 | [1860896-38-3] | | 59 |

| Cmpd. | Reactant 5 or 7 | Reactant 8 | Product 9 | Yield [%] |
|---|---|---|---|---|
| 9y | | [1867158-12-0] | | 58 |
| 9aa | | [1867158-12-0] | | 63 |

| Cmpd. | Reactant 5 or 7 | Reactant 8 | Product 9 | Yield [%] |
|---|---|---|---|---|
| 9ab | 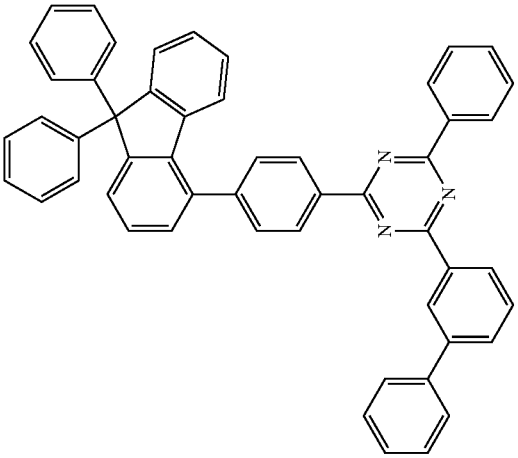 | 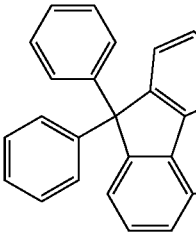 [1613372-04-5] | 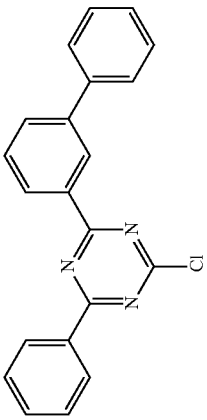 | 66 |

| Cmpd. | Reactant 5 or 7 | Reactant 8 | Product 9 | Yield [%] |
|---|---|---|---|---|
| 9ac | | [1613372-04-5] | | 57 |
| 9ad | | [713127-22-1] | | 60 |

The present invention furthermore relates to a process for the preparation of a compound of the formula (I), comprising the reaction steps of: synthesis of the skeleton of compound (I) which as yet contains no triazinyl or pyrimidinyl group; and reaction of the skeleton (preferably in the first step) in a C—C coupling, such as Suzuki, Negishi, Yamamoto, GrignardCross or Stille coupling, etc., or C—N coupling, such as Buchwald or Ullmann coupling.

Fabrication of OLEDs

The following examples V1-V7 and E1-E22 (see Table 1 and 2) show data from various OLEDs.

Substrate Pre-Treatment of Examples V1-V7 and E1-E22

Glass plates with structured ITO (50 nm, indium tin oxide) are coated with 20 nm PEDOT:PSS (Poly(3,4-ethylenedioxythiophene)poly(styrenesulfonate), CLEVIOS™ PVP AI 4083 from Heraeus Precious Metals GmbH Germany, spin-coated from a water-based solution) and form the substrates on which the OLEDs are processed.

The OLEDs have in principle the following layer structure: substrate/hole-transport layer (HTL)/optional interlayer (IL)/electron-blocking layer (EBL)/emission layer (EML)/optional hole-blocking layer (HBL)/electron-transport layer (ETL)/optional electron-injection layer (EIL) and finally a cathode. The cathode is formed by an aluminium layer with a thickness of 100 nm. The exact layer structure is denoted in Table 1. The materials used for the OLED fabrication are presented in Table 3.

All materials are applied by thermal vapour deposition in a vacuum chamber. The emission layer here always consists of at least one matrix material (host material) and an emitting dopant (emitter), which is admixed with the matrix material or matrix materials in a certain proportion by volume by co-evaporation. An expression such as IC1:M1:TEG1 (55%:35%:10%) here means that material IC1 is present in the layer in a proportion by volume of 55%, M1 is present in the layer in a proportion of 35% and TEG1 is present in the layer in a proportion of 10%. Analogously, the electron-transport layer may also consist of a mixture of two materials.

The OLEDs are characterised by standard methods. For this purpose, the electroluminescence spectra, the current efficiency (CE1000, measured in cd/A at 1000 cd/m$^2$), the luminous efficacy (LE1000, measured in lm/W at 1000 cd/m$^2$), the external quantum efficiency (EQE1000, measured in % at 1000 cd/m$^2$) and the voltage (U1000, measured at 1000 cd/m$^2$ in V) are determined from current/voltage/luminance characteristic lines (IUL characteristic lines) assuming a Lambertian emission profile. The electroluminescence (EL) spectra are recorded at a luminous density of 1000 cd/m$^2$ and the CIE 1931 x,y coordinates are then calculated from the EL spectrum.

For selected experiments, the lifetime is determined. The lifetime is defined as the time after which the luminous density has dropped to a certain proportion from a certain initial luminous density $L_1$ when the OLED is driven at a constant current. The starting condition $L_0;j_0=4000$ cd/m$^2$ and $L_1=70\%$ in Table 2 indicates that the in column LT denoted lifetime corresponds to the time in hours (h) needed to fade the OLED from a starting luminous density of 4000 cd/m$^2$ to 2800 cd/m$^2$. Accordingly, the lifetime of the starting condition $L_0;j_0=20$ mA/cm$^2$, $L_1=80\%$ is the time needed to fade the OLED operated at the constant current of 20 mA/cm$^2$ to 80% of the initial luminous density.

The device data of various OLEDs is summarized in Table 2. The examples V1-V7 are comparison examples according to the state-of-the-art. The examples E1-E22 show data of inventive OLEDs.

In the following section several examples are described in more detail to show the advantages of the inventive OLEDs. Use of Inventive Compounds as Electron Transport Layer and Host Material in Phosphorescent OLEDs The use of the inventive compounds as electron transport layer and as host material results in significantly improved OLED device data compared to state-of-the-art materials, especially with respect to device lifetime.

The use of the inventive materials (1) and (187) in an ETL mixed with LiQ results in improved LT compared to devices with the materials CE1 and CE2 (comparison of example V1 and V2 with E1 and E3, respectively). Furthermore, in comparison to material CE3 (which is a 3-(9,9-dimethylfluorenyl)triazine material), an inventive compound (186) which is identical to CE3 except it is a 4-(9,9-dimethylfluorenyl)triazine results in a significant improvement in LT efficacy when tested as a host in triplet green OLEDs (see V3 vs E2). It should also be noted that CE6 (sample V6), which is a 4-(9,9-dimethylfluorene)triazine with a 9,9'-spirobifluorene substituent on the triazine hardly gives any improvement compared to CE1 (sample V1) which is like CE6 but where a phenyl replaces the 4-(9,9-dimethylfluorene) group on the triazine.

TABLE 1

| OLED Layer Structure and Thickness | | | | | | | |
|---|---|---|---|---|---|---|---|
| Ex. | IL | HTL | EBL | EML | HBL | ETL | EIL |
| V1 | SpA1 140 nm | HATCN 5 nm | SpMA1 20 nm | M2:SEB (95%:5%) 20 nm | — | CE1:LiQ (50%:50%) 30 nm | — |
| V2 | SpA1 140 nm | HATCN 5 nm | SpMA1 20 nm | M2:SEB (95%:5%) 20 nm | — | CE2:LiQ (50%:50%) 30 nm | — |
| V3 | SpA1 70 nm | HATCN 5 nm | SpMA1 90 nm | IC1:TEG1 (90%:10%) 30 nm | IC1 10 nm | CE3:LiQ (50%:50%) 30 nm | — |
| V4 | SpA1 140 nm | HATCN 5 nm | SpMA1 20 nm | M2:SEB (95%:5%) 20 nm | — | CE4:LiQ (50%:50%) 30 nm | — |
| V5 | SpA1 70 nm | HATCN 5 nm | SpMA1 90 nm | CE5:TEG1 (90%:10%) 30 nm | | ST2:LiQ (50%:50%) 40 nm | — |

TABLE 1-continued

| | OLED Layer Structure and Thickness | | | | | | |
|---|---|---|---|---|---|---|---|
| Ex. | IL | HTL | EBL | EML | HBL | ETL | EIL |
| V6 | SpA1 140 nm | HATCN 5 nm | SpMA1 20 nm | M2:SEB (95%:5%) 20 nm | — | CE6:LiQ (50%:50%) 30 nm | — |
| V7 | SpA1 70 nm | HATCN 5 nm | SpMA1 90 nm | (CE7):TEG1 (90%:10%) 30 nm | — | ST2:LiQ (50%:50%) 40 nm | — |
| E1 | SpA1 140 nm | HATCN 5 nm | SpMA1 20 nm | M2:SEB (95%:5%) 20 nm | — | (1):LiQ (50%:50%) 30 nm | — |
| E2 | SpA1 70 nm | HATCN 5 nm | SpMA1 90 nm | IC1:TEG1 (90%:10%) 30 nm | IC1 10 nm | (186):LiQ (50%:50%) 30 nm | — |
| E3 | SpA1 140 nm | HATCN 5 nm | SpMA1 20 nm | M2:SEB (95%:5%) 20 nm | — | (187):LiQ (50%:50%) 30 nm | — |
| E4 | SpA1 70 nm | HATCN 5 nm | SpMA1 90 nm | (188):TEG1 (90%:10%) 30 nm | ST2 10 nm | ST2:LiQ (50%:50%) 30 nm | — |
| E5 | SpA1 70 nm | HATCN 5 nm | SpMA1 90 nm | (38):TEG1 (90%:10%) 30 nm | ST2 10 nm | ST2:LiQ (50%:50%) 30 nm | — |
| E6 | SpA1 70 nm | HATCN 5 nm | SpMA1 90 nm | (45):TEG1 (90%:10%) 30 nm | ST2 10 nm | ST2:LiQ (50%:50%) 30 nm | — |
| E7 | SpA1 70 nm | HATCN 5 nm | SpMA1 90 nm | (88):TEG1 (90%:10%) 30 nm | ST2 10 nm | ST2:LiQ (50%:50%) 30 nm | — |
| E8 | SpA1 70 nm | HATCN 5 nm | SpMA1 90 nm | IC1:TEG1 (90%:10%) 30 nm | — | (41):LiQ (50%:50%) 40 nm | — |
| E9 | SpA1 70 nm | HATCN 5 nm | SpMA1 90 nm | IC1:TEG1 (90%:10%) 30 nm | IC1 10 nm | (189):LiQ (50%:50%) 30 nm | — |
| E10 | SpA1 140 nm | HATCN 5 nm | SpMA1 20 nm | M2:SEB (95%:5%) 20 nm | — | (1):LiQ (50%:50%) 30 nm | — |
| E11 | SpA1 70 nm | HATCN 5 nm | SpMA1 90 nm | (88):TEG1 (90%:10%) 30 nm | ST2 10 nm | ST2:LiQ (50%:50%) 30 nm | — |
| E12 | SpA1 70 nm | HATCN 5 nm | SpMA1 90 nm | IC1:TEG1 (90%:10%) 30 nm | (33) 10 nm | ST2:LiQ (50%:50%) 30 nm | — |
| E13 | SpA1 140 nm | HATCN 5 nm | SpMA1 20 nm | M2:SEB (95%:5%) 20 nm | — | 9x:LiQ (45%:55%) 30 nm | — |
| E14 | SpA1 140 nm | HATCN 5 nm | SpMA1 20 nm | M2:SEB (95%:5%) 20 nm | — | 9z:LiQ (45%:55%) 30 nm | — |
| E15 | SpA1 140 nm | HATCN 5 nm | SpMA1 20 nm | M2:SEB (95%:5%) 20 nm | 9u 5 nm | 9u:LiQ (45%:55%) 25 nm | — |
| E16 | SpA1 140 nm | HATCN 5 nm | SpMA1 20 nm | M2:SEB (95%:5%) 20 nm | — | 9v:LiQ (45%:55%) 30 nm | — |
| E17 | SpA1 140 nm | HATCN 5 nm | SpMA1 20 nm | M2:SEB (95%:5%) 20 nm | — | 9w:LiQ (45%:55%) 30 nm | — |

TABLE 1-continued

OLED Layer Structure and Thickness

| Ex. | IL | HTL | EBL | EML | HBL | ETL | EIL |
|---|---|---|---|---|---|---|---|
| E18 | SpA1 70 nm | HATCN 5 nm | SpMA1 90 nm | IC1:IC3:TEG1 (65%:30%:5%) 30 nm | 9y 10 nm | 9y:LiQ (50%:50%) 30 nm | — |
| E19 | SpA1 70 nm | HATCN 5 nm | SpMA1 90 nm | IC1:IC3:TEG1 (65%:30%:5%) 30 nm | — | 9aa:LiQ (50%:50%) 40 nm | — |
| E20 | SpA1 70 nm | HATCN 5 nm | SpMA1 90 nm | IC1:IC3:TEG1 (65%:30%:5%) 30 nm | 9ab 10 nm | 9ab:LiQ (50%:50%) 30 nm | — |
| E21 | SpA1 70 nm | HATCN 5 nm | SpMA1 90 nm | IC1:IC3:TEG1 (65%:30%:5%) 30 nm | — | 9ac:LiQ (50%:50%) 40 nm | — |
| E22 | SpA1 70 nm | HATCN 5 nm | SpMA1 90 nm | IC1:IC3:TEG1 (65%:30%:5%) 30 nm | — | 9ad:LiQ (50%:50%) 40 nm | — |

TABLE 2

OLED Device Data

| Ex. | U1000 (V) | CE1000 (cd/A) | LE1000 (lm/W) | EQE 1000 | CIE x/y at 1000 cd/m$^2$ | $L_0$; $j_0$ | $L_1$ % | LT (h) |
|---|---|---|---|---|---|---|---|---|
| V1 | 4.5 | 8 | 6 | 7.1% | 0.14/0.14 | 6000 cd/m$^2$ | 80 | 35 |
| V2 | 4.8 | 8 | 5 | 7.2% | 0.13/0.14 | 6000 cd/m$^2$ | 80 | 32 |
| V3 | 3.4 | 62 | 57 | 17.3% | 0.31/0.64 | 20 mA/m$^2$ | 80 | 115 |
| V4 | 4.9 | 7 | 4 | 6.8% | 0.14/0.13 | 6000 cd/m$^2$ | 80 | 47 |
| V5 | 3.2 | 57 | 56 | 15.4% | 0.34/0.63 | 20 mA/m$^2$ | 80 | 195 |
| V6 | 4.8 | 8 | 5 | 7.0% | 0.14/0.13 | 6000 cd/m$^2$ | 80 | 45 |
| V7 | 3.4 | 54 | 50 | 15.0% | 0.31/0.64 | 20 mA/m$^2$ | 80 | 240 |
| E1 | 5.0 | 8 | 5 | 6.9% | 0.13/0.14 | 6000 cd/m$^2$ | 80 | 42 |
| E2 | 3.6 | 64 | 56 | 17.1% | 0.31/0.64 | 20 mA/m$^2$ | 80 | 140 |
| E3 | 4.5 | 8 | 6 | 7.3% | 0.14/0.13 | 6000 cd/m$^2$ | 80 | 48 |
| E4 | 4.3 | 56 | 41 | 15.8% | 0.32/0.63 | 20 mA/m$^2$ | 80 | 50 |
| E5 | 4.0 | 53 | 42 | 14.0% | 0.33/0.63 | 20 mA/m$^2$ | 80 | 40 |
| E6 | 4.1 | 57 | 44 | 15.2% | 0.33/0.63 | 20 mA/m$^2$ | 80 | 55 |
| E7 | 3.8 | 63 | 52 | 16.9% | 0.31/0.65 | 20 mA/m$^2$ | 80 | 85 |
| E8 | 3.4 | 64 | 59 | 17.2% | 0.34/0.62 | 20 mA/m$^2$ | 80 | 125 |
| E9 | 3.6 | 64 | 56 | 17.4% | 0.32/0.64 | 20 mA/m$^2$ | 80 | 120 |
| E10 | 4.8 | 8 | 5 | 7.4% | 0.14/0.14 | 6000 cd/m$^2$ | 80 | 40 |
| E11 | 3.9 | 62 | 50 | 16.8% | 0.33/0.63 | 20 mA/m$^2$ | 80 | 90 |
| E12 | 3.4 | 65 | 60 | 17.3% | 0.35/0.62 | 20 mA/m$^2$ | 80 | 110 |
| E13 | 4.8 | 8.1 | 5.3 | 7.2% | 0.14/0.13 | 6000 cd/m$^2$ | 80 | 35 |
| E14 | 5.0 | 8.0 | 5.0 | 7.1% | 0.14/0.13 | 6000 cd/m$^2$ | 80 | 43 |
| E15 | 4.8 | 8.4 | 5.5 | 7.1% | 0.14/0.15 | 6000 cd/m$^2$ | 80 | 41 |
| E16 | 5.1 | 7.6 | 4.7 | 6.7% | 0.14/0.14 | 6000 cd/m$^2$ | 80 | 48 |
| E17 | 5.0 | 7.5 | 4.7 | 6.8% | 0.14/0.13 | 6000 cd/m$^2$ | 80 | 46 |
| E18 | 3.4 | 63 | 58 | 16.9% | 0.34/0.62 | 20 mA/m$^2$ | 80 | 205 |
| E19 | 3.5 | 60 | 54 | 16.7% | 0.32/0.63 | 20 mA/m$^2$ | 80 | 200 |
| E20 | 3.5 | 59 | 53 | 16.6% | 0.32/0.63 | 20 mA/m$^2$ | 80 | 220 |
| E21 | 3.3 | 60 | 57 | 16.4% | 0.33/0.63 | 20 mA/m$^2$ | 80 | 215 |
| E22 | 3.6 | 62 | 54 | 17.1% | 0.32/0.63 | 20 mA/m$^2$ | 80 | 170 |

TABLE 3
Chemical structures of the OLED materials used in examples
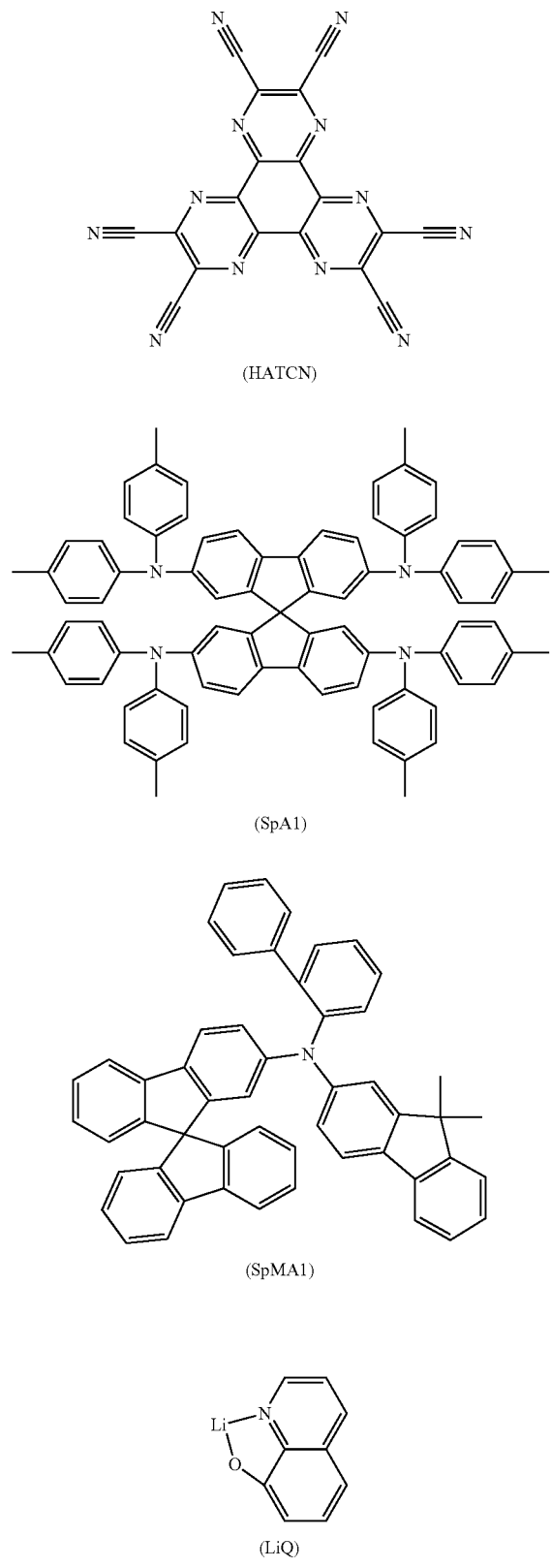
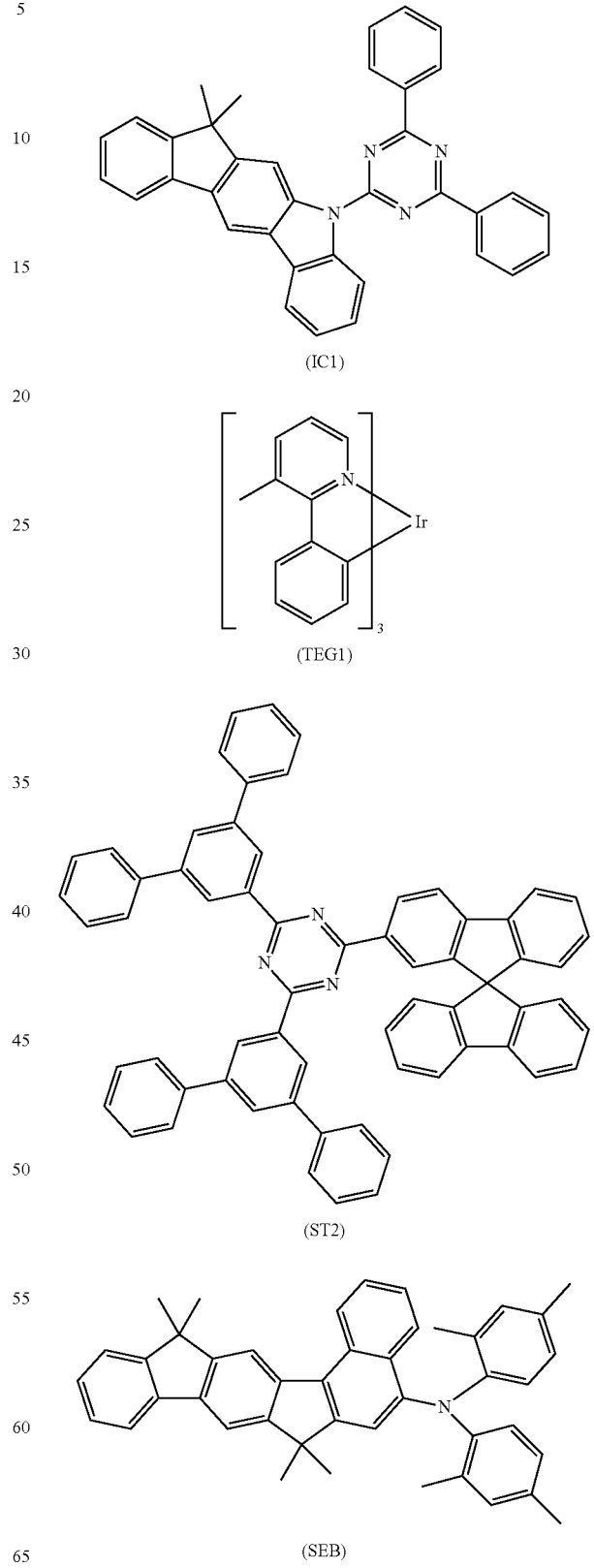

TABLE 3-continued
Chemical structures of the OLED materials used in examples
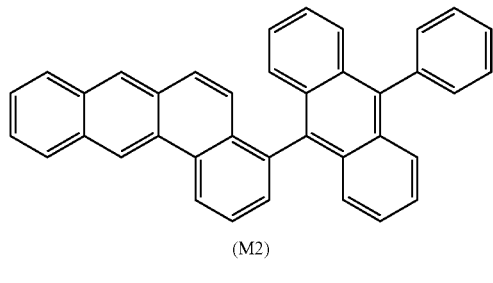
(M2)
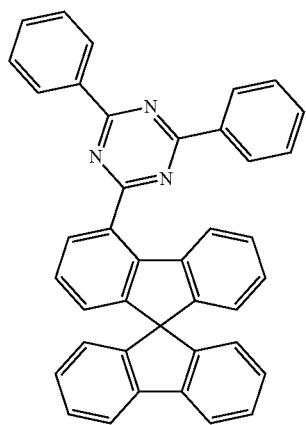
(CE1)
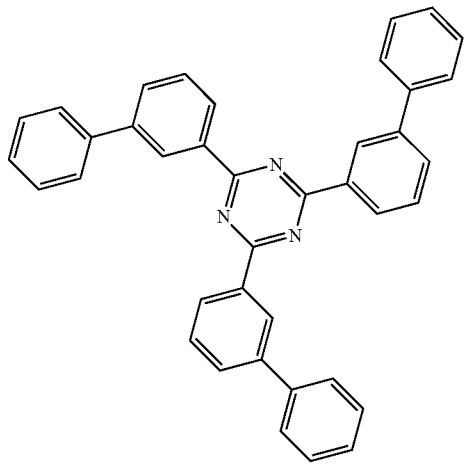
(CE2)
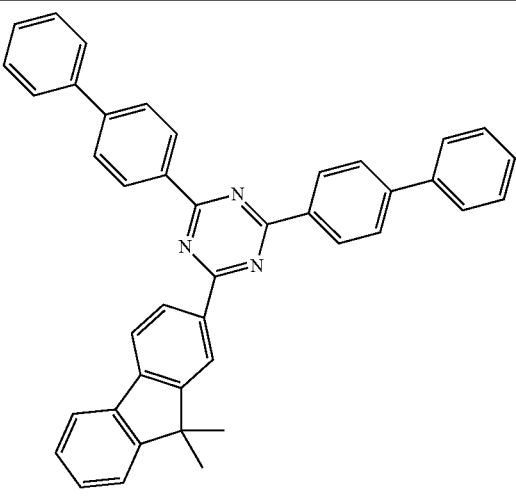
(CE3)
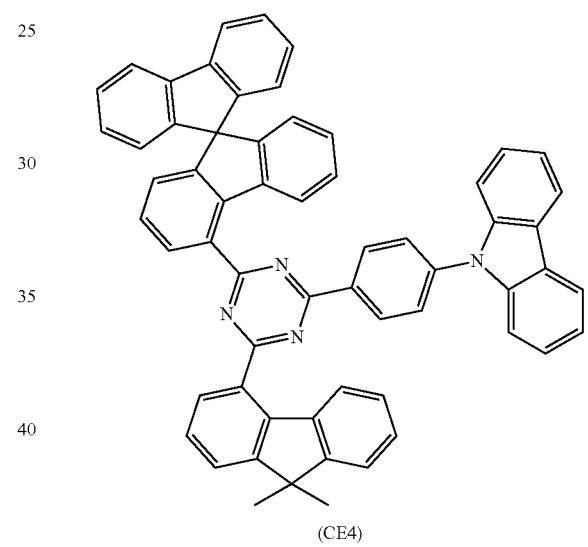
(CE4)
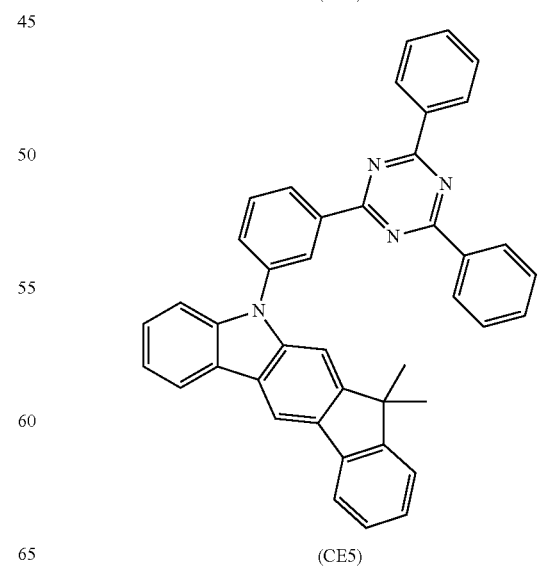
(CE5)

TABLE 3-continued
Chemical structures of the OLED materials used in examples
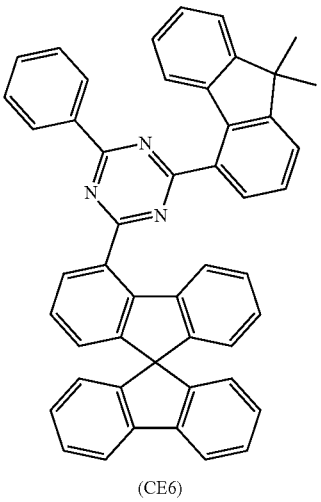
(CE6)
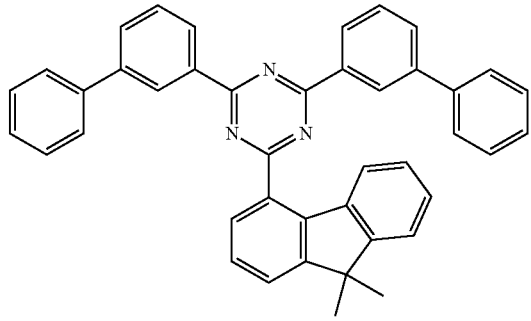 [SMILES: CC1(C)c2ccccc2-c2c(-c3nc(-c4cccc(-c5ccccc5)c4)nc(-c4cccc(-c5ccccc5)c4)n3)cccc21]
(1)
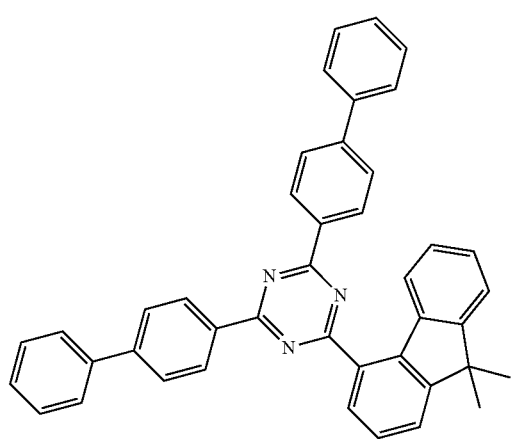
(186)
TABLE 3-continued
Chemical structures of the OLED materials used in examples
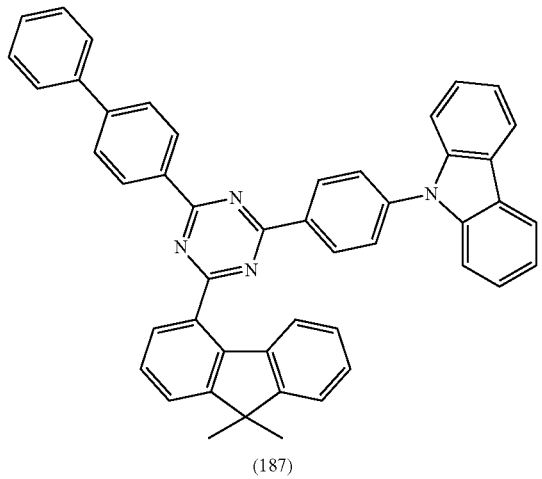
(187)
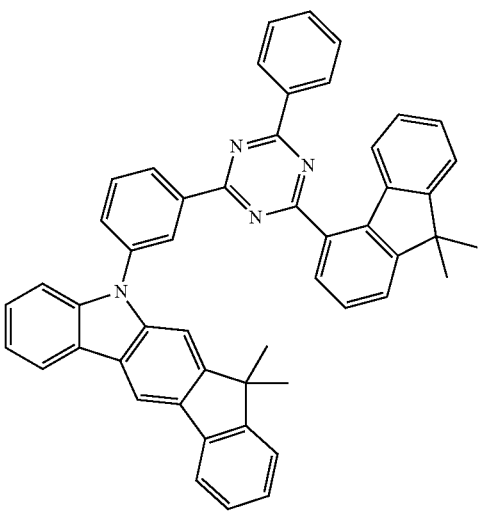
(CE7)
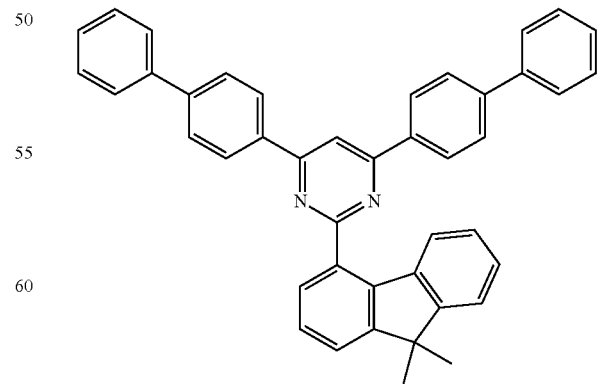
(188)

TABLE 3-continued
Chemical structures of the OLED materials used in examples
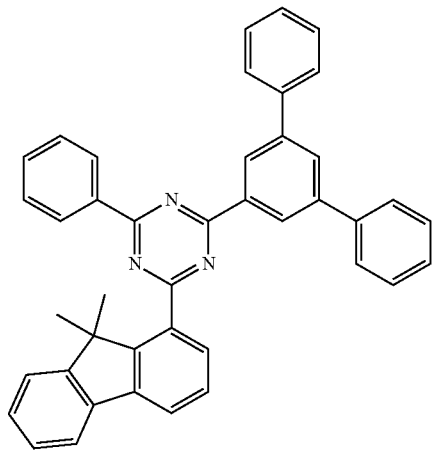 [SMILES: CC1(C)c2ccccc2-c2cccc(-c3nc(-c4ccccc4)nc(-c4cc(-c5ccccc5)cc(-c5ccccc5)c4)n3)c21]
(38)
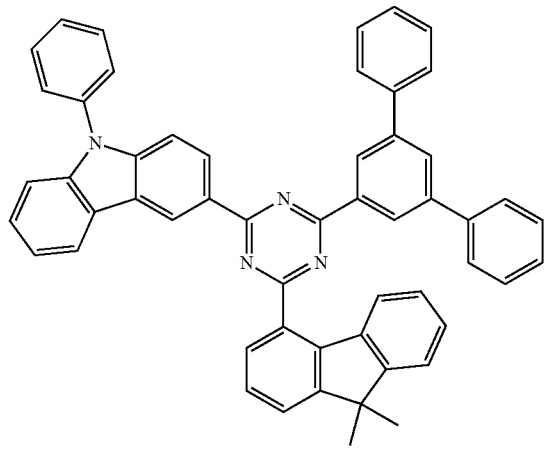 [SMILES: CC1(C)c2ccccc2-c2c(-c3nc(-c4cc(-c5ccccc5)cc(-c5ccccc5)c4)nc(-c4ccc5c(c4)c4ccccc4n5-c4ccccc4)n3)cccc21]
(45)
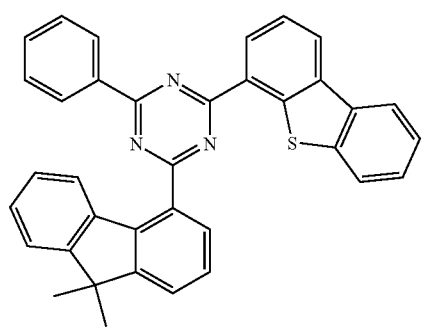 [SMILES: CC1(C)c2ccccc2-c2c(-c3nc(-c4ccccc4)nc(-c4cccc5c4sc4ccccc45)n3)cccc21]
(88)
TABLE 3-continued
Chemical structures of the OLED materials used in examples
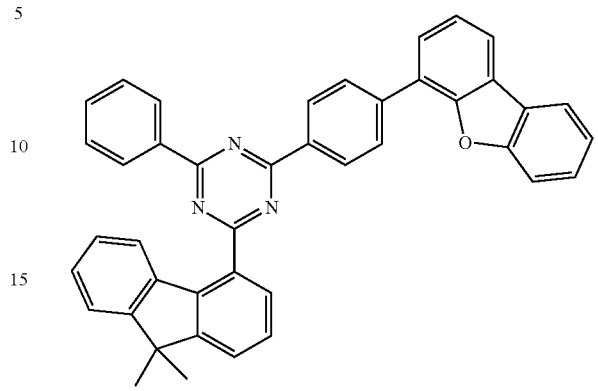
(41)
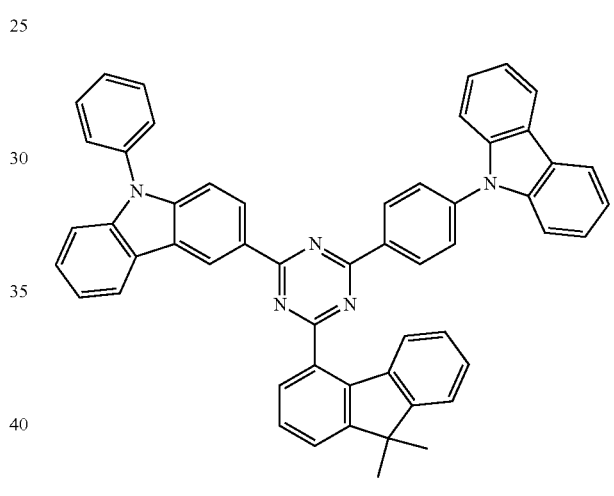
(189)
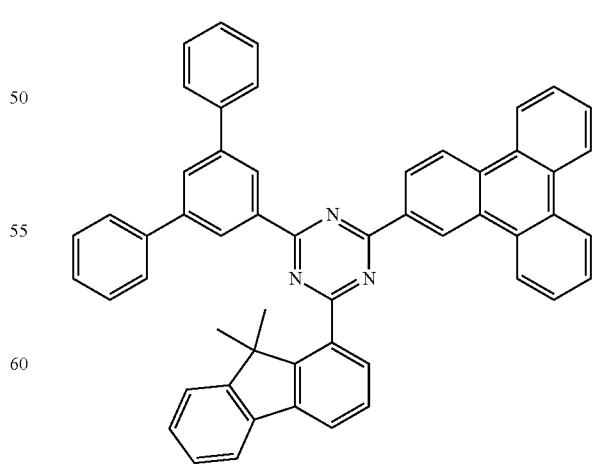
(33)

TABLE 3-continued
Chemical structures of the OLED materials used in examples
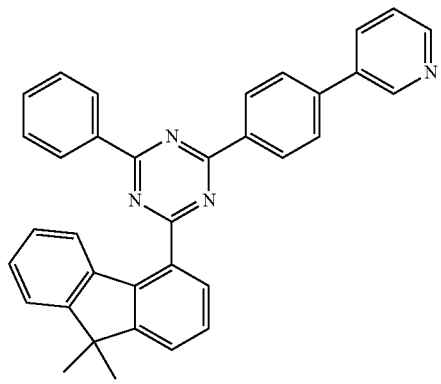 [SMILES: CC1(C)c2ccccc2-c2c(-c3nc(-c4ccccc4)nc(-c4ccc(-c5cccnc5)cc4)n3)cccc21]
(190)
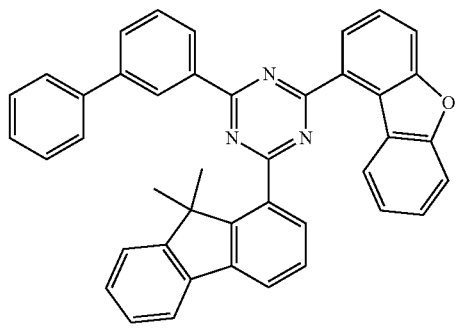 [SMILES: CC1(C)c2ccccc2-c2cccc(-c3nc(-c4cccc(-c5ccccc5)c4)nc(-c4cccc5oc6ccccc6c45)n3)c21]
(87)
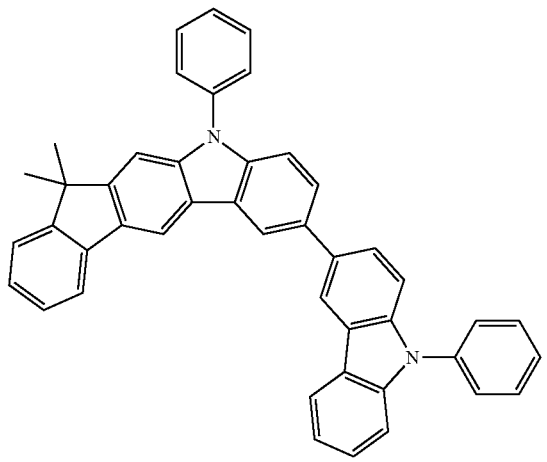
(IC3)
TABLE 3-continued
Chemical structures of the OLED materials used in examples
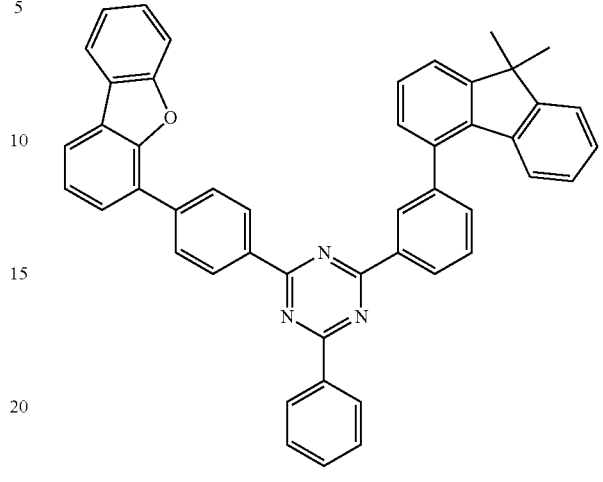
(9x)
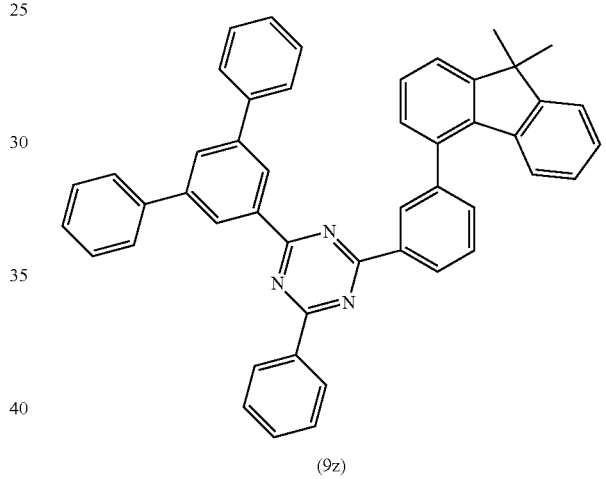
(9z)
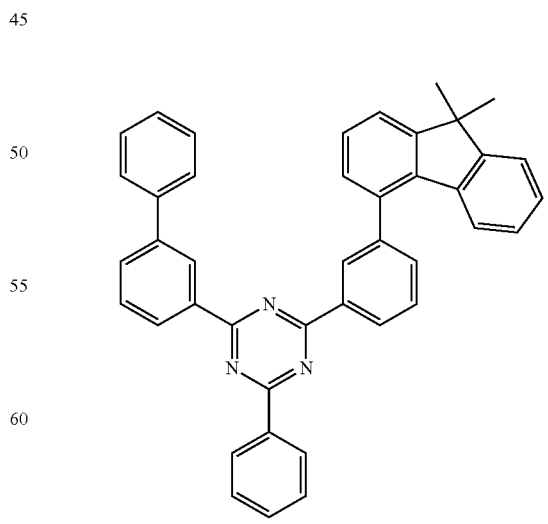
(9u)

TABLE 3-continued
Chemical structures of the OLED materials used in examples
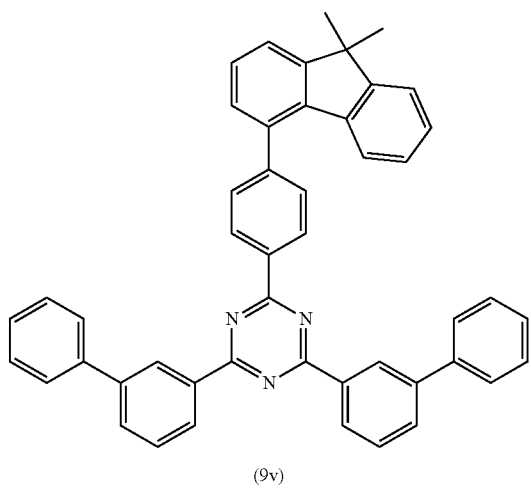
(9v)
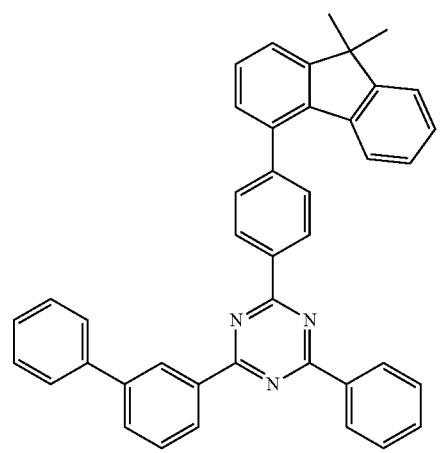 [SMILES: CC1(C)c2ccccc2-c2c(-c3ccc(-c4nc(-c5ccccc5)nc(-c5cccc(-c6ccccc6)c5)n4)cc3)cccc21]
(9w)
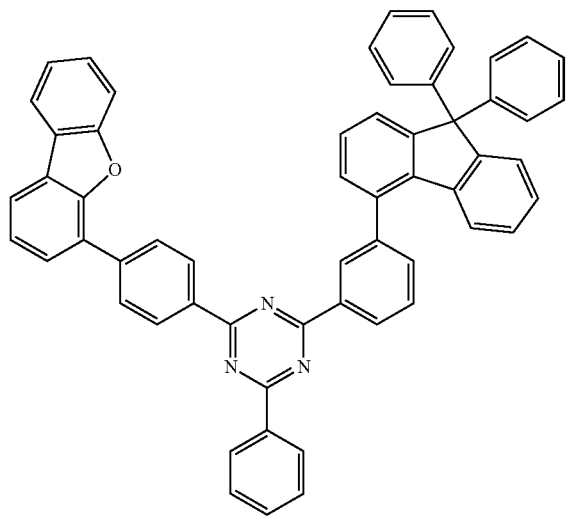 [SMILES: c1ccc(-c2nc(-c3ccc(-c4cccc5c4oc4ccccc45)cc3)nc(-c3cccc(-c4cccc5c4-c4ccccc4C5(c4ccccc4)c4ccccc4)c3)n2)cc1]
(9y)
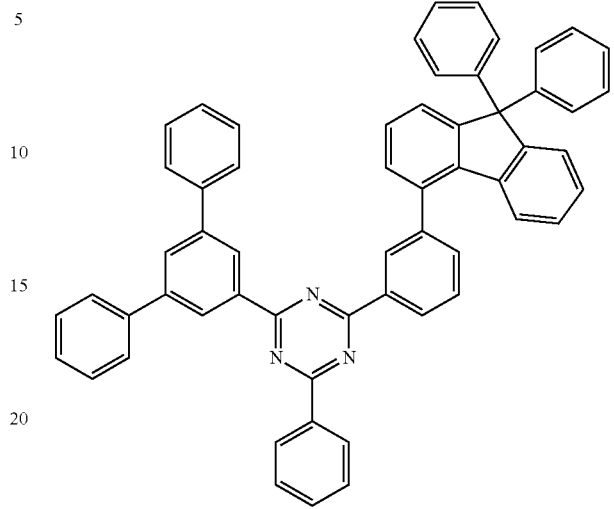
(9aa)
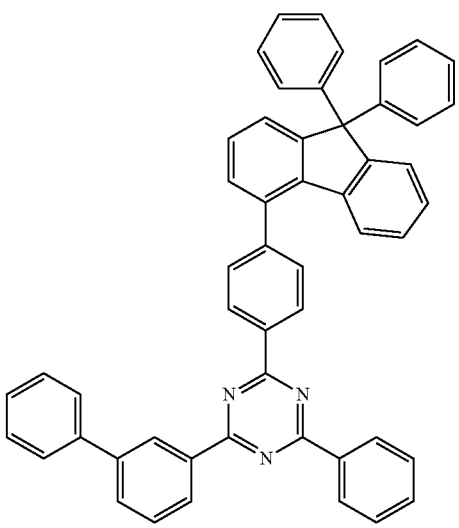 [SMILES: c1ccc(-c2cccc(-c3nc(-c4ccccc4)nc(-c4ccc(-c5cccc6c5-c5ccccc5C6(c5ccccc5)c5ccccc5)cc4)n3)c2)cc1]
(9ab)

TABLE 3-continued

Chemical structures of the OLED materials used in examples

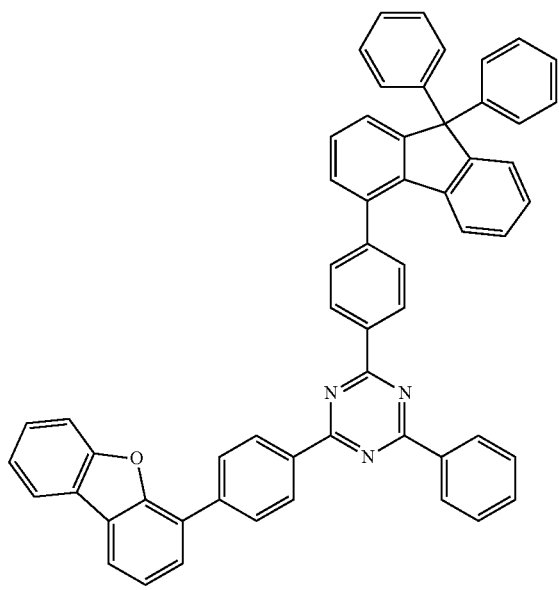 [SMILES: c1ccc(-c2nc(-c3ccc(-c4cccc5c4-c4ccccc4C5(c4ccccc4)c4ccccc4)cc3)nc(-c3ccc(-c4cccc5c4oc4ccccc45)cc3)n2)cc1]

(9ac)

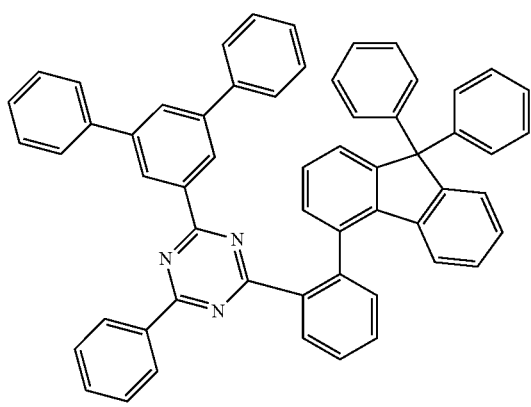

(9ad)

The invention claimed is:

1. A compound of formula (IV) or (V):

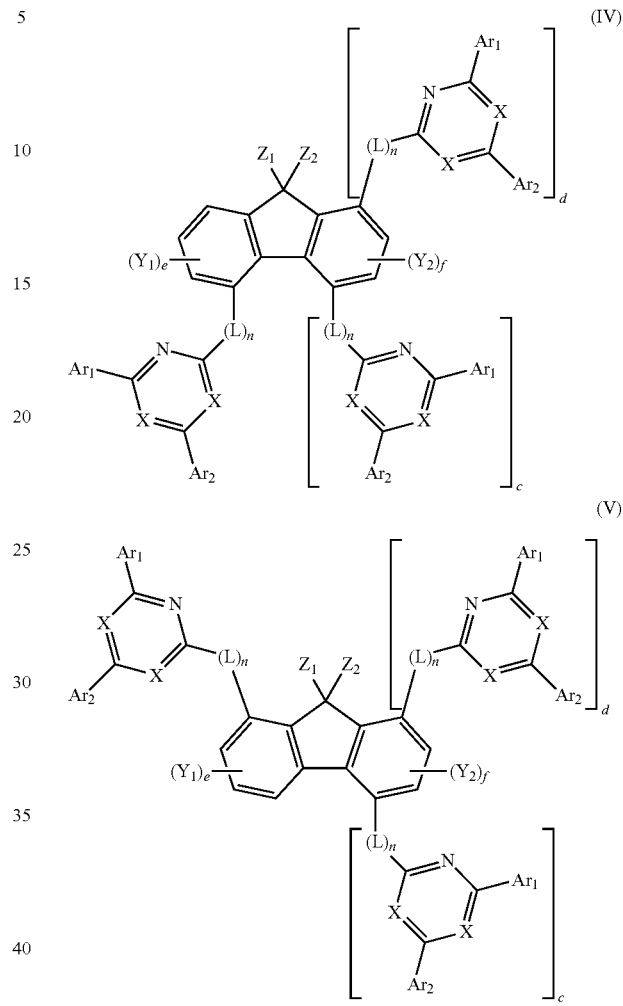

wherein:

$Z_1$ and $Z_2$ are on each occurrence, identically or differently, H, D, F, Cl, Br, I, CHO, $N(Ar_1)_2$, $C(=O)Ar_1$, $P(=O)(Ar_1)_2$, $S(=O)Ar_1$, $S(=O)_2Ar_1$, $CR_2=CR_2Ar_1$, CN, $NO_2$, $Si(R_1)_3$, $B(OR_1)_2$, $B(R_1)_2$, $B(N(R_1)_2)_2$, $OSO_2R_1$, a straight-chain alkyl, alkoxy, or thio-alkoxy group having 1 to 40 C atoms, a straight-chain alkenyl or alkynyl group having 2 to 40 C atoms, or a branched or cyclic alkyl, alkenyl, alkynyl, alkoxy, or thioalkoxy group having 3 to 40 C atoms, each of which is optionally substituted by one or more radicals $R_1$, wherein one or more $CH_2$ groups are optionally replaced by $(R_1)C=C(R_1)$, $C≡C$, $Si(R_1)_2$, $Ge(R_1)_2$, $Sn(R_1)_2$, $C=O$, $C=S$, $C=Se$, $C=N(R_1)$, $P(=O)(R_1)$, SO, $SO_2$, $N(R_1)_2$, O, S, or $CON(R_1)_2$, and wherein one or more H atoms are optionally replaced by D, F, Cl, Br, I, CN, or $NO_2$, an aromatic or heteroaromatic ring system having 5 to 60 aromatic ring atoms, which in each case is optionally substituted by one or more radicals $R_1$, or an aryloxy or heteroaryloxy group having 5 to 60 aromatic ring atoms, which is optionally substituted by one or more radicals $R_1$, and wherein $Z_1$ and $Z_2$ do not form a bis-spirobifluorene;

$Y_1$ and $Y_2$
are on each occurrence, identically or differently, D, F, Cl, Br, I, CHO, $N(Ar_1)_2$, $C(=O)Ar_1$, $P(=O)(Ar_1)_2$, $S(=O)Ar_1$, $S(=O)_2Ar_1$, $(R_1)C=C(R_1)Ar_1$, CN, $NO_2$, $Si(R_1)_3$, $B(OR_1)_2$, $B(R_1)_2$, $B(N(R_1)_2)_2$, $OSO_2R_1$, a straight-chain alkyl, alkoxy, or thioalkoxy group having 1 to 40 C atoms, a straight-chain alkenyl or alkynyl group having 2 to 40 C atoms, or a branched or cyclic alkyl, alkenyl, alkynyl, alkoxy, or thioalkoxy group having 3 to 40 C atoms, each of which is optionally substituted by one or more radicals $R_1$, wherein one or more $CH_2$ groups are optionally replaced by $(R_1)C=C(R_1)$, $C\equiv C$, $Si(R_1)_2$, $Ge(R_1)_2$, $Sn(R_1)_2$, $C=O$, $C=S$, $C=Se$, $C=N(R_1)_2$, $P(=O(R_1)_2$, SO, $SO_2$, $N(R_1)_2$, O, S, or $CON(R_1)_2$ and wherein one or more H atoms are optionally replaced by D, F, Cl, Br, I, CN, or $NO_2$, an aromatic or heteroaromatic ring system having 5 to 60 aromatic ring atoms, which in each case is optionally substituted by one or more radicals $R_1$, or an aryloxy or heteroaryloxy group having 5 to 60 aromatic ring atoms, which is optionally substituted by one or more radicals $R_1$, or a combination of these systems; and wherein two or more adjacent substituents $Y_1$ or $Y_2$ optionally define an annulated mono- or polycyclic, aliphatic or aromatic or heteroaromatic ring system with one another;

$Ar_1$ and $Ar_2$
are on each occurrence, identically or differently, an aromatic or heteroaromatic ring system having 5 to 23 aromatic ring atoms, which in each case is optionally substituted by one or more radicals $R_1$, with the proviso that a heteroaromatic ring system is connected via a carbon-carbon bond;

$R_1$ is on each occurrence, identically or differently, H, D, F, Cl, Br, I, CN, $Si(R_2)_3$, a straight-chain alkyl, alkoxy, or thioalkyl group having 1 to 40 C atoms or a branched or cyclic alkyl, alkoxy, or thioalkyl with 3-40 C-atoms which is optionally substituted by one or more radicals $R_2$, wherein each one or more non-adjacent $CH_2$ groups are optionally replaced by $C(R_2)=C(R_2)$, $Si(R_2)_2$, $C=NR_2$, $P(=O)(R_2)$, SO, $SO_2$, $NR_2$, O, S, or $CONR_2$ and wherein one or more H atoms are optionally replaced by D, F, Cl, Br, or I, an aromatic or heteroaromatic ring system having 6 to 40 carbon atoms which are optionally substituted by one or more radicals $R_2$, an aryloxy group having 5 to 60 aromatic ring atoms which are optionally substituted by one or more radicals $R_2$, or an aralkyl group having 5 to 60 aromatic ring atoms which are optionally substituted by one or more radicals $R_2$, wherein two or more adjacent substituents $R_1$ optionally define a mono- or polycyclic, aliphatic, aromatic, or heteroaromatic ring system with one another, which is optionally substituted with one or more radicals $R_2$; wherein $R_2$ is selected from the group consisting of H, D, F, an aliphatic hydrocarbon radical having 1 to 20 carbon atoms, or an aromatic or heteroaromatic ring system having 5 to 30 C atoms, wherein two or more adjacent substituents $R_2$ optionally define a mono- or polycyclic, aliphatic, aromatic, or heteroaromatic ring system with one another;

X is on each occurrence, identically or differently, $CR_1$ or N, with the proviso that at least one X is N;

L is on each occurrence, identically or differently, an aromatic or heteroaromatic ring system having 5-30 aromatic ring atoms, which is optionally substituted by one or more non-aromatic radicals $R_1$;

c and d
are each, identically or differently, 0 or 1 with the proviso one of c or d is 1;

e and f
are each, identically or differently, 0, 1, 2, or 3; and n is on each occurrence, identically or differently, 0 or 1.

2. The compound of claim 1, where $Z_1$ and $Z_2$ are identical and are not connected to each other at any point other than at the 9-position of the fluorene nucleus.

3. The compound of claim 1, wherein e or f are both 0 according to formula (III):

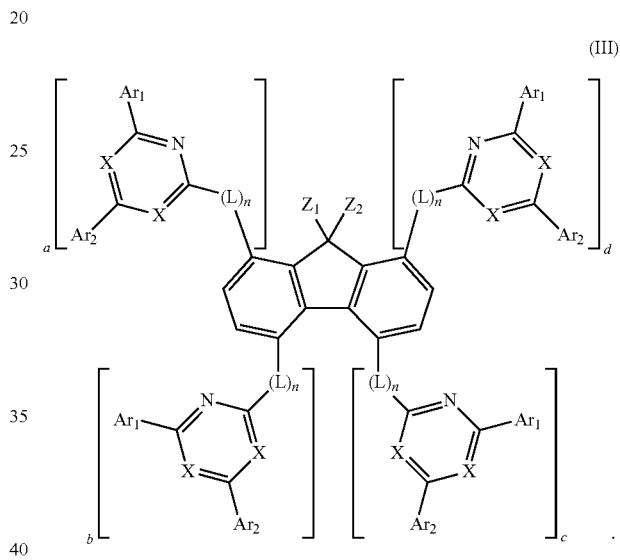

4. The compound of claim 1, wherein e and f are both 0.

5. The compound according to claim 1, wherein the compound is a compound of formula (VI) or (VII)

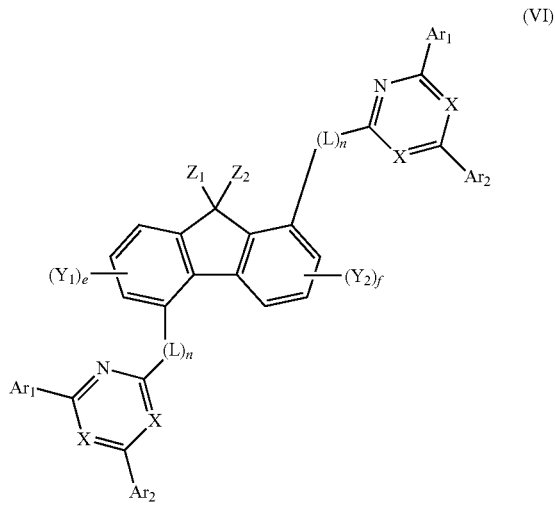

-continued

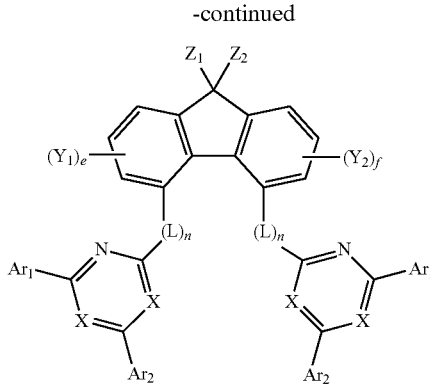

(VII)

6. A compound of formula (I):

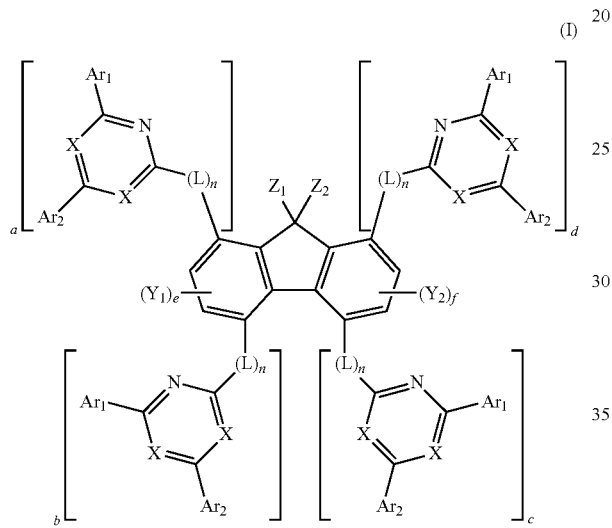

(I)

wherein:

$Z_1$ and $Z_2$ are on each occurrence, identically or differently, H, D, F, Cl, Br, I, CHO, N(Ar$_1$)$_2$, C(=O)Ar$_1$, P(=O)(Ar$_1$)$_2$, S(=O)Ar$_1$, S(=O)$_2$Ar$_1$, CR$_2$=CR$_2$Ar$_1$, CN, NO$_2$, Si(R$_1$)$_3$, B(OR$_1$)$_2$, B(R$_1$)$_2$, B(N(R$_1$)$_2$)$_2$, OSO$_2$R$_1$, a straight-chain alkyl, alkoxy, or thioalkoxy group having 1 to 40 C atoms, a straight-chain alkenyl or alkynyl group having 2 to 40 C atoms, or a branched or cyclic alkyl, alkenyl, alkynyl, alkoxy, or thioalkoxy group having 3 to 40 C atoms, each of which is optionally substituted by one or more radicals R$_1$, wherein one or more CH$_2$ groups are optionally replaced by (R$_1$)C=C(R$_1$), C≡C, Si(R$_1$)$_2$, Ge(R$_1$)$_2$, Sn(R$_1$)$_2$, C=O, C=S, C=Se, C=N(R$_1$), P(=O)(R$_1$), SO, SO$_2$, N(R$_1$)$_2$, O, S, or CON(R$_1$)$_2$, and wherein one or more H atoms are optionally replaced by D, F, Cl, Br, I, CN, or NO$_2$, an aromatic or heteroaromatic ring system having 5 to 60 aromatic ring atoms, which in each case is optionally substituted by one or more radicals R$_1$, or an aryloxy or heteroaryloxy group having 5 to 60 aromatic ring atoms, which is optionally substituted by one or more radicals R$_1$, and wherein $Z_1$ and $Z_2$ do not form a bis-spirobifluorene;

$Y_1$ and $Y_2$ are on each occurrence, identically or differently, D, F, Cl, Br, I, CHO, N(Ar$_1$)$_2$, C(=O)Ar$_1$, P(=O)(Ar$_1$)$_2$, S(=O)Ar$_1$, S(=O)$_2$Ar$_1$, (R$_1$)C=C(R$_1$)Ar$_1$, CN, NO$_2$, Si(R$_1$)$_3$, B(OR$_1$)$_2$, B(R$_1$)$_2$, B(N(R$_1$)$_2$)$_2$, OSO$_2$R$_1$, a straight-chain alkyl, alkoxy, or thioalkoxy group having 1 to 40 C atoms, a straight-chain alkenyl or alkynyl group having 2 to 40 C atoms, or a branched or cyclic alkyl, alkenyl, alkynyl, alkoxy, or thioalkoxy group having 3 to 40 C atoms, each of which is optionally substituted by one or more radicals R$_1$, wherein one or more CH$_2$ groups are optionally replaced by (R$_1$)C=C(R$_1$), C≡C, Si(R$_1$)$_2$, Ge(R$_1$)$_2$, Sn(R$_1$)$_2$, C=O, C=S, C=Se, C=N(R$_1$)$_2$, P(=O)(R$_1$)$_2$, SO, SO$_2$, N(R$_1$)$_2$, O, S, or CON(R$_1$)$_2$ and wherein one or more H atoms are optionally replaced by D, F, Cl, Br, I, CN, or NO$_2$, an aromatic or heteroaromatic ring system having 5 to 60 aromatic ring atoms, which in each case is optionally substituted by one or more radicals R$_1$, or an aryloxy or heteroaryloxy group having 5 to 60 aromatic ring atoms, which is optionally substituted by one or more radicals R$_1$, or a combination of these systems; and wherein two or more adjacent substituents $Y_1$ or $Y_2$ optionally define an annulated mono- or polycyclic, aliphatic or aromatic or heteroaromatic ring system with one another;

Ar$_1$ and Ar$_2$ are on each occurrence, identically or differently, an aromatic or heteroaromatic ring system having 5 to 23 aromatic ring atoms, which in each case is optionally substituted by one or more radicals R$_1$, with the proviso that a heteroaromatic ring system is connected via a carbon-carbon bond;

R$_1$ is on each occurrence, identically or differently, H, D, F, Cl, Br, I, CN, Si(R$_2$)$_3$, a straight-chain alkyl, alkoxy, or thioalkyl group having 1 to 40 C atoms or a branched or cyclic alkyl, alkoxy, or thioalkyl with 3-40 C-atoms which is optionally substituted by one or more radicals R$_2$, wherein each one or more non-adjacent CH$_2$ groups are optionally replaced by C(R$_2$)=C(R$_2$), Si(R$_2$)$_2$, C=NR$_2$, P(=O)(R$_2$), SO, SO$_2$, NR$_2$, O, S, or CONR$_2$ and wherein one or more H atoms are optionally replaced by D, F, Cl, Br, or I, an aromatic or heteroaromatic ring system having 6 to 40 carbon atoms which are optionally substituted by one or more radicals R$_2$, an aryloxy group having 5 to 60 aromatic ring atoms which are optionally substituted by one or more radicals R$_2$, or an aralkyl group having 5 to 60 aromatic ring atoms which are optionally substituted by one or more radicals R$_2$, wherein two or more adjacent substituents R$_1$ optionally define a mono- or polycyclic, aliphatic, aromatic, or heteroaromatic ring system with one another, which is optionally substituted with one or more radicals R$_2$; wherein R$_2$ is selected from the group consisting of H, D, F, an aliphatic hydrocarbon radical having 1 to 20 carbon atoms, or an aromatic or heteroaromatic ring system having 5 to 30 C atoms, wherein two or more adjacent substituents R$_2$ optionally define a mono- or polycyclic, aliphatic, aromatic, or heteroaromatic ring system with one another;

X is on each occurrence, identically or differently, CR$_1$ or N, with the proviso that at least one X is N;

L is on each occurrence, identically or differently, an aromatic or heteroaromatic ring system having 5-30 aromatic ring atoms, which is optionally substituted by one or more non-aromatic radicals $R_1$;

a, b, c, and d
are each, identically or differently, 0 or 1 with the proviso that at least one of a, b, c, or d is 1;

e and f
are each, identically or differently, 0, 1, 2, or 3; and n is on each occurrence, identically or differently, 0 or 1, wherein whenever a, b, c, or d is not 0, one X is nitrogen and the other is $CR_1$.

7. The compound of claim 6, wherein b is 1 while a, c, and d are 0 according to formula (VIIIa) or wherein a is 1 while b, c, and d are 0 according to formula (VIIIb):

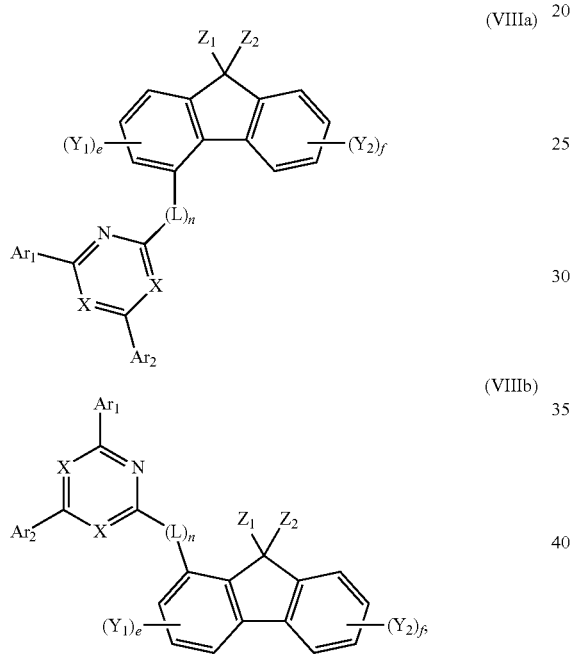

(VIIIa)

(VIIIb)

and
wherein in each formula one X is N and the other is $CR_1$.

8. The compound of claim 7, wherein the compound is a compound of formulae IX through XVII:

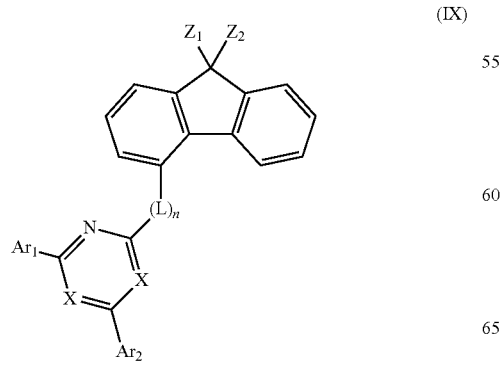

(IX)

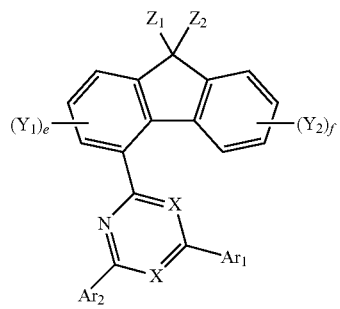

(X)

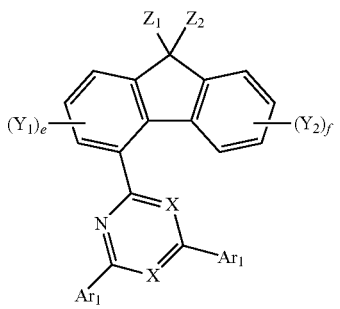

(XI)

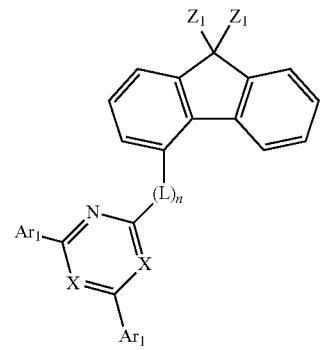

(XII)

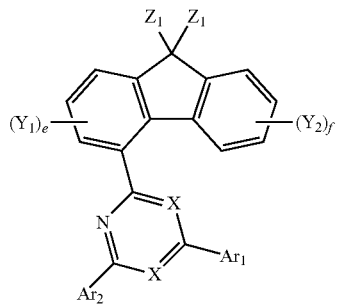

(XIII)

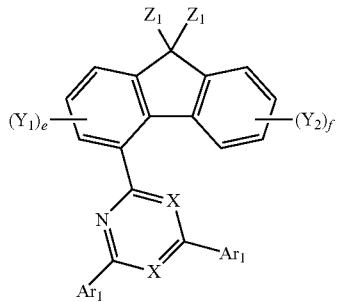

(XIV)

-continued (XV)

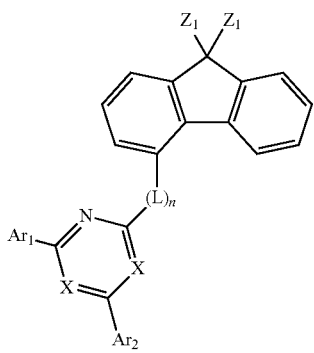

(XVI)

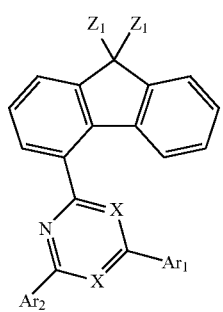

(XVII)

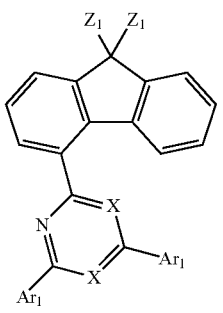

wherein, in each formula one X is N and the other is CR$_1$.

9. A compound of formula (I):

(I)

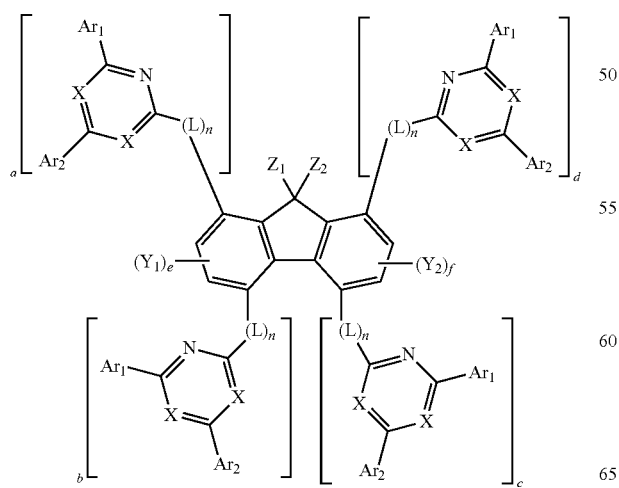

wherein:

$Z_1$ and $Z_2$
are on each occurrence, identically or differently, H, D, F, Cl, Br, I, CHO, N(Ar$_1$)$_2$, C(=O)Ar$_1$, P(=O)(Ar$_1$)$_2$, S(=O)Ar$_1$, S(=O)$_2$Ar$_1$, CR$_2$=CR$_2$Ar$_1$, CN, NO$_2$, Si(R$_1$)$_3$, B(OR$_1$)$_2$, B(R$_1$)$_2$, B(N(R$_1$)$_2$)$_2$, OSO$_2$R$_1$, a straight-chain alkyl, alkoxy, or thioalkoxy group having 1 to 40 C atoms, a straight-chain alkenyl or alkynyl group having 2 to 40 C atoms, or a branched or cyclic alkyl, alkenyl, alkynyl, alkoxy, or thioalkoxy group having 3 to 40 C atoms, each of which is optionally substituted by one or more radicals R$_1$, wherein one or more CH$_2$ groups are optionally replaced by (R$_1$)C=C(R$_1$), C≡C, Si(R$_1$)$_2$, Ge(R$_1$)$_2$, Sn(R$_1$)$_2$, C=O, C=S, C=Se, C=N(R$_1$), P(=O)(R$_1$), SO, SO$_2$, N(R$_1$)$_2$, O, S, or CON(R$_1$)$_2$, and wherein one or more H atoms are optionally replaced by D, F, Cl, Br, I, CN, or NO$_2$, an aromatic or heteroaromatic ring system having 5 to 60 aromatic ring atoms, which in each case is optionally substituted by one or more radicals R$_1$, or an aryloxy or heteroaryloxy group having 5 to 60 aromatic ring atoms, which is optionally substituted by one or more radicals R$_1$, and wherein Z$_1$ and Z$_2$ do not form a bis-spirobifluorene;

Y$_1$ and Y$_2$
are on each occurrence, identically or differently, D, F, Cl, Br, I, CHO, N(Ar$_1$)$_2$, C(=O)Ar$_1$, P(=O)(Ar$_1$)$_2$, S(=O)Ar$_1$, S(=O)$_2$Ar$_1$, (R$_1$)C=C(R$_1$)Ar$_1$, CN, NO$_2$, Si(R$_1$)$_3$, B(OR$_1$)$_2$, B(R$_1$)$_2$, B(N(R$_1$)$_2$)$_2$, OSO$_2$R$_1$, a straight-chain alkyl, alkoxy, or thioalkoxy group having 1 to 40 C atoms, a straight-chain alkenyl or alkynyl group having 2 to 40 C atoms, or a branched or cyclic alkyl, alkenyl, alkynyl, alkoxy, or thioalkoxy group having 3 to 40 C atoms, each of which is optionally substituted by one or more radicals R$_1$, wherein one or more CH$_2$ groups are optionally replaced by (R$_1$)C=C(R$_1$), C≡C, Si(R$_1$)$_2$, Ge(R$_1$)$_2$, Sn(R$_1$)$_2$, C=O, C=S, C=Se, C=N(R$_1$)$_2$, P(=O(R$_1$)$_2$, SO, SO$_2$, N(R$_1$)$_2$, O, S, or CON(R$_1$)$_2$ and wherein one or more H atoms are optionally replaced by D, F, Cl, Br, I, CN, or NO$_2$, an aromatic or heteroaromatic ring system having 5 to 60 aromatic ring atoms, which in each case is optionally substituted by one or more radicals R$_1$, or an aryloxy or heteroaryloxy group having 5 to 60 aromatic ring atoms, which is optionally substituted by one or more radicals R$_1$, or a combination of these systems; and wherein two or more adjacent substituents Y$_1$ or Y$_2$ optionally define an annulated mono- or polycyclic, aliphatic or aromatic or heteroaromatic ring system with one another;

Ar$_1$ and Ar$_2$
are on each occurrence, identically or differently, an aromatic or heteroaromatic ring system having 5 to 23 aromatic ring atoms, which in each case is optionally substituted by one or more radicals R$_1$, with the proviso that a heteroaromatic ring system is connected via a carbon-carbon bond;

R$_1$ is on each occurrence, identically or differently, H, D, F, Cl, Br, I, CN, Si(R$_2$)$_3$, a straight-chain alkyl, alkoxy, or thioalkyl group having 1 to 40 C atoms or a branched or cyclic alkyl, alkoxy, or thioalkyl with 3-40 C-atoms which is optionally substituted by one or more radicals R$_2$, wherein each one or more non-adjacent CH$_2$ groups are optionally replaced by C(R$_2$)=C(R$_2$), Si(R$_2$)$_2$, C=NR$_2$, P(=O)(R$_2$), SO, SO$_2$, NR$_2$, O, S, or CONR$_2$ and wherein one or more H atoms are optionally replaced by D, F, Cl, Br, or I, an aromatic or heteroaromatic ring system having 6 to 40 carbon atoms which are optionally substituted by one or more radicals $R_2$, an aryloxy group having 5 to 60 aromatic ring atoms which are optionally substituted by one or more radicals $R_2$, or an aralkyl group having 5 to 60 aromatic ring atoms which are optionally substituted by one or more radicals $R_2$, wherein two or more adjacent substituents $R_1$ optionally define a mono- or polycyclic, aliphatic, aromatic, or heteroaromatic ring system with one another, which is optionally substituted with one or more radicals $R_2$; wherein $R_2$ is selected from the group consisting of H, D, F, an aliphatic hydrocarbon radical having 1 to 20 carbon atoms, or an aromatic or heteroaromatic ring system having 5 to 30 C atoms, wherein two or more adjacent substituents $R_2$ optionally define a mono- or polycyclic, aliphatic, aromatic, or heteroaromatic ring system with one another;

X is on each occurrence, identically or differently, $CR_1$ or N, with the proviso that at least one X is N;

L is on each occurrence, identically or differently, an aromatic or heteroaromatic ring system having 5-30 aromatic ring atoms, which is optionally substituted by one or more non-aromatic radicals $R_1$;

a, b, c, and d
are each, identically or differently, 0 or 1 with the proviso that at least one of a, b, c, or d is 1;

e and f
are each, identically or differently, 0, 1, 2, or 3; and n is on each occurrence, identically or differently, 0 or 1, wherein $Ar_1$ is selected from the group consisting of N-phenylcarbazole, dibenzofuran, and dibenzothiophene, and wherein $Ar_2$ is selected from the group consisting of benzene, ortho-biphenyl, meta-biphenyl, para-biphenyl, ortho-terphenyl, meta-terphenyl, para-terphenyl, branched terphenyl, naphthyl, triphenylene, 9,9-dialkylfluorenyl, N-phenylcarbazole, dibenzofuran, and bidenzothiophene.

10. A process for preparing a compound of claim 5, comprising the steps of (1) synthesizing a skeleton of compound (VI) or (VII) which contains no triazinyl or pyrimidinyl group and (2) reacting the skeleton in a C—C coupling or a C—N coupling.

11. An oligomer, polymer, or dendrimer containing one or more compounds of formula (I):

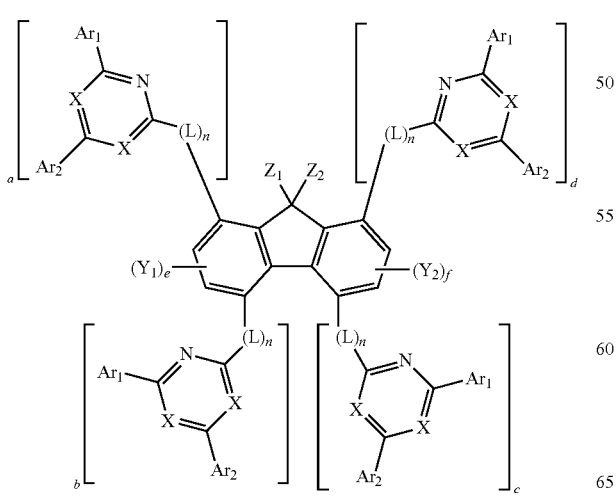

(I)

wherein:

$Z_1$ and $Z_2$
are on each occurrence, identically or differently, H, D, F, Cl, Br, I, CHO, $N(Ar_1)_2$, $C(=O)Ar_1$, $P(=O)(Ar_1)_2$, $S(=O)Ar_1$, $S(=O)_2Ar_1$, $CR_2=CR_2Ar_1$, CN, $NO_2$, $Si(R_1)_3$, $B(OR_1)_2$, $B(R_1)_2$, $B(N(R_1)_2)_2$, $OSO_2R_1$, a straight-chain alkyl, alkoxy, or thioalkoxy group having 1 to 40 C atoms, a straight-chain alkenyl or alkynyl group having 2 to 40 C atoms, or a branched or cyclic alkyl, alkenyl, alkynyl, alkoxy, or thioalkoxy group having 3 to 40 C atoms, each of which is optionally substituted by one or more radicals $R_1$, wherein one or more $CH_2$ groups are optionally replaced by $(R_1)C=C(R_1)$, $C≡C$, $Si(R_1)_2$, $Ge(R_1)_2$, $Sn(R_1)_2$, $C=O$, $C=S$, $C=Se$, $C=N(R_1)$, $P(=O)(R_1)$, SO, $SO_2$, $N(R_1)_2$, O, S, or $CON(R_1)_2$, and wherein one or more H atoms are optionally replaced by D, F, Cl, Br, I, CN, or $NO_2$, an aromatic or heteroaromatic ring system having 5 to 60 aromatic ring atoms, which in each case is optionally substituted by one or more radicals $R_1$, or an aryloxy or heteroaryloxy group having 5 to 60 aromatic ring atoms, which is optionally substituted by one or more radicals $R_1$, and wherein $Z_1$ and $Z_2$ do not form a bis-spirobifluorene;

$Y_1$ and $Y_2$
are on each occurrence, identically or differently, D, F, Cl, Br, I, CHO, $N(Ar_1)_2$, $C(=O)Ar_1$, $P(=O)(Ar_1)_2$, $S(=O)Ar_1$, $S(=O)_2Ar_1$, $(R_1)C=C(R_1)Ar_1$, CN, $NO_2$, $Si(R_1)_3$, $B(OR_1)_2$, $B(R_1)_2$, $B(N(R_1)_2)_2$, $OSO_2R_1$, a straight-chain alkyl, alkoxy, or thioalkoxy group having 1 to 40 C atoms, a straight-chain alkenyl or alkynyl group having 2 to 40 C atoms, or a branched or cyclic alkyl, alkenyl, alkynyl, alkoxy, or thioalkoxy group having 3 to 40 C atoms, each of which is optionally substituted by one or more radicals $R_1$, wherein one or more $CH_2$ groups are optionally replaced by $(R_1)C=C(R_1)$, $C≡C$, $Si(R_1)_2$, $Ge(R_1)_2$, $Sn(R_1)_2$, $C=O$, $C=S$, $C=Se$, $C=N(R_1)$, $P(=O(R_1)_2$, SO, $SO_2$, $N(R_1)_2$, O, S, or $CON(R_1)_2$ and wherein one or more H atoms are optionally replaced by D, F, Cl, Br, I, CN, or $NO_2$, an aromatic or heteroaromatic ring system having 5 to 60 aromatic ring atoms, which in each case is optionally substituted by one or more radicals $R_1$, or an aryloxy or heteroaryloxy group having 5 to 60 aromatic ring atoms, which is optionally substituted by one or more radicals $R_1$, or a combination of these systems; and wherein two or more adjacent substituents $Y_1$ or $Y_2$ optionally define an annulated mono- or polycyclic, aliphatic or aromatic or heteroaromatic ring system with one another;

$Ar_1$ and $Ar_2$
are on each occurrence, identically or differently, an aromatic or heteroaromatic ring system having 5 to 23 aromatic ring atoms, which in each case is optionally substituted by one or more radicals $R_1$, with the proviso that a heteroaromatic ring system is connected via a carbon-carbon bond;

$R_1$ is on each occurrence, identically or differently, H, D, F, Cl, Br, I, CN, $Si(R_2)_3$, a straight-chain alkyl, alkoxy, or thioalkyl group having 1 to 40 C atoms or a branched or cyclic alkyl, alkoxy, or thioalkyl with 3-40 C-atoms which is optionally substituted by one or more radicals $R_2$, wherein each one or more non-adjacent $CH_2$ groups are optionally replaced by $C(R_2)=C(R_2)$, $Si(R_2)_2$, $C=NR_2$, $P(=O)(R_2)$, SO, $SO_2$, $NR_2$, O, S, or $CONR_2$ and wherein one or more H atoms are optionally replaced by D, F, Cl, Br, or I, an aromatic or heteroaromatic ring system having 6 to 40 carbon atoms which are optionally substituted by one or more radicals $R_2$, an aryloxy group having 5 to 60 aromatic ring atoms which are optionally substituted by one or more radicals $R_2$, or an aralkyl group having 5 to 60 aromatic ring atoms which are optionally substituted by one or more radicals $R_2$, wherein two or more adjacent substituents $R_1$ optionally define a mono- or polycyclic, aliphatic, aromatic, or heteroaromatic ring system with one another, which is optionally substituted with one or more radicals $R_2$; wherein $R_2$ is selected from the group consisting of H, D, F, an aliphatic hydrocarbon radical having 1 to 20 carbon atoms, or an aromatic or heteroaromatic ring system having 5 to 30 C atoms, wherein two or more adjacent substituents $R_2$ optionally define a mono- or polycyclic, aliphatic, aromatic, or heteroaromatic ring system with one another;

X is on each occurrence, identically or differently, $CR_1$ or N, with the proviso that at least one X is N;

L is on each occurrence, identically or differently, an aromatic or heteroaromatic ring system having 5-30 aromatic ring atoms, which is optionally substituted by one or more non-aromatic radicals $R_1$;

a, b, c, and d
are each, identically or differently, 0 or 1 with the proviso that at least one of a, b, c, or d is 1;

e and f
are each, identically or differently, 0, 1, 2, or 3; and n is on each occurrence, identically or differently, 0 or 1, wherein one or more bonds from the compound to the polymer, oligomer, or dendrimer are present instead of substituents at one or more positions.

12. A formulation comprising at least one compound of claim 5 and at least one solvent.

13. A formulation comprising an oligomer, polymer, or dendrimer of claim 11 and at least one solvent.

14. An electronic device comprising at least one compound of claim 5.

15. The electronic device of claim 14, wherein the electronic device is selected from the group consisting of organic electroluminescent devices, organic integrated circuits, organic field-effect transistors, organic thin-film transistors, organic light-emitting transistors, organic solar cells, dye-sensitised organic solar cells, organic optical detectors, organic photoreceptors, organic field-quench devices, light-emitting electrochemical cells, organic laser diodes, and organic plasmon emitting devices.

16. An electronic device comprising the oligomer, polymer, or dendrimer of claim 11.

17. The electronic device of claim 16, wherein the electronic device is selected from the group consisting of organic electroluminescent devices, organic integrated circuits, organic field-effect transistors, organic thin-film transistors, organic light-emitting transistors, organic solar cells, dye-sensitised organic solar cells, organic optical detectors, organic photoreceptors, organic field-quench devices, light-emitting electrochemical cells, organic laser diodes, and organic plasmon emitting devices.

18. An organic electroluminescent device comprising a matrix material for a phosphorescent or fluorescent emitter, an electron-blocking or exciton-blocking layer, a charge generation layer, a hole-blocking layer, and/or an electron-transport layer comprising a matrix material comprising a compound of claim 1.

19. An organic electroluminescent device comprising a matrix material for a phosphorescent or fluorescent emitter, an electron-blocking or exciton-blocking layer, a charge generation layer, a hole-blocking layer, and/or an electron-transport layer comprising a matrix material comprising an oligomer, polymer, or dendrimer of claim 11.

20. A formulation comprising at least one compound of claim 1 and at least one solvent.

21. A formulation comprising at least one compound of claim 6 and at least one solvent.

22. A formulation comprising at least one compound of claim 9 and at least one solvent.

23. An electronic device comprising at least one compound of claim 1.

24. An electronic device comprising at least one compound of claim 6.

25. An electronic device comprising at least one compound of claim 9.

26. The electronic device according to claim 25, wherein the electronic device is selected from the group consisting of organic electroluminescent devices, organic integrated circuits, organic field-effect transistors, organic thin-film transistors, organic light-emitting transistors, organic solar cells, dye-sensitised organic solar cells, organic optical detectors, organic photoreceptors, organic field-quench devices, light-emitting electrochemical cells, organic laser diodes, and organic plasmon emitting devices.

27. A process for preparing a compound of claim 1, comprising the steps of (1) synthesizing a skeleton of compound (IV) or (V) which contains no triazinyl or pyrimidinyl group and (2) reacting the skeleton in a C—C coupling or a C—N coupling.

28. A process for preparing a compound of claim 6, comprising the steps of (1) synthesizing a skeleton of compound (I) which contains no triazinyl or pyrimidinyl group and (2) reacting the skeleton in a C—C coupling or a C—N coupling.

29. A process for preparing a compound of claim 9, comprising the steps of (1) synthesizing a skeleton of compound (I) which contains no triazinyl or pyrimidinyl group and (2) reacting the skeleton in a C—C coupling or a C—N coupling.

30. The electronic device according to claim 23, wherein the electronic device is selected from the group consisting of organic electroluminescent devices, organic integrated circuits, organic field-effect transistors, organic thin-film transistors, organic light-emitting transistors, organic solar cells, dye-sensitised organic solar cells, organic optical detectors, organic photoreceptors, organic field-quench devices, light-emitting electrochemical cells, organic laser diodes, and organic plasmon emitting devices.

31. The electronic device according to claim 24, wherein the electronic device is selected from the group consisting of organic electroluminescent devices, organic integrated circuits, organic field-effect transistors, organic thin-film transistors, organic light-emitting transistors, organic solar cells, dye-sensitised organic solar cells, organic optical detectors, organic photoreceptors, organic field-quench devices, light-emitting electrochemical cells, organic laser diodes, and organic plasmon emitting devices.

32. An organic electroluminescent device comprising a matrix material for a phosphorescent or fluorescent emitter, an electron-blocking or exciton-blocking layer, a charge generation layer, a hole-blocking layer, and/or an electron-transport layer comprising a matrix material comprising an oligomer, polymer, or dendrimer of claim 6.

33. An organic electroluminescent device comprising a matrix material for a phosphorescent or fluorescent emitter, an electron-blocking or exciton-blocking layer, a charge generation layer, a hole-blocking layer, and/or an electron-transport layer comprising a matrix material comprising an oligomer, polymer, or dendrimer of claim 9.

\* \* \* \* \*